United States Patent [19]

Gray et al.

[11] Patent Number: 4,913,837

[45] Date of Patent: Apr. 3, 1990

[54] HETEROCYCLIC COMPOUNDS

[75] Inventors: George W. Gray, Cottingham; Kenneth J. Toyne; David Lacey, both of Hull; Michael P. Burrow, Bristol, all of Great Britain; Rudolf Eidenschink, Mühltal, Fed. Rep. of Germany; Andreas Wächtler, Griesheim, Fed. Rep. of Germany; Georg Weber, Erzhausen, Fed. Rep. of Germany

[73] Assignee: Merck Patent Gesellschaft mit beschrankter Haftung, Darmstadt, Fed. Rep. of Germany

[21] Appl. No.: 116,079

[22] PCT Filed: Dec. 18, 1986

[86] PCT No.: PCT/EP86/00760

§ 371 Date: Sep. 1, 1987

§ 102(e) Date: Sep. 1, 1987

[87] PCT Pub. No.: WO87/04158

PCT Pub. Date: Jul. 16, 1987

[30] Foreign Application Priority Data

Jan. 3, 1986 [DE] Fed. Rep. of Germany ....... 3600052

[51] Int. Cl.$^4$ .................. G02F 1/13; C09K 19/34; C07D 409/00; C07D 241/18
[52] U.S. Cl. .................. 252/299.61; 252/299.01; 252/299.5; 350/350 R; 350/350 S; 546/286; 546/290; 546/298; 546/300; 546/301; 546/302; 546/314; 546/326; 546/328; 546/330; 546/335; 546/339; 546/342
[58] Field of Search ........... 252/299.01, 299.5, 299.61; 350/350 R, 350 S; 546/286, 290, 298, 300, 301, 302, 314, 326, 328, 330, 335, 339, 342

[56] References Cited

U.S. PATENT DOCUMENTS

| 4,256,656 | 3/1981 | Beguin et al. ............... | 252/299.61 |
|---|---|---|---|
| 4,592,857 | 6/1986 | Sugimori et al. ............ | 252/299.61 |
| 4,642,199 | 2/1987 | Sugimori ...................... | 252/299.61 |
| 4,659,500 | 4/1987 | Sugimori et al. ............ | 252/299.61 |
| 4,659,502 | 4/1987 | Fearon et al. ................ | 252/299.61 |
| 4,668,425 | 5/1987 | Nigorikawa et al. ........ | 252/299.61 |
| 4,668,426 | 5/1987 | Demus et al. ................ | 252/299.61 |
| 4,684,220 | 8/1987 | Shionozaki et al. ......... | 252/299.61 |
| 4,684,477 | 8/1987 | Sugimori et al. ............ | 252/299.61 |
| 4,713,197 | 12/1987 | Eidenschink et al. ...... | 252/299.61 |
| 4,721,367 | 1/1988 | Yoshinaga et al. .......... | 252/299.61 |
| 4,723,018 | 2/1988 | Shionozaki et al. ......... | 252/299.61 |
| 4,744,918 | 5/1988 | Heppke et al. .............. | 252/299.61 |
| 4,752,413 | 6/1988 | Inoue et al. .................. | 252/299.61 |
| 4,753,752 | 6/1988 | Raynes et al. ............... | 252/299.61 |
| 4,772,416 | 9/1988 | Goto et al. ................... | 252/299.61 |
| 4,776,973 | 10/1988 | Bofinger et al. ............. | 252/299.61 |
| 4,820,839 | 4/1989 | Krause et al. ................ | 252/299.61 |
| 4,826,979 | 5/1989 | Kamo ............................ | 252/299.61 |
| 4,834,904 | 5/1989 | Krause et al. ................ | 252/299.61 |

FOREIGN PATENT DOCUMENTS

| 206228 | 12/1986 | European Pat. Off. ....... | 252/299.61 |
|---|---|---|---|
| 240386 | 10/1986 | Fed. Rep. of Germany ...................... | 252/299.61 |
| 61241727 | 10/1986 | Fed. Rep. of Germany ...................... | 252/299.61 |
| 3515373 | 11/1986 | Fed. Rep. of Germany ...................... | 252/299.61 |
| 3518734 | 11/1986 | Fed. Rep. of Germany ...................... | 252/299.61 |
| 58-121272 | 7/1983 | Japan ............................ | 252/299.61 |
| 59-144771 | 8/1984 | Japan ............................ | 252/299.61 |
| 60-92276 | 5/1985 | Japan ............................ | 252/299.61 |
| 60-149564 | 8/1985 | Japan ............................ | 252/299.61 |
| 60-163865 | 8/1985 | Japan ............................ | 252/299.61 |
| 61-24571 | 2/1986 | Japan ............................ | 252/299.61 |
| 61-246167 | 11/1986 | Japan ............................ | 252/299.61 |
| 62-00071 | 1/1987 | Japan ............................ | 252/299.61 |
| 62-22889 | 1/1987 | Japan ............................ | 252/299.61 |
| 62-155257 | 7/1987 | Japan ............................ | 252/299.61 |
| 62-172089 | 7/1987 | Japan ............................ | 252/299.61 |
| 62-172090 | 7/1987 | Japan ............................ | 252/299.61 |
| 63-48254 | 2/1988 | Japan ............................ | 252/299.61 |
| 63-81193 | 4/1988 | Japan ............................ | 252/299.61 |
| 60199882 | 10/1988 | Japan ............................ | 252/299.61 |
| 2092169 | 8/1982 | United Kingdom .......... | 252/299.61 |
| 2153345 | 8/1985 | United Kingdom .......... | 252/299.61 |
| 8604060 | 7/1986 | World Int. Prop. O. ...... | 252/299.61 |
| 8606401 | 11/1986 | World Int. Prop. O. ...... | 252/299.61 |

OTHER PUBLICATIONS

Green, D. C. et al., IBM Tech. Discl. Bull., vol. 15, No. 8, pp. 2467–2468 (1973).
Karamysheva, L. A. et al., Mol. Cryst. Liq. Cryst., vol. 67, pp. 241–252 (1981).
Pavluchenko, A. I., et al., Abstracts, The Tenth International Liquid Crystal Conf., I30, York, U.K. (Jul. 15–21, 1984).
Grachev, V. T. et al., Mol. Cryst. Liq. Cryst., vol. 65, pp. 133–144 (1981).
Schubert, H., Wiss. Z. Univ. Halle, XIX '70 M, H.5, pp. 1–18.
Pavluchenko, A. I. et al., J. De. Physique, coll C3, Supp. No. 4, vol. 40, pp. C3-2-4 (Apr. 1979).
Dewar, M. B. S. et al., Liquid Crystals and Ordered Fluids, vol. 2, pp. 733–741, Plenum Press, N.Y. (1974).

Primary Examiner—Teddy S. Gron
Attorney, Agent, or Firm—Millen, White & Zelano

[57] ABSTRACT

Heterocyclic compounds of the formula I $$R^1\text{-}A^1\text{-}Z^1\text{-}A^2\text{-}[Z^2\text{-}A^3]_n\text{-}R^2 \qquad \text{I}$$

wherein $R^1$, $R^2$, $A^1$, $A^2$, $A^3$, $Z^1$, $Z^2$ and n are defined in claim 1, can be used as components of liquid-crystalline phases.

10 Claims, No Drawings

HETEROCYCLIC COMPOUNDS

The invention relates to heterocyclic compounds of the formula I $$R^1\text{-}A^1\text{-}Z^1\text{-}A^2[Z^2\text{-}A^3]_n\text{-}R^2 \qquad (I)$$

wherein $R^1$ and $R^2$ are each independently of each other an alkyl group of 1-15 C atoms, wherein one or two nonadjacent $CH_2$ groups can also be replaced by O atoms and/or —CO— groups and/or —O—CO— groups and/or —CO—O— groups and/or —O—COO— groups and/or —CHCN— and/or —CH— halogen groups, and one of the radicals $R^1$ and $R^2$ is also F, Cl, Br or CN, $A^1$, $A^2$ and $A^3$ are each independently of one another a 1,4-cyclohexylene group which is unsubstituted or monosubstituted or polysubstituted by F and/or Cl atoms and/or $CH_3$ and/or CN groups, wherein one or two non-adjacent $CH_2$ groups can also be replaced by O atoms and/or S atoms, or a 1,4-bicyclo-(2,2,2)-octylene group or a 1,4 phenylene group which is unsubstituted or monosubstituted or polysubstituted by F and/or Cl atoms and/or $CH_3$ and/or CN groups, wherein one or more CH groups can also be replaced by N, $Z^1$ and $Z^2$ are each independently of each other —CO—O—, —O—CO—, —$CH_2CH_2$—, —$OCH_2$—, —$CH_2O$— or a single bond, n is 0, 1 or 2, with the provisos that
(a) at least one of the groups $A^1$ and $A^2$ is a pyrazine-2,5-diyl group (Pa) or a pyridine-2,5-diyl group (Py),
(b) in the case of pyrazine compounds at least one of the groups $Z^1$ and $Z^2$ is not a single bond and/or at least one of the groups $A^1$, $A^2$ and $A^3$ is a laterally substituted 1,4-phenylene group,
(c) in the case of —$A^1$—$Z^1$—$A^2$—=

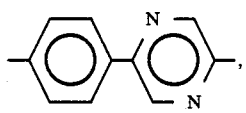

n=1 and $Z^2$=—O—CO—, $R^1$ and $R^2$ are each independently of each other a straight-chain alkyl group with 1-15 C atoms, wherein one or two non-adjacent $CH_2$ groups can also be replaced by 0 atoms and/or —CO— groups and/or —O—CO— groups and/or —CO—O— groups and/or —O—COO— groups and/or —CHCN— and/or —CH-halogen groups, one of the radicals $R^1$ and $R^2$ is also F, Cl, Br or CN and $A^3$ is an unsubstituted 1,4-phenylene group, or $R^1$ and $R^2$ are each independently of each other a straight-chain or branched alkyl group with 1-15 C atoms, wherein one or two non-adjacent $CH_2$ groups can also be replaced by O atoms and/or —CO— groups and/or —O—CO— groups and/or —CO—O— groups and/or —O—COO— groups and/or —CHCN— and/or —CH-halogen groups, one of the radicals $R^1$ and $R^2$ is also F, Cl, Br or CN and $A^3$ is laterally substituted 1,4-phenylene, (d) in the case of pyridine compounds at least one of the groups $Z^1$ and $Z^2$ is —$CH_2CH_2$—, —$CH_2O$— or —$OCH_2$— and/or at least one of the groups $A^1$, $A^2$ and $A^3$ is laterally substituted and/or at least one of the groups $A^1$, $A^2$ and $A^3$ is trans-1,4-cyclohexylene, wherein one or two non-adjacent $CH_2$ groups can also be replaced by O atoms and/or S atoms, or is a 1,4-bicyclo-(2,2,2)octylene group, (e) in the case of —$A^1$—$Z^1$—$A^2$—=

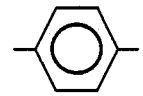

and n=1,
the $Z^2$ group linked to $A^2$ is —$CH_2CH_2$— or —$CH_2O$— or —$OCH_2$— or —$(Z^2$—$A^3)_n$—=

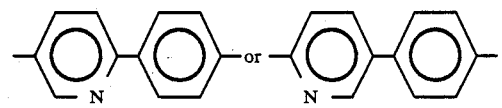

or —CO—O—$A^3$—$R^2$ or —O—CO—$A^3$—$R^2$, wherein $A^3$ is laterally substituted 1,4-phenylene or 1,4-cyclohexylene, (f) in the case of —$A^1$—$Z^1$—$A^2$—=

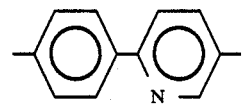

and
n=1, the group linked to $A^2$ is —$CH_2CH_2$—, or —$CH_2O$— or —$OCH_2$— or —$(Z^2$—$A^3)_n$—=—CO—O—$A^3$—$R^2$ or —O—CO—$A^3$—$R^2$, wherein $A^3$ is laterally substituted 1,4-phenylene or 1,4-cyclo hexylene, (g) in the case of pyridine compounds if n=0, $Z^1$ is a single bond and $A^2$ is laterally substituted 1,4-phenylene or —$Z^1$—$A^2$—$R^2$=

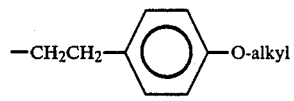

and $R^1$ is alkyl,
(h) in the case of —$A^1$—$Z^1$—=

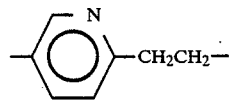

n=1 and $Z^2$ is a single bond, $A^2$ and $A^3$ are each unsubstituted or laterally substituted 1,4-phenylene, $R^2$ is alkoxy and $R^1$ is alkyl.

For simplicity, in what follows Cy is a 1,4-cyclohexylene group, Dio is a 1,3-dioxane-2,5-diyl group, Dit is a 1,3-dithiane-2,5-diyl group, Bi a 1,4-bicyclo(2,2,2)-octylene group, Phe a 1,4-phenylene group (which, if appropriate, may also be laterally substituted by F, Cl, $CH_3$ or CN), Pa is a pyrazine-2,5-diyl group and Py is a pyridine-2,5-diyl group.

Similar compounds are known for example from German Pat. No. 2,535,046. The compounds specified therein, unlike the present compounds, contain no pyrazine-2,5-diyl or pyridine-2,5-diyl group.

Similar pyridine compounds are also known for example from JP 60 149,564—A and JP 60 163,865—A. Similar pyrazine compounds are described for example in JP 60 199,882-A.

The compounds of the formula I can be employed like similar compounds as components of liquid-crystalline phases, in particular for displays which are based on the principle of the twisted cell (TN displays), the guest-host effect, the effect of the deformation of aligned phases, the effect of dynamic scattering or the SSFLC principle.

The invention had for its object to find new stable liquid crystal or mesogenic compounds which are suitable for use as components of liquid-crystalline phases.

It was found that the compounds of the formula I are highly suitable for use as components of liquid-crystalline phases. They are suitable in particular for producing stable liquid-crystalline phases for TN displays having high multiplexing rates, wide operating ranges and advantageous elastic properties. These phases also exhibit a pronounced nematogenic behavior and favorable switching times, in particular at low temperatures. Compounds of the formula I, in particular optically active compounds of the formula I, are further suitable for use as components of ferroelectric liquid crystal phases, for example for displays based on the SSFLC principle.

The compounds of the formula I also very generally serve to appreciably widen the range of liquid-crystalline substances which from various application aspects are suitable for preparing liquid-crystalline mixtures.

The compounds of the formula I have a wide application range. Depending on the choice of substituents, these compounds can serve as base materials of which liquid-crystalline phases are predominantly composed; but it is also possible to add compounds of the formula I to liquid-crystalline base materials of other compound classes, for example to optimize the dielectric and/or optical anisotropy or other parameters of such a dielectric medium. The compounds of the formula I are further suitable for use as intermediates for producing other substances which can be used as constituents of liquid-crystalline phases.

The compounds of the formula I are colorless in the pure state and form liquid-crystalline mesophases within a temperature range which is favorably positioned for electrooptical use. They are very stable chemically, thermally and to light.

The present invention thus provides the compounds of the formula I as well as a process for their preparation, wherein a compound which otherwise conforms to the formula I but contains in place of H atoms one or more reducible groups and/or C—C bonds is treated with a reducing agent, or to prepare esters of the formula I (wherein $R^1$ and/or $R^2$ are an alkyl group wherein one or two $CH_2$ groups have been replaced by —O—CO— groups and/or —CO—O— groups and/or wherein $Z^1$ and/or $Z^2$ are —CO—O— or —O—CO—) a corresponding carboxylic acid or one of its reactive derivatives is reacted with a corresponding alcohol or one of its reactive derivatives, or to prepare 1,3-dioxane derivatives or 1,3-dithiane derivatives of the formula I (wherein $A^1$ or $A^2$ or $A^3$ is 1,3-dioxane-2,5-diyl or 1,3-dithiane-2,5-diyl) a corresponding aldehyde is reacted with a corresponding diol or dithiol, or to prepare ethers of the formula I (wherein $R^1$ and/or $R^2$ is an alkyl group wherein one or two $CH_2$ groups have been replaced by O atoms and/or $Z^1$ and/or $Z^2$ is an —$OCH_2$— or —$CH_2$—O— group) a corresponding hydroxy compound is etherified, or to prepare nitriles of the formula I (wherein $R^1$ or $R^2$ is CN and/or $A^1$ and/or $A^2$ and/or $A^3$ are substituted by at least one CN group) corresponding acid amides are dehydrated or the corresponding acid halides are reacted with sulfamide, or to prepare compounds of the formula I (wherein $A^1$ and/or $A^2$ and/or $A^3$ are substituted by F and/or Cl atoms) the corresponding diazonium salts are reacted by the Schiemann or Sandmeyer method, and/or, if appropriate, a base of the formula I is converted by treatment with an acid into one of its acid addition salts, or, if appropriate, a compound of the formula I is freed from one of its acid addition salts by treatment with a base.

The invention further provides the use of the compounds of the formula I as components of liquid-crystalline phases. The invention also provides liquid-crystalline phases containing at least one compound of the formula I and liquid crystal display elements, in particular electrooptical display elements, which contain such phases.

The invention also provides a Clark and Lagerwall ferroelectric display containing compounds of formula I. Therein preference is given to compounds of the formula I in which $A^1$, $A^2$ and $A^3$ are aromatic rings. Particular preference is given therein to compounds in which at least one aromatic ring is laterally substituted. Therein $R^1$ and $R^2$ are preferably alkyl or alkoxy groups, preferably each having 5–15 C atoms. $R^1$ and $R^2$ together preferably have at least 10 C atoms.

Heretofore and hereinafter $R^1$, $R^2$, $A^1$, $A^2$, $A^3$, $Z^1$, $Z^2$ and n have the specified meaning, unless expressly stated otherwise.

The compounds of the formula I correspondingly comprise compounds of the partial formulae Ia and Ib (with two rings), Ic to If (with three rings) and Ig to In (with four rings):

| | |
|---|---|
| $R^1$—$A^1$—$A^2$—$R^2$ | Ia |
| $R^1$—$A^1$—$Z^1$—$A^2$—$R^2$ | Ib |
| $R^1$—$A^1$—$A^2$—$A^3$—$R^2$ | Ic |
| $R^1$—$A^1$—$Z^1$—$A^2$—$A^3$—$R^2$ | Id |
| $R^1$—$A^1$—$A^2$—$Z^2$—$A^3$—$R^2$ | Ie |
| $R^1$—$A^1$—$Z^1$—$A^2$—$Z^2$—$A^3$—$R^2$ | If |
| $R^1$—$A^1$—$A^2$—$A^3$—$A^3$—$R^2$ | Ig |
| $R^1$—$A^1$—$Z^1$—$A^2$—$A^3$—$A^3$—$R^2$ | Ih |
| $R^1$—$A^1$—$A^2$—$Z^2$—$A^3$—$A^3$—$R^2$ | Ii |
| $R^1$—$A^1$—$A^2$—$A^3$—$Z^2$—$A^3$—$R^2$ | Ij |
| $R^1$—$A^1$—$Z^1$—$A^2$—$Z^2$—$A^3$—$A^3$—$R^2$ | Ik |
| $R^1$—$A^1$—$Z^1$—$A^2$—$A^3$—$Z^2$—$A^3$—$R^2$ | Il |
| $R^1$—$A^1$—$A^2$—$Z^2$—$A^3$—$Z^2$—$A^3$—$R^2$ | Im |
| $R^1$—$A^1$—$Z^1$—$A^2$—$Z^2$—$A^3$—$Z^2$—$A^3$—$R^2$ | In |

Thereof those of the partial formula Ia, Ib, Ic, Id, Ig, Ih, Ii, Ij and Ik, but in particular Ic, Id, Ie and Ii, are particularly preferred.

Particular preference is given to compounds of the formula I wherein one of the groups $Z^1$ and $Z^2$ is not a single bond.

The preferred compounds of the partial formula Ia comprise those of the partial formulae Iaa to Iac, where PheX is laterally substituted 1,4-phenylene:

| | |
|---|---|
| R¹—PheX—Pa—R² | Iaa |
| R¹—PheX—Py—R² | Iab |

Thereof those of the partial formula Iab are particularly preferred. The lateral substituent is preferably fluorine.

The preferred compounds of the partial formula Ib comprise those of the partial formulae Iba to Ibh:

| | |
|---|---|
| R¹—Pa—OCO—A²—R² | Iba |
| R¹—Pa—COO—A²—R² | Ibb |
| R¹—Pa—OCH₂—A²—R² | Ibc |
| R¹—Pa—CH₂O—A²—R² | Ibd |
| R¹—Pa—CH₂CH₂—A²—R² | Ibe |
| R¹—Py-CH₂CH₂—A²—R² | Ibf |
| R¹—Py-OCH₂—A²—R² | Ibg |
| R¹—Py-CH₂O—A²—R² | Ibh |

In the partial formulae Iba to Ibh, A² is preferably Cy, Phe or laterally substituted Phe.

Thereof those of the partial formulae Iba, Ibb, Ibf and Ibg are particularly preferred.

The preferred compounds of the partial formula Ic comprise those of the partial formulae Ica to Icl, where Phe is unsubstituted and PheX is laterally substituted 1,4-phenylene:

| | |
|---|---|
| R¹—PheX—Pa—Phe—R² | Ica |
| R¹—Cy-Pa—PheX—R² | Icb |
| R¹—Pa—Phe—PheX—R² | Icc |
| R¹—Pa—Cy-PheX—R² | Icd |
| R¹—Pa—PheX—Cy-R² | Ice |
| R¹—Py-Phe—Phe—R² | Icf |
| R¹—Cy-Py-PheX—R² | Icg |
| R¹—PheX—Py-Phe—R² | Ich |
| R¹—Py-Cy-Phe—R² | Ici |
| R¹—Py-PheX—Cy-R² | Icj |
| R¹—Cy-Py-Cy-R² | Ick |
| R¹—Py-Cy-Cy-R² | Icl |

Thereof those of the partial formuale Ica, Icb, Icc, Icf, Ich, Ici, Ick and Icl are particularly preferred.

The preferred compounds of the partial formula Id comprise those of the partial formulae Ida to Idw:

| | |
|---|---|
| R¹—A¹—COO—Pa—A³—R² | Ida |
| R¹—Pa—COO—A²—A³—R² | Idb |
| R¹—A¹—OCO—Pa—A³—R² | Idc |
| R¹—Pa—OCO—A²—A³—R² | Idd |
| R¹—A¹—CH₂—CH₂—Pa—A³—R² | Ide |
| R¹—Pa—CH₂—CH₂—A²—A³—R² | Idf |
| R¹—A¹—OCH₂—Pa—A³—R² | Idg |
| R¹—Pa—OCH₂—A²—A³—R² | Idh |
| R¹—A¹—CH₂—O—Pa—A³—R² | Idi |
| R¹—A¹—OCH₂—Pa—A³—R² | Idj |
| R¹—Phe—Z¹—Pa—Phe—R² | Idk |
| R¹—Pa—Z¹—Phe—Phe—R² | Idl |
| R¹—Phe—Z¹—Pa—Cy-R² | Idm |
| R¹—Cy-Z¹—Pa—Phe—R² | Idn |
| R¹—Phe—Z¹—Pa—Bi—R² | Ido |
| R¹—Dit-Z¹—Pa—Cy-R² | Idp |
| R¹—Py-Z¹—Phe—Phe—R² | Idq |
| R¹—Phe—Z¹—Py-Phe—R² | Idr |
| R¹—Phe—Z¹—Py-Cy-R² | Ids |
| R¹—Cy-Z¹—Py-Phe—R² | Idt |
| R¹—Phe—Z¹—Py-Bi—R² | Idu |
| R¹—Dit-Z¹—Py-Cy-R² | Idv |
| R¹—Py-Z¹—Cy-Cy-R² | Idw |

Thereof those of the partial formula Ida, Idc, Idi, Idq, Idr, Ids, Idt and Idw are particularly preferred.

The preferred compounds of the partial formula Ie comprise those of the partial formulae Iea to Ieq:

| | |
|---|---|
| R¹—A¹—A²—COO—A³—R² | Iea |
| R¹—A¹—A²—OCO—A³—R² | Ieb |
| R¹—A¹—A²—CH₂—CH₂—A³—R² | Iec |
| R¹—A¹—A²—OCH₂—A³—R² | Ied |
| R¹—A¹—A²—CH₂O—A³R² | Iee |
| R¹—Phe—Pa—Z²—Phe—R² | Ief |
| R¹—Pa—Phe—Z²—Phe—R² | Ieg |
| R¹—Phe—Pa—Z²—Cy-R² | Ieh |
| R¹—Pa—Phe—Z²—Cy-R² | Iei |
| R¹—Cy-Pa—Z²—Dit-R² | Iej |
| R¹—Phe—Py-Z²—Phe—R² | Iek |
| R¹—Py-Phe—Z²—Phe—R² | Iel |
| R¹—Phe—Py-Z²—Cy-R² | Iem |
| R¹—Py-Phe—Z²—Cy-R² | Ien |
| R¹—Cy-Py-Z²—Dit-R² | Ieo |
| R¹—Cy-Py-Z²—Cy-R² | Iep |
| R¹—Py-Cy-Z²—Cy-R² | Ieq |

Thereof particular preference is given to those of the partial formula Ief, Ieg, Ieh, Iei, Iek, Iel, Iem, Ien and Iep.

The preferred compounds of the partial formula If comprise those of the partial formulae Ifa to Ifk:

| | |
|---|---|
| R¹—A¹—COO—A²—COO—A³—R² | Ifa |
| R¹—A¹—COO—A²—OCO—A³—R² | Ifb |
| R¹—A¹—OCO—A²—COO—A³—R² | Ifc |
| R¹—A¹—OCO—A²—OCO—A³—R² | Ifd |
| R¹—A¹—COO—A²—CH₂CH₂—A³—R² | Ife |
| R¹—A¹—OCO—A²—CH₂CH₂—A³—R² | Iff |
| R¹—A¹—OCO—A²—OCH₂—A³—R² | Ifg |
| R¹—A¹—CH₂—CH₂—A²—COO—A³—R² | Ifh |
| R¹—A¹—CH₂—CH₂—A²—CH₂O—A³—R² | Ifi |
| R¹—A¹—CH₂—CH₂—A²—OCO—A³—R² | Ifj |
| R¹—A¹—CH₂—CH₂—A²—CH₂—CH₂—A³—R² | Ifk |

The preferred compounds of the partial formula Ig comprise those of the partial formulae Iga to Igj, where Phe is, if appropriate, laterally substituted:

| | |
|---|---|
| R¹—Phe—Pa—Phe—Phe—R² | Iga |
| R¹—Phe—Pa—Cy-Phe—R² | Igb |
| R¹—Pa—Phe—Cy-Phe—R² | Igc |
| R¹—Cy-Pa—Phe—Cy-R² | Igd |
| R¹—Phe—Py-Phe—Phe—R² | Ige |
| R¹—Phe—Py-Cy-Phe—R² | Igf |
| R¹—Py-Phe—Cy-Phe—R² | Igg |
| R¹—Cy-Py-Phe—Cy-R² | Igh |
| R¹—Py-Cy-Cy-Cy-R² | Igi |
| R¹—Cy-Py-Cy-Cy-R² | Igj |

Thereof particular preference is given to those of the partial formulae Igh and Igi.

The preferred compounds of the partial formula Ih comprise those of the partial formulae Iha to Ihn:

| | |
|---|---|
| R¹—A¹—COO—A²—A³—A³—R² | Iha |
| R¹—A¹—OCO—A²—A³—A³—R² | Ihb |
| R¹—A¹—CH₂—CH₂—A²—A³—A³—R² | Ihc |
| R¹—A¹—OCH₂—A²—A³—A³—R² | Ihd |
| R¹—A¹—CH₂O—A²—A³—A³—R² | Ihe |
| R¹—Phe—Z¹—Pa—Phe—Cy-R² | Ihf |
| R¹—Cy—Z¹—Pa—Phe—Cy-R² | Ihg |
| R¹—Phe—Z¹—Py—Phe—Cy-R² | Ihh |
| R¹—Cy—Z¹—Py—Phe—Cy-R² | Ihi |
| R¹—Py—Z¹—Cy—Cy—Cy-R² | Ihj |
| R¹—Py—Z¹—Cy—Phe—Phe—R² | Ihk |
| R¹—Phe—Z¹—Py—Cy—Cy-R² | Ihl |
| R¹—Py—Z¹—Phe—Cy—R² | Ihm |
| R¹—Cy—Z¹—Py—Cy—Cy-R² | Ihn |

The preferred compounds of the partial formula Ii comprise those of the partial formulae Iia to Iis:

```
R¹—A¹—A²—COO—A³—A³—R²           IIa
R¹—A¹—A²—OCO—A³—A³—R²           IIb
R¹—A¹—A²—CH₂—CH₂—A³—A³—R²       IIc
R¹—A¹—A²—OCH₂—A³—A³—R²          IId
R¹—A¹—A²—CH₂O—A³—A³—R²          IIe
R¹—Phe—Pa—Z²—Phe—Phe—R²         IIf
R¹—Phe—Pa—Z²—Cy—Phe—R²          IIg
R¹—Pa—Phe—Z²—Cy—Phe—R²          IIh
R¹—Phe—Pa—Z²—Cy—Cy—R²           IIi
R¹—Phe—Pa—Z²—Phe—Cy—R²          IIj
R¹—Pa—Phe—Z²—Cy—Cy—R²           IIk
R¹—Pa—Phe—Z²—Phe—Cy—R²          IIl
R¹—Phe—Py—Z²—Phe—Phe—R²         IIm
R¹—Py—Phe—Z²—Cy—Phe—R²          IIn
R¹—Py—Phe—Z²—Cy—Cy—R²           IIo
R¹—Py—Cy—Z²—Cy—Cy—R²            IIp
R¹—Py—Cy—Z²—Phe—Phe—R²          IIq
R¹—Cy—Py—Z²—Cy—Phe—R²           IIr
R¹—Phe—Py—Z²—Cy—Cy—R²           IIs
```

The preferred compounds of the partial formula Ij comprise those of the partial formulae Ija to Ijj:

```
R¹—A¹—A²—A³—COO—A³—R²           Ija
R¹—A¹—A²—A³—OCO—A³—R²           Ijb
R¹—A¹—A²—A³—CH₂—CH₂—A³—R²       Ijc
R¹—A¹—A²—A³—CH₂O—A³—R²          Ijd
R¹—A¹—A²—A³—OCH₂—A³—R²          Ije
R¹—Cy—Pa—Phe—Z²—Phe—R²          Ijf
R¹—Cy—Py—Phe—Z²—Phe—R²          Ijg
R¹—Py—Cy—Cy—Z²—Cy—R²            Ijh
R¹—Py—Cy—Cy—Z²—Phe—R²           Iji
R¹—Phe—Py—Cy—Z²—Cy—R²           Ijj
```

The preferred compounds of the partial formula Ik comprise those of the partial formulae Ika to Ikl:

```
R¹—A¹—COO—A²—COO—A³—A³—R²       Ika
R¹—A¹—OCO—A²—COO—A³—A³—R²       Ikb
R¹—A¹—COO—A²—OCO—A³—A³—R²       Ikc
R¹—A¹—COO—A²—CH₂—CH₂—A³—A³—R²   Ikd
R¹—A¹—CH₂—CH₂—A²—CH₂—CH₂—A³—A³—R² Ike
R¹—A¹—CH₂—CH₂—A²—OCO—A³—A³—R²   Ikf
R¹—A¹—OCH₂—A²—OCO—A³—A³—R²      Ikg
R¹—A¹—CH₂O—A²—CH₂O—A³—A³—R²     Ikh
R¹—A¹—COO—A²—CH₂O—A³—A³—R²      Iki
R¹—A¹—OCO—A²—OCO—A³—A³—R²       Ikj
R¹—A¹—OCO—A²—CH₂—CH₂—A³—A³—R²   Ikk
R¹—A¹—CH₂—CH₂—A²—COO—A³—A³—R²   Ikl
```

The preferred compounds of the partial formula Il comprise those of the partial formuale Ila to Ill:

```
R¹—A¹—COO—A²—A³—COO—A³—R²       IIa
R¹—A¹—OCO—A²—A³—COO—A³—R²       IIb
R¹—A¹—COO—A²—A³—OCO—A³—R²       IIc
R¹—A¹—OCO—A²—A³—OCO—A³—R²       IId
R¹—A¹—COO—A²—A³—CH₂—CH₂—A³—R²   IIe
R¹—A¹—COO—A²—A³—CH₂O—A³—R²      IIf
R¹—A¹—OCO—A²—A³—CH₂—CH₂—A³—R²   IIg
R¹—A¹—CH₂O—A²—A³—CH₂O—A³—R²     IIh
R¹—A¹—CH₂—CH₂—A²—A³—CH₂—CH₂—A³—R² IIi
R¹—A¹—OCH₂—A²—A³—OCO—A³—R²      IIj
R¹—A¹—CH₂—CH₂—A²—A³—COO—A³—R²   IIk
R¹—A¹—OCH₂—A²—A³—OCH₂—A³—R²     IIl
```

The preferred compounds of the partial formula Im comprise those of the partial formulae Ima to Iml:

```
R¹—A¹—A²—COO—A³—COO—A³—R²       Ima
R¹—A¹—A²—OCO—A³—COO—A³—R²       Imb
R¹—A¹—A²—CH₂—CH₂—A³—COO—A³—R²   Imc
R¹—A¹—A²—CH₂—CH₂—A³—CH₂—CH₂—A³—R² Imd
R¹—A¹—A²—OCH₂—A³—CH₂—CH₂—A³—R²  Ime
R¹—A¹—A²—OCH₂—A³—COO—A³—R²      Imf
R¹—A¹—A²—COO—A³—OCO—A³—R²       Img
R¹—A¹—A²—CH₂O—A³—COO—A³—R²      Imh
```

-continued
```
R¹—A¹—A²—CH₂O—A³—CH₂O—A³—R²     Imi
R¹—A¹—A²—OCO—A³—CH₂—CH₂—A³—R²   Imj
R¹—A¹—A²—OCH₂—A³—CH₂O—A³—R²     Imk
R¹—A¹—A²—OCO—A³—OCO—A³—R²       Iml
```

In the compounds of the foregoing and following formulae, R¹ and R² are preferably n-alkyl, —O—n-alkyl, —OCO-n-alkyl, —COO-n-alkyl or —OCOO-n-alkyl or oxaalkyl. In the n-alkyl group, one CH₂ group can also be replaced by —CH—CH₃—, —CH-halogen or —CH—CN—. Particular preference is given to compounds of the formula I wherein one of the groups R¹ and R² is alkyl and the other is alkyl, alkoxy or fluorine, preferably in particular alkyl.

A¹ and A² are preferably Cy, Phe, Py or Pa, and also preferably Dio. Preferably the compound of the formula I contains not more than one of the radicals Dio, Dit or Bi.

A³ is preferably Cy or Phe, and also Bi or Dio. Particularly preferably A³ has the meaning of laterally substituted 1,4-phenylene.

Particular preference is given to compounds of the formula I wherein one of the groups A¹ and A² is Py or Pa, preferably Py, and the other groups A³, A¹ or A² are trans-1,4-cyclohexylene or 1,4-phenylene.

If A¹, A² or A³ are substituted, the substituents are preferably Cl and/or F atoms and also CH₃ or CN g Particular preference is given therein to compounds o the formula I where the lateral substituent sits on a 1,4-phenylene group. Particular preference is given to monofluoro substitution on a 1,4-phenylene group.

Z¹ and Z² are preferably —CO—O—, —O—CO—, —CH₂O—, OCH₂— or —CH₂—CH₂— groups. Particular preference is given to the —CH₂CH₂— group.

n is preferably 1 or 2.

The alkyl radicals in the groups R¹ and/or R² can be straight-chain or branched. Preferably they are straight-chain, have 2, 3, 4, 5, 6, 7, 8, 9, 10, 11 or 12 C atoms and accordingly are preferably ethyl, propyl, butyl, pentyl, hexyl, heptyl, octyl, nonyl, decyl, undecyl or dodecyl and also methyl, tridecyl, tetradecyl or pentadecyl.

If R¹ and/or R² are alkyl radicals in which one ("alkoxy" or "oxaalkyl") or two ("alkoxyalkoxy" or "dioxaalkyl") CH₂ groups are replaced by 0 atoms, they can be straight-chain or branched. Preferably they are straight-chain, have 2, 3, 4, 5, 6 or 7 C atoms and accordingly are preferably ethoxy, propoxy, butoxy, pentoxy, hexoxy, heptoxy, 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and also methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formula I and also of the foregoing and following partial formulae with branched wing groups R¹ and R² can occasionally be of importance on account of superior solubility in the customary liquid-crystalline base materials, but in particular for use as chiral dopants, if they are optically active. Branched groups of this kind generally contain not more than one chain branching. Preferred branched radicals R¹ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 2-octyloxy, 2-chloropropionyloxy, 2-chloro-3-methylbutyryloxy, 2-chloro-4-methylvaleryloxy, 2-chloro-3-methylvaleryloxy, 2-methyl3-oxapentyl, 2-methyl-3-oxahexyl. Optically active compounds of the formula I are suitable for use as components of chirally smectic liquid crystal phases and also in nematic materials, for example to avoid reverse twist.

Particularly preferred pyrazine compounds are those in which n is 0 or 1 and one of the groups $A^1$, $A^2$ or $A^3$ is a laterally substituted 1,4-phenylene group. Particular preference is given to pyrazines which contain as $A^3$ a laterally substituted 1,4-phenylene.

Preference is also given to pyrazine compounds in which $Z^2$ is a —CH$_2$CH$_2$— group.

Preference is further given to pyrazine compounds of the formula II

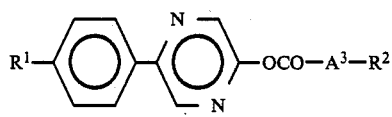   II wherein $A^3$ is preferably a laterally substituted 1,4-phenylene group. If $A^3$ is an unsubstituted 1,4-phenylene group, $R^1$ and $R^2$ in formula II are preferably straight-chain alkyl groups.

Preference is also given to pyrazine compounds of the formula I where $A^1$ is pyrazine-2,5-diyl and n is 1.

Of the pyridine compounds of the formula I, preference is given to those in which n is 1 or 2. Furthermore, preferred pyridine compounds contain at least one 1,4-cyclohexylene group or a laterally substituted 1,4-phenylene group. $Z^1$ and/or $Z^2$ are preferably a single bond, particularly preferably a —CH$_2$CH$_2$— group.

Preference is given to pyridine compounds of the formula III

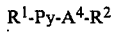   III wherein
$A^4$ is a laterally substituted 1,4-phenylene, and $R^1$ and $R^2$ have the meaning specified in the formula I but preferably one of the radicals $R^1$ and $R^2$ is alkyl and the other is alkyl or alkoxy.

Preference is given in particular to compounds of the formula IIIa

   IIIa wherein $R^1$ is preferably alkyl and X is preferably fluorine.

Preference is further given to pyridine compounds of the formula IV

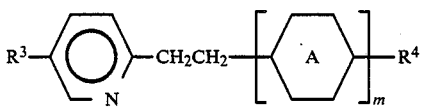   IV wherein
m is 1 or 2,
$R^3$ is an alkyl group of 1-15 atoms,
$R^4$ is an alkyloxy group whose alkyl portion has 1-14 C atoms, and

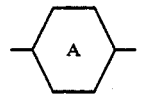

is a 1,4-phenylene group which is unsubstituted or laterally monosubstituted or polysubstituted by F and/or Cl atoms and/or CH$_3$ and/or CN groups.

Preference is further given to pyridine compounds of the formula V

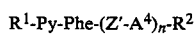   V wherein $R^1$ and $R^2$ have the specified meanings, n is 1,
Z' is a single bond, —CH$_2$CH$_2$—, —CH$_2$O—, —OCH$_2$—, —OCO— or —COO— and
$A^4$ in the case of Z'=—CH$_2$CH$_2$—, —CH$_2$O—, —OCH$_2$—, —OCO— or —COO— is a 1,4-phenylene or 1,4-cyclohexylene group which is monosubstituted or polysubstituted by F and/or Cl atoms and/or CH$_3$ and/or CN groups, or in the case of Z'=—CH$_2$CH$_2$—, —CH$_2$O— or —OCH$_2$ is also an unsubstituted 1,4-phenylene group, or in the case of Z' being a single bond is a 1,4-phenylene group which is monosubstituted or polysubstituted by F and/or Cl atoms and/or CH$_3$ and/or CN groups, or is also an unsubstituted 1,4-phenylene group.

Preference is further given to pyridine compounds of the formula VI

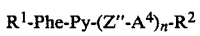   VI wherein $R^1$ and $R^2$ have the specified meaning, n is 1,
Z'' is —CH$_2$CH$_2$—, —CH$_2$O—, —OCH$_2$, —CO—O— or —O—CO—, and
$A^4$ is a 1,4-phenylene group which is monosubstituted or polysubstituted by F and/or Cl atoms and/or CH$_3$ and/or CN groups or is also a 1,4-cyclohexylene group.

Preference is also given to pyridine compounds of the formula VII

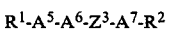   VII wherein $R^1$ and $R^2$ have the specified meaning,
$Z^3$ is —CH$_2$CH$_2$—, —CH$_2$O— or —OCH$_2$—, —COO— or —O—CO—, or a single bond,
—$A^5$—$A^6$— is Py—Cy— or —Cy—Py— and
$A^7$ is Cy.

Very particular preference is given to pyridine compounds of the formula I wherein n is 2.

Of the compounds of the formula I and also of the foregoing and following partial formulae, preference is given to those in which at least one of the radicals present therein has one of the specified preferred meanings. Particularly preferred smaller groups of compounds are those of the formulae I1 to I68, wherein PheX is

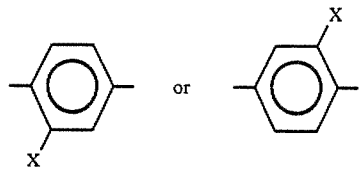

X is preferably F, Cl, CN or CH₃, in particular F.

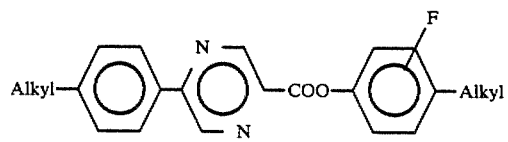
I1

| | |
|---|---|
| Alkyl-Phe—Pa—COO—Phe-Alkyl | I2 |
| Alkyl-Phe—Pa—OCO—Phe-Alkyl | I3 |
| Alkyl-Phe—Pa—OCO—PheX-Alkyl | I4 |
| Alkyl-Phe—Pa—OCH₂—Cy-Alkyl | I5 |
| Alkoxy-Pa—Phe—COO—PheX-Alkyl | I6 |
| Alkyl-Cy—Pa—CH₂—CH₂—Phe—CN | I7 |
| Alkyl-Phe—Pa—CH₂CH₂—PheX-Alkyl | I8 |
| Alkyl-Cy—CH₂O—Pa—PheX—CN | I9 |
| Alkyl-Phe—Pa—CH₂—CH₂—Phe-Alkoxy | I10 |
| Alkyl-Phe—Pa—PheX-Alkyl | I11 |
| Alkyl-Pa—PheX-Alkyl | I12 |
| Alkyl-Pa—CH₂CH₂—PheX-Alkyl | I13 |
| Alkyl-Cy—Pa—COO—Phe—Phe—CN | I14 |
| Alkyl-Phe—Pa—COO—Phe-Alkoxy | I15 |
| Alkyl-Phe—Pa—OCO—Phe-Alkoxy | I16 |
| Alkyl-Phe—Pa—COO—Phe—CN | I17 |
| Alkyl-Pa—COO—Phe-Alkyl | I18 |
| Alkyl-Pa—COO—Phe—Cy-Alkyl | I19 |
| Alkyl-Phe—Pa—COO—PheX—CN | I20 |
| Alkoxy-Phe—Pa—COO—PheX—CN | I21 |
| Alkyl-Cy—Pa—COO—PheX—CN | I22 |
| Alkyl-Pa—Phe—COO—PheX—CN | I23 |
| Alkoxy-Pa—Phe—COO—PheX—CN | I24 |
| Alkyl-Pa—Phe—OCO—Cy-Alkyl | I25 |
| Alkoxy-Pa—Phe—CH₂CH₂—Cy-Alkyl | I26 |
| Alkyl-Pa—Phe—CH₂CH₂—Cy-Alkyl | I27 |
| Alkoxy-Pa—Phe—COO—Cy-Alkyl | I28 |
| Alkyl-Phe—Py—COO—PheX-Alkyl | I29 |
| Alkyl-Py—PheX-Alkyl | I30 |
| Alkyl-Py—PheX-Alkoxy | I31 |
| Alkoxy-Py—PheX-Alkyl | I32 |
| Alkyl-Py—PheX—CN | I33 |
| Alkoxy-Py—PheX-Alkyl | I34 |
| Alkyl-Py—CH₂CH₂—PheX-Alkoxy | I35 |
| Alkyl-Py—CH₂CH₂—Phe-Alkoxy | I36 |
| Alkyl-Py—CH₂CH₂—Phe—Phe-Alkoxy | I37 |
| Alkyl-Py—CH₂CH₂—PheX—Phe-Alkoxy | I38 |
| Alkyl-Py—Phe—PheX-Alkyl | I39 |
| Alkyl-Py—Phe—OCO—PheX-Alkyl | I40 |
| Alkyl-PheX—Py—Cy-Alkyl | I41 |

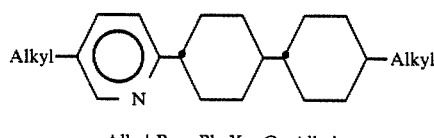

Alkyl-Py—PheX—Cy-Alkyl    I43

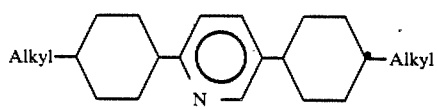

| | |
|---|---|
| Alkyl-Phe—Py—CH₂CH₂—PheX-Alkyl | I45 |
| Alkyl-Py—Phe—CH₂CH₂—PheX-Alkyl | I46 |
| Alkyl-Py—Phe—CH₂CH₂—PheX-Alkoxy | I47 |
| Alkyl-Cy—Py—CH₂CH₂—Cy-Alkyl | I48 |
| Alkyl-Cy—Py—OCO—Cy-Alkyl | I49 |
| Alkyl-Py—Py—CH₂CH₂—Cy-Alkyl | I50 |
| Alkoxy-Py—Cy—CH₂CH₂—Cy-Alkyl | I51 |
| Alkyl-Py—Cy—OCH₂—Cy-Alkyl | I52 |

-continued

| | |
|---|---|
| Alkyl-Py—Cy—Cy—Cy-Alkyl | I53 |
| Alkyl-Py—Cy—Cy—Phe-Alkoxy | I54 |
| Alkyl-Cy—Py—OCO—Phe—Phe-Alkyl | I55 |
| Alkyl-Py—CH₂CH₂—Phe—Cy—Cy-Alkyl | I56 |
| Alkyl-Py—Cy—CH₂CH₂—Cy—Cy-Alkyl | I57 |
| Alkyl-Cy—Py—Cy—Cy-Alkyl | I58 |
| Alkyl-Cy—COO—Py—Phe—Phe-Alkyl | I59 |
| Alkyl-Cy—Py—CH₂CH₂—Phe—Phe-Alkyl | I60 |
| Alkyl-Py—OCH₂—Phe—Cy—Cy-Alkyl | I61 |
| Alkoxy-Phe—Py—CH₂CH₂—Cy—Phe-Alkyl | I62 |
| Alkyl-Phe—Py—OCO—Cy—Cy-Alkyl | I63 |
| Alkyl-Phe—Py—Cy—COO—Phe-Alkyl | I64 |

I65

[structure with three rings: cyclohexyl-phenyl(N)-phenyl, with F substituent]

I66

[structure: Alkyl-Phe-N-ring—CH₂CH₂—Cy-Alkyl]

I67

[structure: Alkyl-Phe-N-ring—CH₂CH₂—Cy-Alkyl]

I68

[structure: Alkyl-Phe-N-ring—Phe—Alkyl]

In the foregoing formulae I1 to I68, alkyl is preferably an alkyl group of 2 to 10 C atoms and alkoxy an alkoxy group of 2 to 12 C atoms. Preference is also given to compounds of the formulae I1 to I68 in which instead of alkoxy a 2-oxaalkyl group of 2 to 12 C atoms is present.

Of the compounds of the formula I, preference is given to those stereoisomers in which the saturated rings (for example Cy, Dio, Dit) are trans-1,4-disubstituted.

Those of the aforementioned formulae which contain one or more of the groups Dio and/or Dit comprise in each case the two possible 2,5-position isomers. Those of the aforementioned formulae in which one of the group Z¹ and/or Z² which is different from the single bond is linked to Pa or Py are preferred.

The compounds of the formula I are prepared in a conventional manner of the type described in the literature (for example in the standard works such as Houben-Weyl, Methoden der Organischen Chemie [Methods of Organic Chemistry], Georg-Thieme-Verlag, Stuttgart) under reaction conditions which are known and suitable for the reactions mentioned. In this it is also possible to make use of conventional variants not mentioned here.

The skilled worker can, through routine methods, find appropriate synthetic methods in the state of the art (for example German Offenlegungsschriften Nos. 2,344,732, 2,450,088, 2,429,093, 2,502,904, 2,636,684, 2,701,591 and 2,752,975 concerning compounds having 1,4-cyclohexylene and 1,4-phenylene groups; German Offenlegungsschriften Nos. 2,944,905 and 3,227,916 concerning compounds having 1,3-dioxane-2,5-diyl groups; DD 160,061 concerning compounds having 1,3-dithiane-2,5-diyl groups; U.S. Pat. Nos. 4,261,652 and 4,219,256 concerning compounds having 1,4-bicyclo(2,2,2)octylene groups; and German Offenlegungsschrift No. 3,201,721 concerning compounds having —CH$_2$CH$_2$— bridge members.

The starting materials can if desired also be formed in situ by not isolating them out of the reaction mixture but immediately reacting them further to form the compounds of the formula I.

For instance, the compounds of the formula I can be prepared by reducing a compound which otherwise conforms to the formula I but in place of H atoms con is one or more reducible groups and/or C—C bonds.

Suitable reducible groups are preferably carbonyl groups, in particular keto groups, and also, for example, free or esterified hydroxyl groups or aromatically bonded halogen atoms. Preferred starting materials for the reduction conform to the formula I but can contain in place of a cyclohexane ring a cyclohexene ring or cyclohexanone ring and/or in place of a —CH$_2$CH$_2$— group a —CH═CH— group and/or in place of a —CH$_2$— group a —CO— group and/or in place of an H atom a free or a functionally (for example in the form of its p-toluenesulfonate) modified OH group.

The reduction can be effected for example by catalytic hydrogenation at temperatures between about 0° and about 200° and at pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable catalysts are preferably noble metals such as Pt or Pd which can be used in the form of oxides (for example PtO$_2$, PdO), on a carrier (for example Pd on carbon, calcium carbonate or strontium carbonate) or in finely divided form.

Ketones can also be reduced by the methods of Clemmensen (with zinc, amalgamated zinc or tin and hydrochloric acid, preferably in aqueous alcoholic solution or in heterogeneous phase with water/toluene at temperatures between about 80° and 120° C.) or Wolff-Kishner (with hydrazine, preferably in the presence of alkali such as KOH or NaOH in a high-boiling solvent such as diethylene glycol or triethylene glycol at temperatures between about 100° and 200° C.) to the corresponding compounds of the formula I which contain alkyl groups and/or —CH$_2$CH$_2$— bridges.

Reductions are also possible with complex hydrides. For example, arylsulfonyloxy groups can be reductively removed with LiAlH$_4$, in particular p-toluenesulfonyloxymethyl groups can be reduced to methyl groups, preferably in an inert solvent such as diethyl ether or THF at temperatures between about 0° and 100° C. Double bonds can (even in the presence of CN groups!) be hydrogenated with NaBH$_4$ or tributyltin hydride in methanol.

Esters of the formula I (R$^1$ and/or R$^2$═alkyl wherein one or two CH$_2$ groups have been replaced by —O—CO— and/or —CO—O— groups and/or Z$^1$ and/or Z$^2$═—CO—O— or —O—CO—) can also be obtained by esterifying corresponding carboxylic acids (or their reactive derivatives) with alcohols or phenols (or their reactive derivatives).

Suitable reactive derivatives of the carboxylic acids mentioned are in particular the acid halides, above all the chlorides and bromides, together with the anhydrides, azides or esters, in particular alkyl esters having 1-4 C atoms in the alkyl group.

Suitable reactive derivatives of the alcohols and phenols mentioned are in particular the corresponding metal alcoholates and phenolates, preferably of an alkali metal such as Na or K.

The esterification is advantageously carried out in the presence of an inert solvent. Highly suitable are in particular ethers such as diethyl ether, di-n-butyl ether, THF, dioxane or anisole, ketones such as acetone, butanone or cyclohexanone, amides such as DMF or hexamethylphosphoramide, hydrocarbons such as benzene, toluene or xylene, halohydrocarbons such as carbon tetrachloride or tetrachloroethylene and sulfoxides such as dimethyl sulfoxide or sulfolane. Water-immiscible solvents can at the same time be advantageously used for removing by azeotropic distillation the water formed in the course of the esterification. Occasionally it can also be possible to employ an excess of an organic base, for example pyridine, quinoline or triethylamine, as solvent for the esterification. The esterification can also be carried out in the absence of a solvent, for example by simply heating the components in the presence of sodium acetate. The reaction temperature is customarily between −50° and +250°, preferably between −20° and +80°. At these temperatures the esterification reactions are generally complete within 15 minutes to 48 hours.

In detail, the reaction conditions for the esterification depend substantially on the nature of the starting materials used. For instance, a free carboxylic acid is in general reacted with a free alcohol or phenol in the presence of a strong acid, for example a mineral acid such as hydrochloric acid or sulfuric acid. A preferred reaction is the reaction of an acid anhydride or in particular of an acid chloride with an alcohol, preferably in a basic medium, suitable bases being in particular alkali metal hydroxides such as sodium hydroxide or potassium hydroxide, alkali metal carbonates and hydrogencarbonates such as sodium carbonate, sodium hydrogencarbonate, potassium carbonate or potassium hydrogencarbonate, alkali metal acetates, such as sodium acetate or potassium acetate, alkaline earth metal hydroxides such as calcium hydroxide or organic bases such as triethylamine, pyridine, lutidine, collidine or quinoline. A further preferred embodiment of the esterification comprises converting the alcohol or phenol first into the sodium or potassium alcoholate or phenolate, for example by treatment with ethanolic sodium hydroxide or potassium hydroxide solution, isolating the alcoholate or phenolate and suspending it together with sodium hydrogencarbonate or potassium carbonate with stirring in acetone or diethyl ether, and adding to this suspension a solution of the acid chloride or anhydride in diethyl ether, acetone or DMF, preferably at temperatures between about −25° and +20°.

Dioxane derivatives and dithiane derivatives of the formula I (wherein one of the groups A$^1$ and/or A$^2$ and/or A$^3$ is a 1,3-dioxane-2,5-diyl group or a 1,3-dithiane-2,5-diyl group respectively) are preferably prepared by reacting a corresponding aldehyde with a corresponding 1,3-diol or a corresponding 1,3-dithiol (or one of its reactive derivatives), preferably in the presence of an inert solvent such as benzene or toluene and/or of a catalyst, for example of a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

The abovementioned aldehydes, 1,3-diols and 1,3-dithiols as well as their reactive derivatives are partly known, partly preparable without difficulties by standard methods of organic chemistry from compounds described in the literature. For example, the aldehydes are obtainable by oxidizing corresponding alcohols or by reducing corresponding carboxylic acids or their derivatives, the diols by reducing corresponding diesters, and the dithiols by reacting corresponding dihalides with NaSH.

To prepare nitriles of the formula I (wherein $R^1$ or $R^2$ is CN), corresponding acid amides can be dehydrated. The amides are obtainable for example from corresponding esters or acid halides by reaction with ammonia. Suitable water-eliminating agents are for example inorganic acid chlorides such as $SOCl_2$, $PCl_3$, $PCl_5$, $POCl_3$, $SO_2Cl_2$, $COCl_2$ and also $P_2O_5$, $P_2S_5$, $AlCl_3$ (for example as double compound with NaCl), aromatic sulfonic acids and sulfonyl halides. This reaction can be carried out in the presence or absence of an inert solvent at temperatures between about 0° and 150°; suitable solvents are for example bases such as pyridine or triethylamine, aromatic hydrocarbons such as benzene, toluene or xylene or amides such as DMF.

To prepare the aforementioned nitriles of the formula I it is also possible to react corresponding acid halides, preferably the chlorides, with sulfamide, preferably in an inert solvent such as tetramethylene sulfone at temperatures between about 80° and 150°, preferably at 120°. By customary working up it is possible to isolate the nitriles directly.

Ethers of the formula I (wherein $R^1$ and/or $R^2$ is an alkyl group, wherein one or two $CH_2$ groups are replaced by 0 atoms and/or wherein $Z^1$ and/or $Z^2$ is an —$OCH_2$— or a —$CH_2O$— group) are obtainable by etherifying corresponding hydroxy compounds, preferably corresponding phenols, the hydroxy compound preferably being first converted into a corresponding metal derivative, for example by treatment with NaH, $NaNH_2$, NaOH, KOH, $Na_2CO_3$ or $K_2CO_3$ into the corresponding alkali metal alcoholate or alkali metal phenolate. This alcoholate or phenolate can then be reacted with the corresponding alkyl halide, alkylsulfonate or dialkylsulfonate, preferably in an inert solvent such as acetone, 1,2-dimethoxyethane, DMF or dimethyl sulfoxide or even an excess of aqueous or aqueous alcoholic NaOH or KOH at temperatures between about 20° and 100°.

To prepare nitriles of the formula I (wherein $R^1$ or $R^2$ is CN and/or $A^1$ and/or $A^2$ and/or $A^3$ is substituted by at least one CN group) it is also possible to react corresponding chlorine or bromine compounds of the formula I with a cyanide, preferably with a metal cyanide such as NaCN, KCN or $Cu_2(CN)_2$, for example in the presence of pyridine in an inert solvent such as DMF or N-methylpyrrolidone at temperatures between 20° and 200°.

To prepare laterally substituted fluorine or chlorine compounds of the formula I (wherein $A^1$ and/or $A^2$ and/or $A^3$ are aromatics, and $R^1$ and $R^2$ can have the customary meanings), corresponding amino compounds (obtainable by reducing the corresponding nitro compounds by standard methods, for example by catalytic hydrogenation, by treatment with aqueous dithionite or with tin(II) chloride and hydrochloric acid) can be reacted with sodium nitrite and either with tetrafluoroboric acid (to introduce an F atom) or with copper(I) chloride (to introduce a Cl atom) to form the diazonium salts which are then thermally decomposed at temperatures of 100°–250°.

A base of the formula I can be converted with an acid into the corresponding acid addition salt. This reaction can be performed with inorganic acids, for example sulfuric acid, nitric acid, hydrohalic acid such as hydrochloric acid or hydrobromic acid, phosphoric acids such as orthophosphoric acid, sulfamic acid, and also organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid.

Conversely it is possible to free the base of the formula I from an acid addition salt of a compound of the formula I by treatment with a base, for example with a strong inorganic base such as KOH or NaOH.

The liquid-crystalline phases according to the invention consist of 2 to 15, preferably 3 to 12, components, including at least one compound of the formula I. The other constituents are preferably selected from the nematic or nematogenic substances, in particular the known substances, of the classes of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines, cyclohexylpyrimidines, phenyldioxanes, cyclohexyldioxanes, phenyl- or cyclohexyl-1,3-dithianes, 1-phenyl-2-cyclohexylethanes, optionally halogenated stilbenes, benzyl phenyl ethers, tolanes and substituted cinnamic acids.

The most important compounds suitable for use as constituents of such liquid-crystalline phases can be characterized by the formula II

   II wherein L and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene and tetrahydronaphthalene, quinazoline and tetrahydroquinazoline, G is

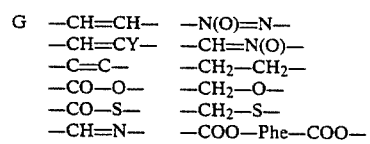

or a C—C single bond, Y is halogen, preferably chlorine, or CN, and R' and R" are alkyl, alkoxy, alkanoyloxy or alkoxycarbonyloxy having up to 18, preferably up to 8, carbon atoms, or one of these radicals is also CN, NC, $NO_2$, $CH_3$, F, Cl or Br.

In most of these compounds, R' and R" differ from each other, one of these radicals usually being an alkyl or alkoxy group. But other variants of the proposed substituents are also customary. Many such substances or even mixtures thereof are commercially available. All these substances are preparable by literature methods.

The phases according to the invention contain about 0.1 to 99%, preferably 10 to 95%, of one or more compounds of the formula I.

Preference is further given to dielectrics according to the invention which contain 0.1 to 40%, preferably 0.5 to 30%, of one or more compounds of the formula I.

The dielectrics according to the invention are prepared in a conventional manner. In general the components are dissolved in one another, preferably at elevated temperature.

By means of suitable additives the liquidcrystalline dielectrics according to the invention can be modified in such a way that they can be used in all hitherto disclosed types of liquid crystal display elements.

Such additives are known to the skilled worker and are exhaustively described in the literature. It is possible to add for example conducting salts, preferably ethyldimethyldodecylammonium 4-hexyloxybenzoate, tetrabutylammonium tetraphenylboranate or complex salts of crown ethers (cf. for example I. Haller et al., Mol. Cryst. Liq. Cryst. Volume 24, pages 249–258 (1973)) to improve the conductivity, dichroic dyes to produce colored guest-host systems or substances to modify the dielectric anisotropy, the viscosity and/or the orientation of the nematic phases. Such substances are described for example in German Offenlegungsschriften Nos. 2,209,127, 2,240,854, 2,321,632, 2,338,281, 2,450,088, 2,637,430, 2,853,728 and 2,902,177.

The examples which follow serve to illustrate the invention without limiting it. C, S, Ch, N and I denote crystalline, smectic, cholesteric, nematic and isotropic state. The numbers in between represent the transition temperatures. m.p.=melting point. Heretofore and hereinafter percentages are per cent by weight; all temperatures are given in degrees celsius. "Customary working up" is: adding water, extracting with methylene chloride, separating off, drying the organic phase, evaporating and purifying the product by crystallization and/or chromatography.

EXAMPLE 1

A mixture of 11 g of 2-p-hydroxyphenyl-5-n-hexylpyrazine, 7.8 g of trans-4-n-propyl-1-bromomethylcyclohexane, 8.6 g of potassium carbonate and 50 ml of dimethylformamide is heated at 90° for 10 hours. Customary working up gives 4-(5-n-hexylpyrazin-2-yl)-phenyl trans-4-n-propylcyclohexylmethyl ether.

Prepared analogously:
4-(5-Hexylpyrazin-2-yl)-phenyl trans-4-ethylcyclohexylmethyl ether
4-(5-Hexylpyrazin-2-yl)-phenyl trans-4-butylcyclohexylmethyl ether
4-(5-Hexylpyrazin-2-yl)-phenyl trans-4-pentylcyclohexylmethyl ether
4-(5-Hexylpyrazin-2-yl)-phenyl trans-4-heptylcyclohexylmethyl ether
4-(5-Heptylpyrazin-2-yl)-phenyl trans-4-ethylcyclohexylmethyl ether
4-(5-Heptylpyrazin-2-yl)-phenyl trans-4-propylcyclohexylmethyl ether
4-(5-Heptylpyrazin-2-yl)-phenyl trans-4-butylcyclohexylmethyl ether
4-(5-Heptylpyrazin-2-yl)-phenyl trans-4-pentylcyclohexylmethyl ether
4-(5-Heptylpyrazin-2-yl)-phenyl trans-4-heptylcyclohexylmethyl ether
4-(5-Nonylpyrazin-2-yl)-phenyl trans-4-ethylcyclohexylmethyl ether
4-(5-Nonylpyrazin-2-yl)-phenyl trans-4-propylcyclohexylmethyl ether
4-(5-Nonylpyrazin-2-yl)-phenyl trans-4-butylcyclohexylmethyl ether
4-(5-Nonylpyrazin-2-yl)-phenyl trans-4-pentylcyclohexylmethyl ether
4-(5-Nonylpyrazin-2-yl)-phenyl trans-4-heptylcyclohexylmethyl ether
4-(5-Pentylpyrazin-2-yl)-phenyl trans-4-ethylcyclohexylmethyl ether
4-(5-Pentylpyrazin-2-yl)-phenyl trans-4-propylcyclohexylmethyl ether
4-(5-Pentylpyrazin-2-yl)-phenyl trans-4-butylcyclohexylmethyl ether
4-(5-Pentylpyrazin-2-yl)-phenyl trans-4-pentylcyclohexylmethyl ether
4-(5-Pentylpyrazin-2-yl)-phenyl trans-4-heptylcyclohexylmethyl ether
4-(5-Propylpyrazin-2-yl)-phenyl trans-4-ethylcyclohexylmethyl ether
(5-Propylpyrazin-2-yl)-phenyl trans-4-propylcyclohexylmethyl ether
(5-Propylpyrazin-2-yl)-phenyl trans-4-butylcyclohexylmethyl ether
4-(5-Propylpyrazin-2-yl)-phenyl trans-4-pentylcyclohexylmethyl ether
4-(5-Propylpyrazin-2-yl)-phenyl trans-4-heptylcyclohexylmethyl ether.

Etherification produces analogously the following corresponding pyridine compounds:
4-(5-Hexylpyridin-2-yl)-phenyl trans-4-ethylcyclohexylmethyl ether
4-(5-Hexylpyridin-2-yl)-phenyl trans-4-propylcyclohexylmethyl ether
4-(5-Hexylpyridin-2-yl)-phenyl trans-4-butylcyclohexylmethyl ether
4-(5-Hexylpyridin-2-yl)-phenyl trans-4-pentylcyclohexylmethyl ether
4-(5-Hexylpyridin-2-yl)-phenyl trans-4-hexylcyclohexylmethyl ether
4-(5-Hexylpyridin-2-yl)-phenyl trans-4-heptylcyclohexylmethyl ether
4-(5-Heptylpyridin-2-yl)-phenyl trans-4-ethylcyclohexylmethyl ether
4-(5-Heptylpyridin-2-yl)-phenyl trans-4-propylcyclohexlmethyl ether
4-(5-Heptylpyridin-2-yl)-phenyl trans-4-butylcyclohexylmethyl ether
4-(5-Heptylpyridin-2-yl)-phenyl trans-4-pentylcyclohexylmethyl ether
4-(5-Heptylpyridin-2-yl)-phenyl trans-4-hexylcyclohexylmethyl ether
4-(5-Heptylpyridin-2-yl)-phenyl trans-4-heptylcyclohexylmethyl ether
4-(5-Nonylpyridin-2-yl)-phenyl trans-4-ethylcyclohexylmethyl ether
4-(5-Nonylpyridin-2-yl)-phenyl trans-4-propylcyclohexylmethyl ether
4-(5-Nonylpyridin-2-yl)-phenyl trans-4-butylcyclohexylmethyl ether 4-(5-Nonylpyridin-2-yl)-phenyl trans-4-pentylcyclohexylmethyl ether
4-(5-Nonylpyridin-2-yl)-phenyl trans-4-hexylcyclohexylmethyl ether
4-(5-Nonylpyridin-2-yl)-phenyl trans-4-heptylcyclohexylmethyl ether
4-(5-Pentylpyridin-2-yl)-phenyl trans-4-ethylcyclohexylmethyl ether
4-(5-Pentylpyridin-2-yl)-phenyl trans-4-propylcyclohexylmethyl ether
4-(5-Pentylpyridin-2-yl)-phenyl trans-4-butylcyclohexylmethyl ether
4-(5-Pentylpyridin-2-yl)-phenyl trans-4-pentylcyclohexylmethyl ether
4-(5-Pentylpyridin-2-yl)-phenyl trans-4-hexylcyclohexylmethyl ether
4-(5-Pentylpyridin-2-yl)-phenyl trans-4-heptylcyclohexylmethyl ether
4-(5-Propylpyridin-2-yl)-phenyl trans-4-ethylcyclohexylmethyl ether
4-(5-Propylpyridin-2-yl)-phenyl trans-4-propylcyclohexylmethyl ether
4-(5-Propylpyridin-2-yl)-phenyl trans-4-butylcyclohexylmethyl ether
4-(5-Propylpyridin-2-yl)-phenyl trans-4-pentylcyclohexylmethyl ether
4-(5-Propylpyridin-2-yl)-phenyl trans-4-hexylcyclohexylmethyl ether
4-(5-Propylpyridin-2-yl)-phenyl trans-4-heptylcyclohexylmethyl ether
4-(5-Butylpyridin-2-yl)-phenyl trans-4-ethylcyclohexylmethyl ether
4-(5-Butylpyridin-2-yl)-phenyl trans-4-propylcyclohexylmethyl ether
4-(5-Butylpyridin-2-yl)-phenyl trans-4-butylcyclohexylmethyl ether
4-(5-Butylpyridin-2-yl)-phenyl trans-4-pentylcyclohexylmethyl ether
4-(5-Butylpyridin-2-yl)-phenyl trans-4-hexylcyclohexylmethyl ether
4-(5-Butylpyridin-2-yl)-phenyl trans-4-heptylcyclohexylmethyl ether

EXAMPLE 2

A mixture of 10.4 g of 5-(4-pentylphenyl)-2-pyrazinol (obtainable analogously to Japanese Preliminary Published Application 144,770/84), 7.7 g of p-n-propylbenzyl bromide, 8.6 g of potassium carbonate and 50 ml of dimethylformamide is heated at 90° for 10 hours. Customary working up gives 5-(4-n-pentylphenyl)-pyrazin-2-yl p-n-propylbenzyl ether.
Prepared analogously:
5-(4-n-Pentylphenyl)-pyrazin-2-yl (p-ethylbenzyl) ether
5-(4-n-Pentylphenyl)-pyrazin-2-yl (p-butylbenzyl) ether
5-(4-n-Pentylphenyl)-pyrazin-2-yl (p-pentylbenzyl) ether
5-(4-n-Pentylphenyl)-pyrazin-2-yl (p-hexylbenzyl) ether
5-(4-n-Pentylphenyl)-pyrazin-2-yl (p-heptylbenzyl) ether
5-(4-n-Pentylphenyl)-pyrazin-2-yl (p-octylbenzyl) ether
5-(4-Ethylphenyl)-pyrazin-2-yl (p-ethylbenzyl) ether
5-(4-Ethylphenyl)-pyrazin-2-yl (p-propylbenzyl) ether
5-(4-Ethylphenyl)-pyrazin-2-yl (p-butylbenzyl) ether
5-(4-Ethylphenyl)-pyrazin-2-yl (p-pentylbenzyl) ether
5-(4-Ethylphenyl)-pyrazin-2-yl (p-hexylbenzyl) ether
5-(4-Ethylphenyl)-pyrazin-2-yl (p-heptylbenzyl) ether
5-(4-Ethylphenyl)-pyrazin-2-yl (p-octylbenzyl) ether
5-(4-Propylphenyl)-pyrazin-2-yl (p-ethylbenzyl) ether
5-(4-Propylphenyl)-pyrazin-2-yl (p-propylbenzyl) ether
5-(4-Propylphenyl)-pyrazin-2-yl (p-butylbenzyl) ether
5-(4-Propylphenyl)-pyrazin-2-yl (p-pentylbenzyl) ether
5-(4-Propylphenyl)-pyrazin-2-yl (p-hexylbenzyl) ether
5-(4-Propylphenyl)-pyrazin-2-yl (p-heptylbenzyl) ether
5-(4-Propylphenyl)-pyrazin-2-yl (p-octylbenzyl) ether
5-(4-Hexylphenyl)-pyrazin-2-yl (p-ethylbenzyl) ether
5-(4-Hexylphenyl)-pyrazin-2-yl (p-propylbenzyl) ether
5-(4-Hexylphenyl)-pyrazin-2-yl (p-butylbenzyl) ether
5-(4-Hexylphenyl)-pyrazin-2-yl (p-pentylbenzyl) ether
5-(4-Hexylphenyl)-pyrazin-2-yl (p-hexylbenzyl) ether
5-(4-Hexylphenyl)-pyrazin-2-yl (p-heptylbenzyl) ether
5-(4-Hexylphenyl)-pyrazin-2-yl (p-octylbenzyl) ether
5-(4-Heptylphenyl)-pyrazin-2-yl (p-ethylbenzyl) ether
5-(4-Heptylphenyl)-pyrazin-2-yl (p-propylbenzyl) ether
5-(4-Heptylphenyl)-pyrazin-2-yl (p-butylbenzyl) ether
5-(4-Heptylphenyl)-pyrazin-2-yl (p-pentylbenzyl) ether
5-(4-Heptylphenyl)-pyrazin-2-yl (p-hexylbenzyl) ether
5-(4-Heptylphenyl)-pyrazin-2-yl (p-heptylbenzyl) ether
5-(4-Heptylphenyl)-pyrazin-2-yl (p-octylbenzyl) ether
5-(4-Nonylphenyl)-pyrazin-2-yl (p-ethylbenzyl) ether
5-(4-Nonylphenyl)-pyrazin-2-yl (p-propylbenzyl) ether
5-(4-Nonylphenyl)-pyrazin-2-yl (p-butylbenzyl) ether
5-(4-Nonylphenyl)-pyrazin-2-yl (p-pentylbenzyl) ether
5-(4-Nonylphenyl)-pyrazin-2-yl (p-hexylbenzyl) ether
5-(4-Nonylphenyl)-pyrazin-2-yl (p-heptylbenzyl) ether
5-(4-Nonylphenyl)-pyrazin-2-yl (p-octylbenzyl) ether.

EXAMPLE 3

16.4 g of 4-propyl benzoic acid are boiled for hour with 24 g of SOCl$_2$, which is followed by evaporating, dissolving the acid chloride obtained in 150 ml of toluene, adding 8 ml of pyridine and 24.2 g of 5-(4-pentylphenyl)-2-pyrazinol (obtainable analogously to Japanese Preliminary Published Application 144,770/84) and boiling for 2 hours. Cooling down and customary working up gives 5-(4-pentylphenyl)-pyrazin-2-yl 4-propylbenzoate.
Analogously obtained by esterifying the corresponding acids:
5-(4-Pentylphenyl)-pyrazin-2-yl 4-ethylbenzoate
5-(4-Pentylphenyl)-pyrazin-2-yl 4-butylbenzoate
5-(4-Pentylphenyl)-pyrazin-2-yl 4-pentylbenzoate
5-(4-Pentylphenyl)-pyrazin-2-yl 4-hexylbenzoate
5-(4-Pentylphenyl)-pyrazin-2-yl 4-heptylbenzoate
5-(4-Pentylphenyl)-pyrazin-2-yl 4-octylbenzoate
5-(4-Pentylphenyl)-pyrazin-2-yl 4-nonylbenzoate
5-(4-Pentylphenyl)-pyrazin-2-yl 2-fluoro-4-ethylbenzoate
5-(4-Pentylphenyl)-pyrazin-2-yl 2-fluoro-4-propylbenzoate
5-(4-Pentylphenyl)-pyrazin-2-yl 2-fluoro-4-butylbenzoate
5-(4-Pentylphenyl)-pyrazin-2-yl 2-fluoro-4-pentylbenzoate
5-(4-Pentylphenyl)-pyrazin-2-yl 2-fluoro-4-hexylbenzoate
5-(4-Pentylphenyl)-pyrazin-2-yl 2-fluoro-4-heptylbenzoate
5-(4-Pentylphenyl)-pyrazin-2-yl 2-fluoro-4-octylbenzoate
5-(4-Pentylphenyl)-pyrazin-2-yl 2-fluoro-4-nonylbenzoate
5-(4-Ethylphenyl)-pyrazin-2-yl 4-ethylbenzoate
5-(4-Ethylphenyl)-pyrazin-2-yl 4-propylbenzoate
5-(4-Ethylphenyl)-pyrazin-2-yl 4-butylbenzoate
5-(4-Ethylphenyl)-pyrazin-2-yl 4-pentylbenzoate
5-(4-Ethylphenyl)-pyrazin-2-yl 4-hexylbenzoate 5-(4-Ethylphenyl)-pyrazin-2-yl 4-heptylbenzoate
5-(4-Ethylphenyl)-pyrazin-2-yl 4-octylbenzoate
5-(4-Ethylphenyl)-pyrazin-2-yl 4-nonylbenzoate
5-(4-Ethylphenyl)-pyrazin-2-yl 2-fluoro-4-ethylbenzoate
5-(4-Ethylphenyl)-pyrazin-2-yl 2-fluoro-4-propylbenzoate
5-(4-Ethylphenyl)-pyrazin-2-yl 2-fluoro-4-butylbenzoate
5-(4-Ethylphenyl)-pyrazin-2-yl 2-fluoro-4-pentylbenzoate
5-(4-Ethylphenyl)-pyrazin-2-yl 2-fluoro-4-hexylbenzoate
5-(4-Ethylphenyl)-pyrazin-2-yl 2-fluoro-4-heptylbenzoate
5-(4-Ethylphenyl)-pyrazin-2-yl 2-fluoro-4-octylbenzoate
5-(4-Ethylphenyl)-pyrazin-2-yl 2-fluoro-4-nonylbenzoate
5-(4-Propylphenyl)-pyrazin-2-yl 4-ethylbenzoate
5-(4-Propylphenyl)-pyrazin-2-yl 4-propylbenzoate
5-(4-Propylphenyl)-pyrazin-2-yl 4-butylbenzoate
5-(4-Propylphenyl)-pyrazin-2-yl 4-pentylbenzoate
5-(4-Propylphenyl)-pyrazin-2-yl 4-hexylbenzoate
5-(4-Propylphenyl)-pyrazin-2-yl 4-heptylbenzoate
5-(4-Propylphenyl)-pyrazin-2-yl 4-octylbenzoate
5-(4-Propylphenyl)-pyrazin-2-yl 4-nonylbenzoate
5-(4-Propylphenyl)-pyrazin-2-yl 2-fluoro-4-ethylbenzoate
5-(4-Propylphenyl)-pyrazin-2-yl 2-fluoro-4-propylbenzoate
5-(4-Propylphenyl)-pyrazin-2-yl 2-fluoro-4-butylbenzoate
5-(4-Propylphenyl)-pyrazin-2-yl 2-fluoro-4-pentylbenzoate
5-(4-Propylphenyl)-pyrazin-2-yl 2-fluoro-4-hexylbenzoate
5-(4-Propylphenyl)-pyrazin-2-yl 2-fluoro-4-heptylbenzoate
5-(4-Propylphenyl)-pyrazin-2-yl 2-fluoro-4-octylbenzoate
5-(4-Propylphenyl)-pyrazin-2-yl 2-fluoro-4-nonylbenzoate
5-(4-Butylphenyl)-pyrazin-2-yl 4-ethylbenzoate
5-(4-Butylphenyl)-pyrazin-2-yl 4-propylbenzoate
5-(4-Butylphenyl)-pyrazin-2-yl 4-butylbenzoate
5-(4-Butylphenyl)-pyrazin-2-yl 4-pentylbenzoate
5-(4-Butylphenyl)-pyrazin-2-yl 4-hexylbenzoate
5-(4-Butylphenyl)-pyrazin-2-yl 4-heptylbenzoate
5-(4-Butylphenyl)-pyrazin-2-yl 4-octylbenzoate
5-(4-Butylphenyl)-pyrazin-2-yl 4-nonylbenzoate
5-(4-Butylphenyl)-pyrazin-2-yl 2-fluoro-4-ethylbenzoate
5-(4-Butylphenyl)-pyrazin-2-yl 2-fluoro-4-propylbenzoate
5-(4-Butylphenyl)-pyrazin-2-yl 2-fluoro-4-butylbenzoate
5-(4-Butylphenyl)-pyrazin-2-yl 2-fluoro-4-pentylbenzoate
5-(4-Butylphenyl)-pyrazin-2-yl 2-fluoro-4-hexylbenzoate
5-(4-Butylphenyl)-pyrazin-2-yl 2-fluoro-4-heptylbenzoate
5-(4-Butylphenyl)-pyrazin-2-yl 2-fluoro-4-octylbenzoate
5-(4-Butylphenyl)-pyrazin-2-yl 2-fluoro-4-nonylbenzoate
5-(4-Hexylphenyl)-pyrazin-2-yl 4-ethylbenzoate
5-(4-Hexylphenyl)-pyrazin-2-yl 4-propylbenzoate
5-(4-Hexylphenyl)-pyrazin-2-yl 4-butylbenzoate
5-(4-Hexylphenyl)-pyrazin-2-yl 4-pentylbenzoate
5-(4-Hexylphenyl)-pyrazin-2-yl 4-hexylbenzoate
5-(4-Hexylphenyl)-pyrazin-2-yl 4-heptylbenzoate
5-(4-Hexylphenyl)-pyrazin-2-yl 4-octylbenzoate
5-(4-Hexylphenyl)-pyrazin-2-yl 4-nonylbenzoate
5-(4-Hexylphenyl)-pyrazin-2-yl 2-fluoro-4-ethylbenzoate
5-(4-Hexylphenyl)-pyrazin-2-yl 2-fluoro-4-propylbenzoate
5-(4-Hexylphenyl)-pyrazin-2-yl 2-fluoro-4-butylbenzoate
5-(4-Hexylphenyl)-pyrazin-2-yl 2-fluoro-4-pentylbenzoate
5-(4-Hexylphenyl)-pyrazin-2-yl 2-fluoro-4-hexylbenzoate
5-(4-Hexylphenyl)-pyrazin-2-yl 2-fluoro-4-heptylbenzoate
5-(4-Hexylphenyl)-pyrazin-2-yl 2-fluoro-4-octylbenzoate
5-(4-Hexylphenyl)-pyrazin-2-yl 2-fluoro-4-nonylbenzoate
5-(4-Propylphenyl)-pyrazin-2-yl 4-methoxybenzoate
5-(4-Butylphenyl)-pyrazin-2-yl 4-methoxybenzoate
5-(4-Pentylphenyl)-pyrazin-2-yl 4-methoxybenzoate
5-(4-Hexylphenyl)-pyrazin-2-yl 4-methoxybenzoate
5-(4-Heptylphenyl)-pyrazin-2-yl 4-methoxybenzoate
5-(4-Propylphenyl)-pyrazin-2-yl 4-ethoxybenzoate
5-(4-Butylphenyl)-pyrazin-2-yl 4-ethoxybenzoate
5-(4-Pentylphenyl)-pyrazin-2-yl 4-ethoxybenzoate
5-(4-Hexylphenyl)-pyrazin-2-yl 4-ethoxybenzoate
5-(4-Heptylphenyl)-pyrazin-2-yl 4-ethoxybenzoate
5-(4-Propylphenyl)-pyrazin-2-yl 4-propoxybenzoate
5-(4-Butylphenyl)-pyrazin-2-yl 4-propxybenzoate
5-(4-Pentylphenyl)-pyrazin-2-yl 4-propoxybenzoate
5-(4-Hexylphenyl)-pyrazin-2-yl 4-propoxybenzoate
5-(4-Heptylphenyl)-pyrazin-2-yl 4-propoxybenzoate
5-(4-Propylphenyl)-pyrazin-2-yl 4-butoxybenzoate
5-(4-Butylphenyl)-pyrazin-2-yl 4-butoxybenzoate
5-(4-Pentylphenyl)-pyrazin-2-yl 4-butoxybenzoate
5-(4-Hexylphenyl)-pyrazin-2-yl 4-butoxybenzoate
5-(4-Heptylphenyl)-pyrazin-2-yl 4-butoxybenzoate
5-(4-Cyanophenyl)-pyrazin-2-yl 4-ethylbenzoate
5-(4-Cyanophenyl)-pyrazin-2-yl 4-propylbenzoate
5-(4-Cyanophenyl)-pyrazin-2-yl 4-butylbenzoate
5-(4-Cyanophenyl)-pyrazin-2-yl 4-pentylbenzoate
5-(4-Cyanophenyl)-pyrazin-2-yl 4-hexylbenzoate
5-(4-Cyanophenyl)-pyrazin-2-yl 4-heptylbenzoate
5-(4-Cyanophenyl)-pyrazin-2-yl 4-octylbenzoate
5-(4-Cyanophenyl)-pyrazin-2-yl 4-nonylbenzoate.

EXAMPLE 4

Example 2 is repeated to convert 5-(4-cyanophenyl)-2-pyrazinol (obtainable according to Japanese Preliminary Published Application 144,772/1984) and p-n-propylbenzyl bromide into 5-(4-cyanophenyl)-pyrazin-2-yl p-n-propylbenzyl ether.

Prepared analogously:
5-(4-Cyanophenyl)-pyrazin-2-yl p-ethylbenzyl ether
5-(4-Cyanophenyl)-pyrazin-2-yl p-butylbenzyl ether
5-(4-Cyanophenyl)-pyrazin-2-yl p-pentylbenzyl ether
5-(4-Cyanophenyl)-pyrazin-2-yl p-hexylbenzyl ether
5-(4-Cyanophenyl)-pyrazin-2-yl p-heptylbenzyl ether
5-(4-Cyanophenyl)-pyrazin-2-yl p-octylbenzyl ether.

EXAMPLE 5

Example 2 is repeated to convert 5-(4-methoxyphenyl)-2-pyrazinol (preparable according to Japanese Preliminary Published Application 144,771/84) and p-n-propylbenzyl bromide into 5-(4-methoxyphenyl)-pyrazin-2-yl p-n-propylbenzyl ether.

Prepared analogously:
5-(4-Methoxyphenyl)-pyrazin-2-yl p-ethylbenzyl ether
5-(4-Methoxyphenyl)-pyrazin-2-yl p-butylbenzyl ether
5-(4-Methoxyphenyl)-pyrazin-2-yl p-pentylbenzyl ether
5-(4-Methoxyphenyl)-pyrazin-2-yl p-hexylbenzyl ether
5-(4-Methoxyphenyl)-pyrazin-2-yl p-heptylbenzyl ether
5-(4-Methoxyphenyl)-pyrazin-2-yl p-octylbenzyl ether
5-(4-Ethoxyphenyl)-pyrazin-2-yl p-ethylbenzyl ether
5-(4-Ethoxyphenyl)-pyrazin-2-yl p-propylbenzyl ether
5-(4-Ethoxyphenyl)-pyrazin-2-yl p-butylbenzyl ether
5-(4-Ethoxyphenyl)-pyrazin-2-yl p-pentylbenzyl ether
5-(4-Ethoxyphenyl)-pyrazin-2-yl p-hexylbenzyl ether
5-(4-Ethoxyphenyl)-pyrazin-2-yl p-heptylbenzyl ether
5-(4-Ethoxyphenyl)-pyrazin-2-yl p-octylbenzyl ether
5-(4-Propoxyphenyl)-pyrazin-2-yl p-ethylbenzyl ether
5-(4-Propoxyphenyl)-pyrazin-2-yl p-propylbenzyl ether
5-(4-Propoxyphenyl)-pyrazin-2-yl p-butylbenzyl ether
5-(4-Propoxyphenyl)-pyrazin-2-yl p-pentylbenzyl ether
5-(4-Propoxyphenyl)-pyrazin-2-yl p-hexylbenzyl ether
5-(4-Propoxyphenyl)-pyrazin-2-yl p-heptylbenzyl ether
5-(4-Propoxyphenyl)-pyrazin-2-yl p-octylbenzyl ether
5-(4-Butoxyphenyl)-pyrazin-2-yl p-ethylbenzyl ether
5-(4-Butoxyphenyl)-pyrazin-2-yl p-propylbenzyl ether
5-(4-Butoxyphenyl)-pyrazin-2-yl p-butylbenzyl ether
5-(4-Butoxyphenyl)-pyrazin-2-yl p-pentylbenzyl ether
5-(4-Butoxyphenyl)-pyrazin-2-yl p-hexylbenzyl ether
5-(4-Butoxyphenyl)-pyrazin-2-yl p-heptylbenzyl ether
5-(4-Butoxyphenyl)-pyrazin-2-yl p-octylbenzyl ether.

EXAMPLE 6

8.0 mmol of 5-[4-(2-methylbutoxy)-phenyl]-2-pyrazinol (known from Japanese Preliminary Published Application 92,276/'85) are added with stirring to a mixture of 7.0 mmol of 2-fluoro-4-octylbenzoyl chloride and 5 ml of pyridine and left to stand overnight. This gives optically active (S) 2-(2-fluoro-4-octylbenzoyloxy)-5-[4-(2-methylbutoxy)-phenyl]-pyrazine after extraction with toluene (30 ml) and water (20 ml), working up of the toluene phase and subsequent distillation.

The same method is used to prepare the following optically active compounds:
2-(2-Fluoro-4-ethylbenzoyloxy)-5-[4-(2-methylbutoxy)-phenyl]-pyrazine
2-(2-Fluoro-4-propylbenzoyloxy)-5-[4-(2-methylbutoxy)phenyl]-pyrazine
2-(2-Fluoro-4-butylbenzoyloxy)-5-[4-(2-methylbutoxy)-phenyl]-pyrazine
2-(2-Fluoro-4-pentylbenzoyloxy)-5-[4-(2-methylbutoxy)phenyl]-pyrazine
2-(2-Fluoro-4-hexylbenzoyloxy)-5-[4-(2-methylbutoxy)-phenyl]-pyrazine
2-(2-Fluoro-4-heptylbenzoyloxy)-5-[4-(2-methylbutoxy)phenyl]-pyrazine
2-(2-Fluoro-4-octylbenzoyloxy)-5-[4-(2-methylbutoxy)-phenyl]-pyrazine
2-(2-Fluoro-4-nonylbenzoyloxy)-5-[4-(2-methylbutoxy)phenyl]-pyrazine
2-(2-Fluoro-4-decylbenzoyloxy)-5-[4-(2-methylbutoxy)-phenyl]-pyrazine
2-(2-Fluoro-4-undecylbenzoyloxy)-5-[4-(2-methylbutoxy)phenyl]-pyrazine
2-(2-Fluoro-4-dodecylbenzoyloxy)-5-[4-(2-methylbutoxy)phenyl]-pyrazine
2-(2-Fluoro-4-ethoxybenzoyloxy)-5-[4-(2-methylbutoxy)phenyl]-pyrazine
2-(2-Fluoro-4-propoxybenzoyloxy)-5-[4-(2-methylbutoxy)phenyl]-pyrazine
2-(2-Fluoro-4-butoxybenzoyloxy)-5-[4-(2-methylbutoxy)phenyl]-pyrazine
2-(2-Fluoro-4-pentoxybenzoyloxy)-5-[4-(2-methylbutoxy)phenyl]-pyrazine
2-(2-Fluoro-4-hexoxybenzoyloxy)-5-[4-(2-methylbutoxy)phenyl]-pyrazine
2-(2-Fluoro-4-heptoxybenzoyloxy)-5-[4-(2-methylbutoxy)phenyl]-pyrazine
2-(2-Fluoro-4-octoxybenzoyloxy)-5-[4-(2-methylbutoxy)phenyl]-pyrazine
2-(2-Fluoro-4-nonoxybenzoyloxy)-5-[4-(2-methylbutoxy)phenyl]-pyrazine
2-(2-Fluoro-4-decoxybenzoyloxy)-5-[4-(2-methylbutoxy)phenyl]-pyrazine
2-(2-Fluoro-4-undecoxybenzoyloxy)-5-[4-(2-methylbutoxy)phenyl]-pyrazine
2-(2-Fluoro-4-dodecoxybenzoyloxy)-5-[4-(2-methylbutoxy)phenyl]-pyrazine.

EXAMPLE 7

Example 3 is repeated to obtain from 4-(5-pentylpyridin-2-yl)-benzoic acid (preparable by hydrolyzing the corresponding nitriles, which are described in FR-2,558,831-A) with SOCl$_2$ the corresponding acid chloride and, by subsequent reaction with 2-fluoro-4-propylphenol in the presence of pyridine, 2-fluoro-4-propylphenyl 4-(5-pentylpyridin-2-yl)-benzoate.

Prepared analogously:
2-Fluoro-4-propylphenyl 4-(5-ethylpyridin-2-yl)-benzoate
2-Fluoro-4-propylphenyl 4-(5-propylpyridin-2-yl)-benzoate
2-Fluoro-4-propylphenyl 4-(5-butylpyridin-2-yl)-benzoate
2-Fluoro-4-propylphenyl 4-(5-hexylpyridin-2-yl)-benzoate
2-Fluoro-4-propylphenyl 4-(5-heptylpyridin-2-yl)-benzoate
2-Fluoro-4-propylphenyl 4-(5-octylpyridin-2-yl)-benzoate
2-Fluoro-4-propylphenyl 4-(5-nonylpyridin-2-yl)-benzoate
2-Fluoro-4-ethylphenyl 4-(5-ethylpyridin-2-yl)-benzoate
2-Fluoro-4-ethylphenyl 4-(5-propylpyridin-2-yl)-benzoate
2-Fluoro-4-ethylphenyl 4-(5-butylpyridin-2-yl)-benzoate
2-Fluoro-4-ethylphenyl 4-(5-hexylpyridin-2-yl)-benzoate
2-Fluoro-4-ethylphenyl 4-(5-pentylpyridin-2-yl)-benzoate
2-Fluoro-4-ethylphenyl 4-(5-heptylpyridin-2-yl)-benzoate
2-Fluoro-4-ethylphenyl 4-(5-octylpyridin-2-yl)-benzoate
2-Fluoro-4-ethylphenyl 4-(5-nonylpyridin-2-yl)-benzoate
2-Fluoro-4-butylphenyl 4-(5-ethylpyridin-2-yl)-benzoate
2-Fluoro-4-butylphenyl 4-(5-propylpyridin-2-yl)-benzoate 2-Fluoro-4-butylphenyl 4-(5-butylpyridin-2-yl)-benzoate
2-Fluoro-4-butylphenyl 4-(5-pentylpyridin-2-yl)-benzoate
2-Fluoro-4-butylphenyl 4-(5-hexylpyridin-2-yl)-benzoate
2-Fluoro-4-butylphenyl 4-(5-heptylpyridin-2-yl)-benzoate
2-Fluoro-4-butylphenyl 4-(5-octylpyridin-2-yl)-benzoate
2-Fluoro-4-butylphenyl 4-(5-nonylpyridin-2-yl)-benzoate
2-Fluoro-4-pentylphenyl 4-(5-ethylpyridin-2-yl)-benzoate
2-Fluoro-4-pentylphenyl 4-(5-propylpyridin-2-yl)-benzoate
2-Fluoro-4-pentylphenyl 4-(5-butylpyridin-2-yl)-benzoate
2-Fluoro-4-pentylphenyl 4-(5-pentylpyridin-2-yl)-benzoate
2-Fluoro-4-pentylphenyl 4-(5-hexylpyridin-2-yl)-benzoate
2-Fluoro-4-pentylphenyl 4-(5-heptylpyridin-2-yl)-benzoate
2-Fluoro-4-pentylphenyl 4-(5-octylpyridin-2-yl)-benzoate
2-Fluoro-4pentylphenyl 4-(5-nonylpyridin-2-yl)-benzoate
2-Fluoro-4-hexylphenyl 4-(5-ethylpyridin-2-yl)-benzoate
2-Fluoro-4-hexylphenyl 4-(5-propylpyridin-2-yl)-benzoate
2-Fluoro-4-hexylphenyl 4-(5-butylpyridin-2-yl)-benzoate
2-Fluoro-4-hexylphenyl 4-(5-pentylpyridin-2-yl)-benzoate
2-Fluoro-4-hexylphenyl 4-(5-hexylpyridin-2-yl)-benzoate
2-Fluoro-4-hexylphenyl 4-(5-heptylpyridin-2-yl)-benzoate
2-Fluoro-4-hexylphenyl 4-(5-octylpyridin-2-yl)-benzoate
2-Fluoro-4-hexylphenyl 4-(5-nonylpyridin-2-yl)-benzoate
2-Fluoro-4-hexylphenyl 4-(5-ethylpyrazin-2-yl)-benzoate
2-Fluoro-4-hexylphenyl 4-(5-propylpyrazin-2-yl)-benzoate
2-Fluoro-4-hexylphenyl 4-(5-butylpyrazin-2-yl)-benzoate
2-Fluoro-4-hexylphenyl 4-(5-pentylpyrazin-2-yl)-benzoate
2-Fluoro-4-hexylphenyl 4-(5-hexylpyrazin-2-yl)-benzoate
2-Fluoro-4-hexylphenyl 4-(5-heptylpyrazin-2-yl)-benzoate
2-Fluoro-4-hexylphenyl 4-(5-octylpyrazin-2-yl)-benzoate
2-Fluoro-4-hexylphenyl 4-(5-nonylpyrazin-2-yl)-benzoate
2-Fluoro-4-propylphenyl 4-(5-ethylpyrazin-2-yl)-benzoate
2-Fluoro-4-propylphenyl 4-(5-propylpyrazin-2-yl)-benzoate
2-Fluoro-4-propylphenyl 4-(5-butylpyrazin-2-yl)-benzoate
2-Fluoro-4-propylphenyl 4-(5-pentylpyrazin-2-yl)-benzoate
2-Fluoro-4-propylphenyl 4-(5-hexylpyrazin-2-yl)-benzoate
2-Fluoro-4-propylphenyl 4-(5-heptylpyrazin-2-yl)-benzoate
2-Fluoro-4-propylphenyl 4-(5-octylpyrazin-2-yl)-benzoate
2-Fluoro-4-propylphenyl 4-(5-nonylpyrazin-2-yl)-benzoate
2-Fluoro-4-ethylphenyl 4-(5-ethylpyrazin-2-yl)-benzoate
2-Fluoro-4-ethylphenyl 4-(5-propylpyrazin-2-yl)-benzoate
2-Fluoro-4-ethylphenyl 4-(5-butylpyrazin-2-yl)-benzoate
2-Fluoro-4-ethylphenyl 4-(5-pentylpyrazin-2-yl)-benzoate
2-Fluoro-4-ethylphenyl 4-(5-hexylpyrazin-2-yl)-benzoate
2-Fluoro-4-ethylphenyl 4-(5-heptylpyrazin-2-yl)-benzoate
2-Fluoro-4-ethylphenyl 4-(5-octylpyrazin-2-yl)-benzoate
2-Fluoro-4-ethylphenyl 4-(5-nonylpyrazin-2-yl)-benzoate
2-Fluoro-4-butylphenyl 4-(5-ethylpyrazin-2-yl)-benzoate
2-Fluoro-4-butylphenyl 4-(5-propylpyrazin-2-yl)-benzoate
2-Fluoro-4-butylphenyl 4-(5-butylpyrazin-2-yl)-benzoate
2-Fluoro-4-butylphenyl 4-(5-pentylpyrazin-2-yl)-benzoate
2-Fluoro-4-butylphenyl 4-(5-hexylpyrazin-2-yl)-benzoate
2-Fluoro-4-butylphenyl 4-(5-heptylpyrazin-2-yl)-benzoate
2-Fluoro-4-butylphenyl 4-(5-octylpyrazin-2-yl)-benzoate
2-Fluoro-4-butylphenyl 4-(5-nonylpyrazin-2-yl)-benzoate
2-Fluoro-4-pentylphenyl 4-(5-ethylpyrazin-2-yl)-benzoate
2-Fluoro-4-pentylphenyl 4-(5-propylpyrazin-2-yl)-benzoate
2-Fluoro-4-pentylphenyl 4-(5-butylpyrazin-2-yl)-benzoate
2-Fluoro-4-pentylphenyl 4-(5-pentylpyrazin-2-yl)-benzoate
2-Fluoro-4-pentylphenyl 4-(5-hexylpyrazin-2-yl)-benzoate
2-Fluoro-4-pentylphenyl 4-(5-heptylpyrazin-2-yl)-benzoate
2-Fluoro-4-pentylphenyl 4-(5-octylpyrazin-2-yl)-benzoate
2-Fluoro-4-pentylphenyl 4-(5-nonylpyrazin-2-yl)-benzoate

EXAMPLE 8

Example 6 is repeated to obtain from 2-p-hydroxyphenyl-5-n-pentylpyridine by reaction with 2-fluoro-4-octylbenzoyl chloride the corresponding 4-(5-n-pentylpyridin-2-yl)phenyl 2-fluoro-4-octylbenzoate.

Prepared analogously:
4-(5-Pentylpyridin-2-yl)-phenyl 2-fluoro-4-ethylbenzoate
4-(5-Pentylpyridin-2-yl)-phenyl 2-fluoro-4-propylbenzoate 4-(5-Pentylpyridin-2-yl)-phenyl 2-fluoro-4-butylbenzoate
4-(5-Pentylpyridin-2-yl)-phenyl 2-fluoro-4-pentylbenzoate
4-(5-Pentylpyridin-2-yl)-phenyl 2-fluoro-4-hexylbenzoate
4-(5-Pentylpyridin-2-yl)-phenyl 2-fluoro-4-heptylbenzoate
4-(5-Ethylpyridin-2-yl)-phenyl 2-fluoro-4-ethylbenzoate
4-(5-Ethylpyridin-2-yl)-phenyl 2-fluoro-4-propylbenzoate
4-(5-Ethylpyridin-2-yl)-phenyl 2-fluoro-4-butylbenzoate
4-(5-Ethylpyridin-2-yl)-phenyl 2-fluoro-4-pentylbenzoate
4-(5-Ethylpyridin-2-yl)-phenyl 2-fluoro-4-hexylbenzoate
4-(5-Ethylpyridin-2-yl)-phenyl 2-fluoro-4-heptylbenzoate
4-(5-Ethylpyridin-2-yl)-phenyl 2-fluoro-4-octylbenzoate
4-(5-Propylpyridin-2-yl)-phenyl 2-fluoro-4-ethylbenzoate
4-(5-Propylpyridin-2-yl)-phenyl 2-fluoro-4-propylbenzoate
4-(5-Propylpyridin-2-yl)-phenyl 2-fluoro-4-butylbenzoate
4-(5-Propylpyridin-2-yl)-phenyl 2-fluoro-4-pentylbenzoate
4-(5-Propylpyridin-2-yl)-phenyl 2-fluoro-4-hexylbenzoate
4-(5-Propylpyridin-2-yl)-phenyl 2-fluoro-4-heptylbenzoate
4-(5-Propylpyridin-2-yl)-phenyl 2-fluoro-4-octylbenzoate
4-(5-Butylpyridin-2-yl)-phenyl 2-fluoro-4-ethylbenzoate
4-(5-Butylpyridin-2-yl)-phenyl 2-fluoro-4-propylbenzoate
4-(5-Butylpyridin-2-yl)-phenyl 2-fluoro-4-butylbenzoate
4-(5-Butylpyridin-2-yl)-phenyl 2-fluoro-4-pentylbenzoate
4-(5-Butylpyridin-2-yl)-phenyl 2-fluoro-4-hexylbenzoate
4-(5-Butylpyridin-2-yl)-phenyl 2-fluoro-4-heptylbenzoate
4-(5-Butylpyridin-2-yl)-phenyl 2-fluoro-4-octylbenzoate
4-(5-Hexylpyridin-2-yl)-phenyl 2-fluoro-4-ethylbenzoate
4-(5-Hexylpyridin-2-yl)-phenyl 2-fluoro-4-propylbenzoate
4-(5-Hexylpyridin-2-yl)-phenyl 2-fluoro-4-butylbenzoate
4-(5-Hexylpyridin-2-yl)-phenyl 2-fluoro-4-pentylbenzoate
4-(5-Hexylpyridin-2-yl)-phenyl 2-fluoro-4-hexylbenzoate
4-(5-Hexylpyridin-2-yl)-phenyl 2-fluoro-4-heptylbenzoate
4-(5-Hexylpyridin-2-yl)-phenyl 2-fluoro-4-octylbenzoate
4-(5-Heptylpyridin-2-yl)-phenyl 2-fluoro-4-ethylbenzoate
4-(5-Heptylpyridin-2-yl)-phenyl 2-fluoro-4-propylbenzoate
4-(5-Heptylpyridin-2-yl)-phenyl 2-fluoro-4-butylbenzoate
4-(5-Heptylpyridin-2-yl)-phenyl 2-fluoro-4-pentylbenzoate
4-(5-Heptylpyridin-2-yl)-phenyl 2-fluoro-4-hexylbenzoate
4-(5-Heptylpyridin-2-yl)-phenyl 2-fluoro-4-heptylbenzoate
4-(5-Heptylpyridin-2-yl)-phenyl 2-fluoro-4-octylbenzoate
4-(5-Octylpyridin-2-yl)-phenyl 2-fluoro-4-ethylbenzoate
4-(5-Octylpyridin-2-yl)-phenyl 2-fluoro-4-propylbenzoate
4-(5-Octylpyridin-2-yl)-phenyl 2-fluoro-4-butylbenzoate
4-(5-Octylpyridin-2-yl)-phenyl 2-fluoro-4-pentylbenzoate
4-(5-Octylpyridin-2-yl)-phenyl 2-fluoro-4-hexylbenzoate
4-(5-Octylpyridin-2-yl)-phenyl 2-fluoro-4-heptylbenzoate
4-(5-Octylpyridin-2-yl)-phenyl 2-fluoro-4-octylbenzoate
4-(5-Nonylpyridin-2-yl)-phenyl 2-fluoro-4-ethylbenzoate
4-(5-Nonylpyridin-2-yl)-phenyl 2-fluoro-4-propylbenzoate
4-(5-Nonylpyridin-2-yl)-phenyl 2-fluoro-4-butylbenzoate
4-(5-Nonylpyridin-2-yl)-phenyl 2-fluoro-4-pentylbenzoate
4-(5-Nonylpyridin-2-yl)-phenyl 2-fluoro-4-hexylbenzoate
4-(5-Nonylpyridin-2-yl)-phenyl 2-fluoro-4-heptylbenzoate
4-(5-Nonylpyridin-2-yl)-phenyl 2-fluoro-4-octylbenzoate
4-(5-Nonylpyridin-2-yl)-phenyl trans-4-propylcyclohexanecarboxylate
4-(5-Nonylpyridin-2-yl)-phenyl trans-4-butylcyclohexanecarboxylate
4-(5-Nonylpyridin-2-yl)-phenyl trans-4-pentylcyclohexanecarboxylate
4-(5-Nonylpyridin-2-yl)-phenyl trans-4-hexylcyclohexanecarboxylate
4-(5-Nonylpyridin-2-yl)-phenyl trans-4-heptylcyclohexanecarboxylate
4-(5-Nonylpyridin-2-yl)-phenyl trans-4-octylcyclohexanecarboxylate
4-(5-Octylpyridin-2-yl)-phenyl trans-4-propylcyclohexanecarboxylate
4-(5-Octylpyridin-2-yl)-phenyl trans-4-butylcyclohexanecarboxylate
4-(5-Octylpyridin-2-yl)-phenyl trans-4-pentylcyclohexanecarboxylate
4-(5-Octylpyridin-2-yl)-phenyl trans-4-hexylcyclohexanecarboxylate
4-(5-Octylpyridin-2-yl)-phenyl trans-4-heptylcyclohexanecarboxylate
4-(5-Octylpyridin-2-yl)-phenyl trans-4-octylcyclohexanecarboxylate
4-(5-Heptylpyridin-2-yl)-phenyl trans-4-propylcyclohexanecarboxylate
4-(5-Heptylpyridin-2-yl)-phenyl trans-4-butylcyclohexanecarboxylate
4-(5-Heptylpyridin-2-yl)-phenyl trans-4-pentylcyclohexanecarboxylate 4-(5-Heptylpyridin-2-yl)-phenyl trans-4-hexylcyclohexanecarboxylate
4-(5-Heptylpyridin-2-yl)-phenyl trans-4-heptylcyclohexanecarboxylate
4-(5-Heptylpyridin-2-yl)-phenyl trans-4-octylcyclohexanecarboxylate
4-(5-Hexylpyridin-2-yl)-phenyl trans-4-propylcyclohexanecarboxylate
4-(5-Hexylpyridin-2-yl)-phenyl trans-4-butylcyclohexanecarboxylate
4-(5-Hexylpyridin-2-yl)-phenyl trans-4-pentylcyclohexanecarboxylate
4-(5-Hexylpyridin-2-yl)-phenyl trans-4-hexylcyclohexanecarboxylate
4-(5-Hexylpyridin-2-yl)-phenyl trans-4-heptylcyclohexanecarboxylate
4-(5-Hexylpyridin-2-yl)-phenyl trans-4-octylcyclohexanecarboxylate
4-(5-Pentylpyridin-2-yl)-phenyl trans-4-propylcyclohexanecarboxylate
4-(5-Pentylpyridin-2-yl)-phenyl trans-4-butylcyclohexanecarboxylate
4-(5-Pentylpyridin-2-yl)-phenyl trans-4-pentylcyclohexanecarboxylate
4-(5-Pentylpyridin-2-yl)-phenyl trans-4-hexylcyclohexanecarboxylate
4-(5-Pentylpyridin-2-yl)-phenyl trans-4-heptylcyclohexanecarboxylate
4-(5-Pentylpyridin-2-yl)-phenyl trans-4-octylcyclohexanecarboxylate
4-(5-Butylpyridin-2-yl)-phenyl trans-4-propylcyclohexanecarboxylate
4-(5-Butylpyridin-2-yl)-phenyl trans-4-butylcyclohexanecarboxylate
4-(5-Butylpyridin-2-yl)-phenyl trans-4-pentylcyclohexanecarboxylate
4-(5-Butylpyridin-2-yl)-phenyl trans-4-hexylcyclohexanecarboxylate
4-(5-Butylpyridin-2-yl)-phenyl trans-4-heptylcyclohexanecarboxylate
4-(5-Butylpyridin-2-yl)-phenyl trans-4-octylcyclohexanecarboxylate
4-(5-Propylpyridin-2-yl)-phenyl trans-4-propylcyclohexanecarboxylate
4-(5-Propylpyridin-2-yl)-phenyl trans-4-butylcyclohexanecarboxylate
4-(5-Propylpyridin-2-yl)-phenyl trans-4-pentylcyclohexanecarboxylate
4-(5-Propylpyridin-2-yl)-phenyl trans-4-hexylcyclohexanecarboxylate
4-(5-Propylpyridin-2-yl)-phenyl trans-4-heptylcyclohexanecarboxylate
4-(5-Propylpyridin-2-yl)-phenyl trans-4-octylcyclohexanecarboxylate
4-(5-Ethylpyridin-2-yl)-phenyl trans-4-propylcyclohexanecarboxylate
4-(5-Ethylpyridin-2-yl)-phenyl trans-4-butylcyclohexanecarboxylate
4-(5-Ethylpyridin-2-yl)-phenyl trans-4-pentylcyclohexanecarboxylate
4-(5-Ethylpyridin-2-yl)-phenyl trans-4-hexylcyclohexanecarboxylate
4-(5-Ethylpyridin-2-yl)-phenyl trans-4-heptylcyclohexanecarboxylate
4-(5-Ethylpyridin-2-yl)-phenyl trans-4-octylcyclohexanecarboxylate

EXAMPLE 9

A mixture of 0.0375 mol of 5-(p-hexyloxyphenyl)-pyrazine-2-carboxylic acid prepared as described in the known literature and 240 ml of $SOCl_2$ is heated for 2 hours. After evaporation, the acid chloride obtained is dissolved in 750 ml of toluene, pyridine and 24 mmol of p-octyloxyphenol are added, and the mixture is heated for 2 hours. Cooling down and customary working up gives p-octyloxyphenyl 5-(p-hexyloxyphenyl)-pyrazine-2-carboxylate.

Prepared analogously:
p-octyloxyphenyl 5-(p-pentyloxyphenyl)-pyrazine-2-carboxylate
p-octyloxyphenyl 5-(p-propyloxyphenyl)-pyrazine-2-carboxylate
p-octyloxyphenyl 5-(p-butyloxyphenyl)-pyrazine-2-carboxylate
p-octyloxyphenyl 5-(p-heptyloxyphenyl)-pyrazine-2-carboxylate
p-octyloxyphenyl 5-(p-octyloxyphenyl)-pyrazine-2-carboxylate, C 115° $Sm_C$ 179° $Sm_A$ 187° N 191° I
p-octyloxyphenyl 5-(p-nonyloxyphenyl)-pyrazine-2-carboxylate
p-octyloxyphenyl 5-(p-decyloxyphenyl)-pyrazine-2-carboxylate
p-octyloxyphenyl 5-(p-undecyloxyphenyl)-pyrazine-2-carboxylate
p-octyloxyphenyl 5-(p-dodecyloxyphenyl)-pyrazine-2-carboxylate
p-heptyloxyphenyl 5-(p-pentyloxyphenyl)-pyrazine-2-carboxylate
p-heptyloxyphenyl 5-(p-propyloxyphenyl)-pyrazine-2-carboxylate
p-heptyloxyphenyl 5-(p-butyloxyphenyl)-pyrazine-2-carboxylate
p-heptyloxyphenyl 5-(p-hexyloxyphenyl)-pyrazine-2-carboxylate
p-heptyloxyphenyl 5-(p-heptyloxyphenyl)-pyrazine-2-carboxylate
p-heptyloxyphenyl 5-(p-octyloxyphenyl)-pyrazine-2-carboxylate, C 114° $Sm_C$ 184° $Sm_A$ 190° N 194° I
p-heptyloxyphenyl 5-(p-nonyloxyphenyl)-pyrazine-2-carboxylate
p-heptyloxyphenyl 5-(p-decyloxyphenyl)-pyrazine-2-carboxylate
p-heptyloxyphenyl 5-(p-undecyloxyphenyl)-pyrazine-2-carboxylate
p-heptyloxyphenyl 5-(p-dodecyloxyphenyl)-pyrazine-2-carboxylate
p-(2-methylbutyloxyphenyl) 5-(p-pentyloxyphenyl)-pyrazine-2-carboxylate
p-(2-methylbutyloxyphenyl) 5-(p-propyloxyphenyl)-pyrazine-2-carboxylate
p-(2-methylbutyloxyphenyl) 5-(p-butyloxyphenyl)-pyrazine-2-carboxylate
p-(2-methylbutyloxyphenyl) 5-(p-hexyloxyphenyl)-pyrazine-2-carboxylate
p-(2-methylbutyloxyphenyl) 5-(p-heptyloxyphenyl)-pyrazine-2-carboxylate
p-(2-methylbutyloxyphenyl) 5-(p-octyloxyphenyl)-pyrazine-2-carboxylate, C 126° $Sm_{C^*}$ 163° $Sm_A$ 177° I
p-(2-methylbutyloxyphenyl) 5-(p-nonyloxyphenyl)-pyrazine-2-carboxylate, C 122° $Sm_{C^*}$ 158° $SM_A$ 172° I
p-(2-methylbutyloxyphenyl) 5-(p-decyloxyphenyl)-pyrazine-2-carboxylate
p-(2-methylbutyloxyphenyl) 5-(p-undecyloxyphenyl)-pyrazine-2-carboxylate p-(2-methylbutyloxyphenyl) 5-(p-dodecyloxyphenyl)-pyrazine-2-carboxylate
p-hexylphenyl 5-(p-pentyloxyphenyl)-pyrazine-2-carboxylate
p-hexylphenyl 5-(p-propyloxyphenyl)-pyrazine-2-carboxylate
p-hexylphenyl 5-(p-butyloxyphenyl)-pyrazine-2-carboxylate
p-hexylphenyl 5-(p-hexyloxyphenyl)-pyrazine-2-carboxylate
p-hexylphenyl 5-(p-heptyloxyphenyl)-pyrazine-2-carboxylate
p-hexylphenyl 5-(p-octyloxyphenyl)-pyrazine-2-carboxylate
p-hexylphenyl 5-(p-nonyloxyphenyl)-pyrazine-2-carboxylate
p-hexylphenyl 5-(p-decyloxyphenyl)-pyrazine-2-carboxylate
p-hexylphenyl 5-(p-undecyloxyphenyl)-pyrazine-2-carboxylate
p-hexylphenyl 5-(p-dodecyloxyphenyl)-pyrazine-2-carboxylate
p-pentylphenyl 5-(p-pentyloxyphenyl)-pyrazine-2-carboxylate
p-pentylphenyl 5-(p-propyloxyphenyl)-pyrazine-2-carboxylate
p-pentylphenyl 5-(p-butyloxyphenyl)-pyrazine-2-carboxylate
p-pentylphenyl 5-(p-hexyloxyphenyl)-pyrazine-2-carboxylate
p-pentylphenyl 5-(p-heptyloxyphenyl)-pyrazine-2-carboxylate
p-pentylphenyl 5-(p-octyloxyphenyl)-pyrazine-2-carboxylate
p-pentylphenyl 5-(p-nonyloxyphenyl)-pyrazine-2-carboxylate
p-pentylphenyl 5-(p-decyloxyphenyl)-pyrazine-2-carboxylate
p-pentylphenyl 5-(p-undecyloxyphenyl)-pyrazine-2-carboxylate
p-pentylphenyl 5-(p-dodecyloxyphenyl)-pyrazine-2-carboxylate
p-hexyloxyphenyl 5-(p-pentylphenyl)-pyrazine-2-carboxylate
p-hexyloxyphenyl 5-(p-propylphenyl)-pyrazine-2-carboxylate
p-hexyloxyphenyl 5-(p-butylphenyl)-pyrazine-2-carboxylate
p-hexyloxyphenyl 5-(p-hexylphenyl)-pyrazine-2-carboxylate
p-hexyloxyphenyl 5-(p-heptylphenyl)-pyrazine-2-carboxylate
p-hexyloxyphenyl 5-(p-octylphenyl)-pyrazine-2-carboxylate
p-hexyloxyphenyl 5-(p-nonylphenyl)-pyrazine-2-carboxylate
p-hexyloxyphenyl 5-(p-decylphenyl)-pyrazine-2-carboxylate
p-hexyloxyphenyl 5-(p-undecylphenyl)-pyrazine-2-carboxylate
p-hexyloxyphenyl 5-(p-dodecylphenyl)-pyrazine-2-carboxylate
p-heptylphenyl 5-(p-pentylphenyl)-pyrazine-2-carboxylate
p-heptylphenyl 5-(p-propylphenyl)-pyrazine-2-carboxylate
p-heptylphenyl 5-(p-butylphenyl)-pyrazine-2-carboxylate
p-heptylphenyl 5-(p-hexylphenyl)-pyrazine-2-carboxylate
p-heptylphenyl 5-(p-heptylphenyl)-pyrazine-2-carboxylate
p-heptylphenyl 5-(p-octylphenyl)-pyrazine-2-carboxylate
p-heptylphenyl 5-(p-nonylphenyl)-pyrazine-2-carboxylate
p-heptylphenyl 5-(p-decylphenyl)-pyrazine-2-carboxylate
p-heptylphenyl 5-(p-undecylphenyl)-pyrazine-2-carboxylate
p-heptylphenyl 5-(p-dodecylphenyl)-pyrazine-2-carboxylate
2-fluoro-4-octylphenyl 5-(p-pentyloxyphenyl)-pyrazine-2-carboxylate
2-fluoro-4-octylphenyl 5-(p-propyloxyphenyl)-pyrazine-2-carboxylate
2-fluoro-4-octylphenyl 5-(p-butyloxyphenyl)-pyrazine-2-carboxylate
2-fluoro-4-octylphenyl 5-(p-hexyloxyphenyl)-pyrazine-2-carboxylate
2-fluoro-4-octylphenyl 5-(p-heptyloxyphenyl)-pyrazine-2-carboxylate
2-fluoro-4-octylphenyl 5-(p-octyloxyphenyl)-pyrazine-2-carboxylate
2-fluoro-4-octylphenyl 5-(p-nonyloxyphenyl)-pyrazine-2-carboxylate
2-fluoro-4-octylphenyl 5-(p-decyloxyphenyl)-pyrazine-2-carboxylate
2-fluoro-4-octylphenyl 5-(p-undecyloxyphenyl)-pyrazine-2-carboxylate
2-fluoro-4-octylphenyl 5-(p-dodecyloxyphenyl)-pyrazine-2-carboxylate
2-fluoro-4-octylphenyl 5-(p-pentylphenyl)-pyrazine-2-carboxylate
2-fluoro-4-octylphenyl 5-(p-propylphenyl)-pyrazine-2-carboxylate
2-fluoro-4-octylphenyl 5-(p-butylphenyl)-pyrazine-2-carboxylate
2-fluoro-4-octylphenyl 5-(p-hexylphenyl)-pyrazine-2-carboxylate
2-fluoro-4-octylphenyl 5-(p-heptylphenyl)-pyrazine-2-carboxylate
2-fluoro-4-octylphenyl 5-(p-octylphenyl)-pyrazine-2-carboxylate
2-fluoro-4-octylphenyl 5-(p-nonylphenyl)-pyrazine-2-carboxylate
2-fluoro-4-octylphenyl 5-(p-decylphenyl)-pyrazine-2-carboxylate
2-fluoro-4-octylphenyl 5-(p-undecylphenyl)-pyrazine-2-carboxylate
2-fluoro-4-octylphenyl 5-(p-dodecylphenyl)-pyrazine-2-carboxylate
2-fluoro-4-nonylphenyl 5-(p-pentylphenyl)-pyrazine-2-carboxylate
2-fluoro-4-nonylphenyl 5-(p-propylphenyl)-pyrazine-2-carboxylate
2-fluoro-4-nonylphenyl 5-(p-butylphenyl)-pyrazine-2-carboxylate
2-fluoro-4-nonylphenyl 5-(p-hexylphenyl)-pyrazine-2-carboxylate
2-fluoro-4-nonylphenyl 5-(p-heptylphenyl)-pyrazine-2-carboxylate
2-fluoro-4-nonylphenyl 5-(p-octylphenyl)-pyrazine-2-carboxylate
2-fluoro-4-nonylphenyl 5-(p-nonylphenyl)-pyrazine-2-carboxylate 2-fluoro-4-nonylphenyl 5-(p-decylphenyl)-pyrazine-2-carboxylate 2-fluoro-4-nonylphenyl 5-(p-undecylphenyl)-pyrazine-2-carboxylate 2-fluoro-4-nonylphenyl 5-(p-dodecylphenyl)-pyrazine-2-carboxylate 2-fluoro-4-decylphenyl 5-(p-pentylphenyl)-pyrazine-2-carboxylate 2-fluoro-4-decylphenyl 5-(p-propylphenyl)-pyrazine-2-carboxylate 2-fluoro-4-decylphenyl 5-(p-butylphenyl)-pyrazine-2-carboxylate 2-fluoro-4-decylphenyl 5-(p-hexylphenyl)-pyrazine-2-carboxylate 2-fluoro-4-decylphenyl 5-(p-heptylphenyl)-pyrazine-2-carboxylate 2-fluoro-4-decylphenyl 5-(p-octylphenyl)-pyrazine-2-carboxylate 2-fluoro-4-decylphenyl 5-(p-nonylphenyl)-pyrazine-2-carboxylate 2-fluoro-4-decylphenyl 5-(p-decylphenyl)-pyrazine-2-carboxylate 2-fluoro-4-decylphenyl 5-(p-undecylphenyl)-pyrazine-2-carboxylate 2-fluoro-4-decylphenyl 5-(p-dodecylphenyl)-pyrazine-2-carboxylate

EXAMPLE 10

0.02 mol of triethylamine is added with stirring to a solution of 0.019 mol of 3-chloro-1-[4-(trans-4pentylcyclohexylethyl)phenyl]propan-1-one (m.p. 73°-74°, preparable by (a) Friedel-Crafts reaction of benzene with trans-4-pentyl-cyclohexylacetyl chloride, (b) subsequent Huang-Minlon reduction to 1-(trans-4-pentylcyclohexyl)2-phenylethane (boiling point: 125°/0.3 mmHg) and (c) reaction of this compound with 3-chloropropanoyl chloride in $CH_2Cl_2$ and $AlCl_3$) in 5 ml of tetrahydrofuran. After stirring for one hour, 0.019 mol of 1-piperidinopentene (boiling point: 101°-104°/18 mmHg, preparable as described in G. Stork et al., J. Amer. Chem. Soc. 1963, 85, 207 and C. Mannich and H. Davidsen, Chem. Ber. 1936, 69, 2106) in 5 ml of THF are added, which is followed by stirring for 72 hours.

The solvent is removed and the residue is taken up in ethanol-water (1:1, 10 ml) and heated with 0.059 mol of hydroxylamine hydrochloride with stirring for 72 hours.

The solvent is evaporated off, and the residue is treated with NaOH solution (10%, 100 ml) and ether (50 ml). The organic phase is worked up as customary to give, after purification by means of column chromatography (neutral aluminum oxide, eluant petroleum ether/chloroform) and recrystallization, 2-p-[2'-(trans-4-pentylcyclohexyl)ethyl]phenyl-5-propylpyridine having C 36° $S_G$ 53° $S_B$ 100° N 150° I (cf. also C. Botteghi et al., Synth. Comm. 1979, 9(2), 69).

Prepared analogously:

2-p-[2'-(trans-4-propylcyclohexyl)ethyl]phenyl-5-propylpyridine, C 81° N 149° I 2-p-[2'-(trans-4-propylcyclohexyl)ethyl]phenyl-5-butylpyridine, C 88° N 142° I 2-p-[2'-(trans-4-propylcyclohexyl)ethyl]phenyl-5-pentylpyridine, C 93° N 156° I 2-p-[2'-(trans-4-propylcyclohexyl)ethyl]phenyl-5-hexylpyridine 2-p-[2'-(trans-4-propylcyclohexyl)ethyl]phenyl-5-heptylpyridine 2-p-[2'-(trans-4-propylcyclohexyl)ethyl]phenyl-5-octylpyridine 2-p-[2'-(trans-4-propylcyclohexyl)ethyl]phenyl-5-ethylpyridine 2-p-[2'-(trans-4-ethylcyclohexyl)ethyl]phenyl-5-propylpyridine 2-p-[2'-(trans-4-ethylcyclohexyl)ethyl]phenyl-5-butylpyridine 2-p-[2'-(trans-4-ethylcyclohexyl)ethyl]phenyl-5-pentylpyridine 2-p-[2'-(trans-4-ethylcyclohexyl)ethyl]phenyl-5-hexylpyridine 2-p-[2'-(trans-4-ethylcyclohexyl)ethyl]phenyl-5-heptylpyridine 2-p-[2'-(trans-4-ethylcyclohexyl)ethyl]phenyl-5-octylpyridine 2-p-[2'-(trans-4-ethylcyclohexyl)ethyl]phenyl-5-ethylpyridine 2-p-[2'-(trans-4-butylcyclohexyl)ethyl]phenyl-5-propylpyridine 2-p-[2'-(trans-4-butylcyclohexyl)ethyl]phenyl-5-butylpyridine 2-p-[2'-(trans-4-butylcyclohexyl)ethyl]phenyl-5-pentylpyridine, C 102° N 137° I 2-p-[2'-(trans-4-butylcyclohexyl)ethyl]phenyl-5-hexylpyridine 2-p-[2'-(trans-4-butylcyclohexyl)ethyl]phenyl-5-heptylpyridine 2-p-[2'-(trans-4-butylcyclohexyl)ethyl]phenyl-5-octylpyridine, C 79° S 148° N 153° I 2-p-[2'-(trans-4-butylcyclohexyl)ethyl]phenyl-5-ethylpyridine 2-p-[2'-(trans-4-pentylcyclohexyl)ethyl]phenyl-5-butylpyridine 2-p-[2'-(trans-4-pentylcyclohexyl)ethyl]phenyl-5-pentylpyridine, C 99° S 141° N 146° I 2-p-[2'-(trans-4-pentylcyclohexyl)ethyl]phenyl-5-hexylpyridine 2-p-[2'-(trans-4-pentylcyclohexyl)ethyl]phenyl-5-heptylpyridine 2-p-[2'-(trans-4-pentylcyclohexyl)ethyl]phenyl-5-octylpyridine 2-p-[2'-(trans-4-pentylcyclohexyl)ethyl]phenyl-5-ethylpyridine 2-p-[2'-(trans-4-hexylcyclohexyl)ethyl]phenyl-5-propylpyridine 2-p-[2'-(trans-4-hexylcyclohexyl)ethyl]phenyl-5-butylpyridine 2-p-[2'-(trans-4-hexylcyclohexyl)ethyl]phenyl-5-pentylpyridine 2-p-[2'-(trans-4-hexylcyclohexyl)ethyl]phenyl-5-hexylpyridine 2-p-[2'-(trans-4-hexylcyclohexyl)ethyl]phenyl-5-heptylpyridine 2-p-[2'-(trans-4-hexylcyclohexyl)ethyl]phenyl-5-octylpyridine 2-p-[2'-(trans-4-hexylcyclohexyl)ethyl]phenyl-5-ethylpyridine 2-p-[2'-(trans-4-heptylcyclohexyl)ethyl]phenyl-5-propylpyridine 2-p-[2'-(trans-4-heptylcyclohexyl)ethyl]phenyl-5-butylpyridine 2-p-[2'-(trans-4-heptylcyclohexyl)ethyl]phenyl-5-pentylpyridine 2-p-[2'-(trans-4-heptylcyclohexyl)ethyl]phenyl-5-hexylpyridine 2-p-[2'-(trans-4-heptylcyclohexyl)ethyl]phenyl-5-heptylpyridine 2-p-[2'-(trans-4-heptylcyclohexyl)ethyl]phenyl-5-octylpyridine
2-p-[2'-(trans-4-heptylcyclohexyl)ethyl]phenyl-5-ethylpyridine
2-p-[2'-(trans-4-octylcyclohexyl)ethyl]phenyl-5-propylpyridine
2-p-[2'-(trans-4-octylcyclohexyl)ethyl]phenyl-5-butylpyridine
2-p-[2'-(trans-4-octylcyclohexyl)ethyl]phenyl-5-pentylpyridine
2-p-[2'-(trans-4-octylcyclohexyl)ethyl]phenyl-5-hexylpyridine
2-p-[2'-(trans-4-octylcyclohexyl)ethyl]phenyl-5-heptylpyridine
2-p-[2'-(trans-4-octylcyclohexyl)ethyl]phenyl-5-octylpyridine
2-p-[2'-(trans-4-octylcyclohexyl)ethyl]phenyl-5-ethylpyridine
2-p-[2'-(trans-4-propylcyclohexyl)ethyl]phenyl-5-ethoxypyridine, C 121° S 142° N 157° I
2-p-[2'-(trans-4-butylcyclohexyl)ethyl]phenyl-5-ethoxypyridine
2-p-[2'-(trans-4-pentylcyclohexyl)ethyl]phenyl-5-ethoxypyridine
2-p-[2'-(trans-4-hexylcyclohexyl)ethyl]phenyl-5-ethoxypyridine
2-p-[2'-(trans-4-heptylcyclohexyl)ethyl]phenyl-5-ethoxypyridine
2-p-[2'-(trans-4-octylcyclohexyl)ethyl]phenyl-5-ethoxypyridine
2-p-[2'-(trans-4-propylcyclohexyl)ethyl]phenyl-5-propoxypyridine
2-p-[2'-(trans-4-butylcyclohexyl)ethyl]phenyl-5-propoxypyridine
2-p-[2'-(trans-4-pentylcyclohexyl)ethyl]phenyl-5-propoxypyridine
2-p-[2'-(trans-4-hexylcyclohexyl)ethyl]phenyl-5-propoxypyridine
2-p-[2'-(trans-4-heptylcyclohexyl)ethyl]phenyl-5-propoxypyridine
2-p-[2'-(trans-4-octylcyclohexyl)ethyl]phenyl-5-propoxypyridine
2-p-[2'-(trans-4-propylcyclohexyl)ethyl]phenyl-5-butoxypyridine, C 111° S 135° N 142° I
2-p-[2'-(trans-4-butylcyclohexyl)ethyl]phenyl-5-butoxypyridine
2-p-[2'-(trans-4-pentylcyclohexyl)ethyl]phenyl-5-butoxypyridine
2-p-[2'-(trans-4-hexylcyclohexyl)ethyl]phenyl-5-butoxypyridine
2-p-[2'-(trans-4-heptylcyclohexyl)ethyl]phenyl-5-butoxypyridine
2-p-[2'-(trans-4-octylcyclohexyl)ethyl]phenyl-5-butoxypyridine
2-p-[2'-(trans-4-propylcyclohexyl)ethyl]phenyl-5-pentoxypyridine
2-p-[2'-(trans-4-butylcyclohexyl)ethyl]phenyl-5-pentoxypyridine
2-p-[2'-(trans-4-pentylcyclohexyl)ethyl]phenyl-5-pentoxypyridine
2-p-[2'-(trans-4-hexylcyclohexyl)ethyl]phenyl-5-pentoxypyridine
2-p-[2'-(trans-4-heptylcyclohexyl)ethyl]phenyl-5-pentoxypyridine
2-p-[2'-(trans-4-octylcyclohexyl)ethyl]phenyl-5-pentoxypyridine
2-p-[2'-(trans-4-propylcyclohexyl)ethyl]phenyl-5-hexoxypyridine
2-p-[2'-(trans-4-butylcyclohexyl)ethyl]phenyl-5-hexoxypyridine
2-p-[2'-(trans-4-pentylcyclohexyl)ethyl]phenyl-5-hexoxypyridine
2-p-[2'-(trans-4-hexylcyclohexyl)ethyl]phenyl-5-hexoxypyridine
2-p-[2'-(trans-4-heptylcyclohexyl)ethyl]phenyl-5-hexoxypyridine
2-p-[2'-(trans-4-octylcyclohexyl)ethyl]phenyl-5-hexoxypyridine
2-[2-fluoro-4-(2'-trans-4-ethylcyclohexylethyl)phenyl]-5-methylpyridine
2-[2-fluoro-4-(2'-trans-4-propylcyclohexylethyl)phenyl]-5-methylpyridine
2-[2-fluoro-4-(2'-trans-4-butylcyclohexylethyl)phenyl]-5-methylpyridine
2-[2-fluoro-4-(2'-trans-4-pentylcyclohexylethyl)phenyl]-5-methylpyridine
2-[2-fluoro-4-(2'-trans-4-hexylcyclohexylethyl)phenyl]-5-methylpyridine
2-[2-fluoro-4-(2'-trans-4-heptylcyclohexylethyl)phenyl]-5-methylpyridine
2-[2-fluoro-4-(2'-trans-4-octylcyclohexylethyl)phenyl]-5-methylpyridine
2-[2-fluoro-4-(2'-trans-4-ethylcyclohexylethyl)phenyl]-5-ethylpyridine
2-[2-fluoro-4-(2'-trans-4-propylcyclohexylethyl)phenyl]-5-ethylpyridine
2-[2-fluoro-4-(2'-trans-4-butylcyclohexylethyl)phenyl]-5-ethylpyridine
2-[2-fluoro-4-(2'-trans-4-pentylcyclohexylethyl)phenyl]-5-ethylpyridine
2-[2-fluoro-4-(2'-trans-4-hexylcyclohexylethyl)phenyl]-5-ethylpyridine
2-[2-fluoro-4-(2'-trans-4-heptylcyclohexylethyl)phenyl]-5-ethylpyridine
2-[2-fluoro-4-(2'-trans-4-octylcyclohexylethyl)phenyl]-5-ethylpyridine
2-[2-fluoro-4-(2'-trans-4-ethylcyclohexylethyl)phenyl]-5-propylpyridine
2-[2-fluoro-4-(2'-trans-4-propylcyclohexylethyl)phenyl]-5-propylpyridine
2-[2-fluoro-4-(2'-trans-4-butylcyclohexylethyl)phenyl]-5-propylpyridine
2-[2-fluoro-4-(2'-trans-4-pentylcyclohexylethyl)phenyl]-5-propylpyridine
2-[2-fluoro-4-(2'-trans-4-hexylcyclohexylethyl)phenyl]-5-propylpyridine
2-[2-fluoro-4-(2'-trans-4-heptylcyclohexylethyl)phenyl]-5-propylpyridine
2-[2-fluoro-4-(2'-trans-4-octylcyclohexylethyl)phenyl]-5-propylpyridine
2-[2-fluoro-4-(2'-trans-4-ethylcyclohexylethyl)phenyl]-5-butylpyridine
2-[2-fluoro-4-(2'-trans-4-propylcyclohexylethyl)phenyl]-5-butylpyridine
2-[2-fluoro-4-(2'-trans-4-butylcyclohexylethyl)phenyl]-5-butylpyridine
2-[2-fluoro-4-(2'-trans-4-pentylcyclohexylethyl)phenyl]-5-butylpyridine
2-[2-fluoro-4-(2'-trans-4-hexylcyclohexylethyl)phenyl]-5-butylpyridine
2-[2-fluoro-4-(2'-trans-4-heptylcyclohexylethyl)phenyl]-5-butylpyridine
2-[2-fluoro-4-(2'-trans-4-octylcyclohexylethyl)phenyl]-5-butylpyridine
2-[2-fluoro-4-(2'-trans-4-ethylcyclohexylethyl)phenyl]-5-pentylpyridine 2-[2-fluoro-4-(2'-trans-4-propylcyclohexylethyl)-phenyl]-5-pentylpyridine
2-[2-fluoro-4-(2'-trans-4-butylcyclohexylethyl)phenyl]-5-pentylpyridine
2-[2-fluoro-4-(2'-trans-4-pentylcyclohexylethyl)-phenyl]-5-pentylpyridine
2-[2-fluoro-4-(2'-trans-4-hexylcyclohexylethyl)phenyl]-5-pentylpyridine
2-[2-fluoro-4-(2'-trans-4-heptylcyclohexylethyl)-phenyl]-5-pentylpyridine
2-[2-fluoro-4-(2'-trans-4-octylcyclohexylethyl)phenyl]-5-pentylpyridine

EXAMPLE 11

A mixture of 5.0 mmol of 1-(trans-4-hexylcyclohexyl)prop-2-en-1-one [preparable by (a) reaction of trans-4-hexylcyclohexanecarbonyl chloride with AlCl$_3$ in dichloromethane and passing in of ethene to give 1-(trans-4-hexylcyclohexyl)-3-chloropropan-1-one and (b) reaction and heating with triethylamine in THF, boiling point 60°–63°/0.03 mmHg] and 5.02 mmol of 1-piperidino-2-(4-propylphenyl)-ethene (preparable by reaction of 4-propylphenylacetic acid with a mixture of diisopropylamine and n-butyllithium in THF and 4-(methoxymethylene)-piperidinium methyl sulfate analogously to R. Knorr et al., Synthesis 1983, 785) is dissolved in 10 ml of THF and stirred at room temperature for 72 hours (in accordance with C. Botteghi et al., Synth. Comm., 1979, 9(2), 69). The solvent is removed and the residue is taken up in water-ethanol (1:1, 3 ml), 22.3 mmol of hydroxylamine hydrochloride are added, and the mixture is heated for 24 hours. The solvent is removed, and the residue is taken up in ether.

The organic phase is worked up as customary to give, after purification by means of column chromatography over Al$_2$O$_3$ and recrystallization, 2-(trans-4-hexylcyclohexyl)-5-(4-propylphenyl)pyridine having C 94° S$_B$ 127° S$_A$ 134° N 147° I.

Prepared analogously:
2-(trans-4-Hexylcyclohexyl)-5-(4-ethylphenyl)pyridine
2-(trans-4-Hexylcyclohexyl)-5-(4-butylphenyl)pyridine
2-(trans-4-Hexylcyclohexyl)-5-(4-pentylphenyl)pyridine
2-(trans-4-Hexylcyclohexyl)-5-(4-hexylphenyl)pyridine
2-(trans-4-Hexylcyclohexyl)-5-(4-heptylphenyl)pyridine
2-(trans-4-Hexylcyclohexyl)-(4-octylphenyl)pyridine
2-(trans-4-Octylcyclohexyl)-5-(4-propylphenyl)pyridine
2-(trans-4-Octylcyclohexyl)-5-(4-ethylphenyl)pyridine
2-(trans-4-Octylcyclohexyl)-5-(4-butylphenyl)pyridine
2-(trans-4-Octylcyclohexyl)-5-(4-pentylphenyl)pyridine
2-(trans-4-Octylcyclohexyl)-5-(4-hexylphenyl)pyridine
2-(trans-4-Octylcyclohexyl)-5-(4-heptylphenyl)pyridine
2-(trans-4-Octylcyclohexyl)-5-(4-octylphenyl)pyridine
2-(trans-4-Heptylcyclohexyl)-5-(4-propylphenyl)pyridine
2-(trans-4-Heptylcyclohexyl)-5-(4-ethylphenyl)pyridine
2-(trans-4-Heptylcyclohexyl)-5-(4-butylphenyl)pyridine
2-(trans-4-Heptylcyclohexyl)-5-(4-pentylphenyl)pyridine
2-(trans-4-Heptylcyclohexyl)-5-(4-hexylphenyl)pyridine
2-(trans-4-Heptylcyclohexyl)-5-(4-heptylphenyl)pyridine
2-(trans-4-Heptylcyclohexyl)-5-(4-octylphenyl)pyridine
2-(trans-4-Pentylcyclohexyl)-5-(4-propylphenyl)pyridine C 58° S$_B$ 124° S$_A$ 134° N 156° I
2-(trans-4-Pentylcyclohexyl)-5-(4-ethylphenyl)pyridine
2-(trans-4-Pentylcyclohexyl)-5-(4-butylphenyl)pyridine
2-(trans-4-Pentylcyclohexyl)-5-(4-pentylphenyl)pyridine
2-(trans-4-Pentylcyclohexyl)-5-(4-hexylphenyl)pyridine
2-(trans-4-Pentylcyclohexyl)-5-(4-heptylphenyl)pyridine
2-(trans-4-Pentylcyclohexyl)-5-(4-octylphenyl)pyridine
2-(trans-4-Butylcyclohexyl)-5-(4-propylphenyl)pyridine
2-(trans-4-Butylcyclohexyl)-5-(4-ethylphenyl)pyridine
2-(trans-4-Butylcyclohexyl)-5-(4-butylphenyl)pyridine
2-(trans-4-Butylcyclohexyl)-5-(4-pentylphenyl)pyridine
2-(trans-4-Butylcyclohexyl)-5-(4-hexylphenyl)pyridine
2-(trans-4-Butylcyclohexyl)-5-(4-heptylphenyl)pyridine
2-(trans-4-Butylcyclohexyl)-5-(4-octylphenyl)pyridine
2-(trans-4-Propylcyclohexyl)-5-(4-propylphenyl)pyridine
2-(trans-4-Propylcyclohexyl)-5-(4-ethylphenyl)pyridine
2-(trans-4-Propylcyclohexyl)-5-(4-butylphenyl)pyridine
2-(trans-4-Propylcyclohexyl)-5-(4-pentylphenyl)pyridine
2-(trans-4-Propylcyclohexyl)-5-(4-hexylphenyl)pyridine
2-(trans-4-Propylcyclohexyl)-5-(4-heptylphenyl)pyridine
2-(trans-4-Propylcyclohexyl)-5-(4-octylphenyl)pyridine
2-(trans-4-Ethylcyclohexyl)-5-(4-propylphenyl)pyridine
2-(trans-4-Ethylcyclohexyl)-5-(4-ethylphenyl)pyridine
2-(trans-4-Ethylcyclohexyl)-5-(4-butylphenyl)pyridine
2-(trans-4-Ethylcyclohexyl)-5-(4-pentylphenyl)pyridine
2-(trans-4-Ethylcyclohexyl)-5-(4-hexylphenyl)pyridine
2-(trans-4-Ethylcyclohexyl)-5-(4-heptylphenyl)pyridine
2-(trans-4-Ethylcyclohexyl)-5-(4-octylphenyl)pyridine
2-(trans-4-Hexylcyclohexyl)-5-(4-propyloxyphenyl)pyridine
2-(trans-4-Hexylcyclohexyl)-5-(4-ethyloxyphenyl)pyridine C 91° S$_B$ 100° S$_A$ 147° N 190° I
2-(trans-4-Hexylcyclohexyl)-5-(4-butyloxyphenyl)pyridine
2-(trans-4-Hexylcyclohexyl)-5-(4-pentyloxyphenyl)pyridine
2-(trans-4-Hexylcyclohexyl)-5-(4-hexyloxyphenyl)pyridine
2-(trans-4-Hexylcyclohexyl)-5-(4heptyloxyphenyl)pyridine
2-(trans-4-Hexylcyclohexyl)-5-(4-octyloxyphenyl)pyridine
2-(trans-4-Octylcyclohexyl)-5-(4-propyloxyphenyl)pyridine
2-(trans-4-Octylcyclohexyl)-5-(4-ethyloxyphenyl)pyridine
2-(trans-4-Octylcyclohexyl)-5-(4-butyloxyphenyl)pyridine
2-(trans-4-Octylcyclohexyl)-5-(4-pentyloxyphenyl)pyridine
2-(trans-4-Octylcyclohexyl)-5-(4-hexyloxyphenyl)pyridine
2-(trans-4-Octylcyclohexyl)-5-(4-heptyloxyphenyl)pyridine
2-(trans-4-Octylcyclohexyl)-5-(4-octyloxyphenyl)pyridine
2-(trans-4-Pentylcyclohexyl)-5-(4-propyloxyphenyl)pyridine 2-(trans-4-Pentylcyclohexyl)-5-(4-ethyloxyphenyl)pyridine C 114° S$_A$ 134° N 194° I
2-(trans-4-Pentylcyclohexyl)-5-(4-butyloxyphenyl)pyridine
2-(trans-4-Pentylcyclohexyl)-5-(4-pentyloxyphenyl)pyridine
2-(trans-4-Pentylcyclohexyl)-5-(4-hexyloxyphenyl)pyridine
2-(trans-4-Pentylcyclohexyl)-5-(4-heptyloxyphenyl)pyridine
2-(trans-4-Pentylcyclohexyl)-5-(4-octyloxyphenyl)pyridine

EXAMPLE 12

Example 10 is repeated to obtain from 1-(2-fluoro-4-propylphenyl)-3-chloropropan-1-one (preparable from 2-fluoropropylbenzene and 3-chloropropanoyl chloride by Friedel-Crafts) and 1-piperidino-2-(trans-4-pentylcyclohexyl)-ethene (preparable in accordance with Synthesis, 1983, 785) the corresponding 5-(trans-4-pentylcyclohexyl)-2-(2-fluoro-4-propylphenyl)pyridine.

Prepared analogously:
5-(trans-4-Pentylcyclohexyl)-2-(2-fluoro-4-ethylphenyl)pyridine
5-(trans-4-Pentylcyclohexyl)-2-(2-fluoro-4-butylphenyl)pyridine
5-(trans-4-Pentylcyclohexyl)-2-(2-fluoro-4-pentylphenyl)pyridine
5-(trans-4-Pentylcyclohexyl)-2-(2-fluoro-4-hexylphenyl)pyridine
5-(trans-4-Pentylcyclohexyl)-2-(2-fluoro-4-heptylphenyl)pyridine
5-(trans-4-Pentylcyclohexyl)-2-(2-fluoro-4-octylphenyl)pyridine
5-(trans-4-Pentylcyclohexyl)-2-(2-fluoro-4-nonylphenyl)pyridine
5-(trans-4-Propylcyclohexyl)-2-(2-fluoro-4-propylphenyl)pyridine
5-(trans-4-Propylcyclohexyl)-2-(2-fluoro-4-ethylphenyl)pyridine
5-(trans-4-Propylcyclohexyl)-2-(2-fluoro-4-butylphenyl)pyridine
5-(trans-4-Propylcyclohexyl)-2-(2-fluoro-4-pentylphenyl)pyridine, C 47° N 149° I
5-(trans-4-Propylcyclohexyl)-2-(2-fluoro-4-hexylphenyl)pyridine
5-(trans-4-Propylcyclohexyl)-2-(2-fluoro-4-heptylphenyl)pyridine
5-(trans-4-Propylcyclohexyl)-2-(2-fluoro-4-octylphenyl)pyridine
5-(trans-4-Propylcyclohexyl)-2-(2-fluoro-4-nonylphenyl)pyridine
5-(trans-4-Butylcyclohexyl)-2-(2-fluoro-4-propylphenyl)pyridine
5-(trans-4-Butylcyclohexyl)-2-(2-fluoro-4-ethylphenyl)pyridine
5-(trans-4-Butylcyclohexyl)-2-(2-fluoro-4-butylphenyl)pyridine
5-(trans-4-Butylcyclohexyl)-2-(2-fluoro-4-pentylphenyl)pyridine
5-(trans-4-Butylcyclohexyl)-2-(2-fluoro-4-hexylphenyl)pyridine
5-(trans-4-Butylcyclohexyl)-2-(2-fluoro-4-heptylphenyl)pyridine
5-(trans-4-Butylcyclohexyl)-2-(2-fluoro-4-octylphenyl)pyridine
5-(trans-4-Butylcyclohexyl)-2-(2-fluoro-4-nonylphenyl)pyridine
5-(trans-4-Hexylcyclohexyl)-2-(2-fluoro-4-propylphenyl)pyridine
5-(trans-4-Hexylcyclohexyl)-2-(2-fluoro-4-ethylphenyl)pyridine
5-(trans-4-Hexylcyclohexyl)-2-(2-fluoro-4-butylphenyl)pyridine
5-(trans-4-Hexylcyclohexyl)-2-(2-fluoro-4-pentylphenyl)pyridine
5-(trans-4-Hexylcyclohexyl)-2-(2-fluoro-4-hexylphenyl)pyridine
5-(trans-4-Hexylcyclohexyl)-2-(2-fluoro-4-heptylphenyl)pyridine
5-(trans-4-Hexylcyclohexyl)-2-(2-fluoro-4-octylphenyl)pyridine
5-(trans-4-Hexylcyclohexyl)-2-(2-fluoro-4-nonylphenyl)pyridine
5-(trans-4-Heptylcyclohexyl)-2-(2-fluoro-4-propylphenyl)pyridine
5-(trans-4-Heptylcyclohexyl)-2-(2-fluoro-4-ethylphenyl)pyridine
5-(trans-4-Heptylcyclohexyl)-2-(2-fluoro-4-butylphenyl)pyridine
5-(trans-4-Heptylcyclohexyl)-2-(2-fluoro-4-pentylphenyl)pyridine
5-(trans-4-Heptylcyclohexyl)-2-(2-fluoro-4-hexylphenyl)pyridine
5-(trans-4-Heptylcyclohexyl)-2-(2-fluoro-4-heptylphenyl)pyridine
5-(trans-4-Heptylcyclohexyl)-2-(2-fluoro-4-octylphenyl)pyridine
5-(trans-4-Heptylcyclohexyl)-2-(2-fluoro-4-nonylphenyl)pyridine
5-(trans-4-Octylcyclohexyl)-2-(2-fluoro-4-propylphenyl)pyridine
5-(trans-4-Octylcyclohexyl)-2-(2-fluoro-4-ethylphenyl)pyridine
5-(trans-4-Octylcyclohexyl)-2-(2-fluoro-4-butylphenyl)pyridine
5-(trans-4-Octylcyclohexyl)-2-(2-fluoro-4-pentylphenyl)pyridine
5-(trans-4-Octylcyclohexyl)-2-(2-fluoro-4-hexylphenyl)pyridine
5-(trans-4-Octylcyclohexyl)-2-(2-fluoro-4-heptylphenyl)pyridine
5-(trans-4-Octylcyclohexyl)-2-(2-fluoro-4-octylphenyl)pyridine
5-(trans-4-Octylcyclohexyl)-2-(2-fluoro-4-nonylphenyl)pyridine
5-(trans-4-Ethylcyclohexyl)-2-(2-fluoro-4-propylphenyl)pyridine
5-(trans-4-Ethylcyclohexyl)-2-(2-fluoro-4-ethylphenyl)pyridine
5-(trans-4-Ethylcyclohexyl)-2-(2-fluoro-4-butylphenyl)pyridine
5-(trans-4-Ethylcyclohexyl)-2-(2-fluoro-4-pentylphenyl)pyridine
5-(trans-4-Ethylcyclohexyl)-2-(2-fluoro-4-hexylphenyl)pyridine
5-(trans-4-Ethylcyclohexyl)-2-(2-fluoro-4-heptylphenyl)pyridine
5-(trans-4-Ethylcyclohexyl)-2-(2-fluoro-4-octylphenyl)pyridine
5-(trans-4-Ethylcyclohexyl)-2-(2-fluoro-4-nonylphenyl)pyridine

EXAMPLE 13

Example 11 is repeated by reacting hex-1-en-3-one (preparable starting from butanoyl chloride analogously to the vinyl ketone in Example 11) and 1-piperidino-2-(4′-pentylbiphenyl-4-yl)ethene (preparable analogously to the preparation of the enamine in Example 11) to give 5-(4′-pentylbiphenyl-4-yl)-2-propylpyridine having $S_E$ 178° $S_B$ 211° $S_A$ 222° I.

Prepared analogously:
5-(4′-Pentylbiphenyl-4-yl)-2-ethylpyridine
5-(4′-Pentylbiphenyl-4-yl)-2-butylpyridine
5-(4′-Pentylbiphenyl-4-yl)-2-pentylpyridine
5-(4′-Pentylbiphenyl-4-yl)-2-hexylpyridine
5-(4′-Pentylbiphenyl-4-yl)-2-heptylpyridine
5-(4′-Pentylbiphenyl-4-yl)-2-octylpyridine
5-(4′-Pentyloxybiphenyl-4-yl)-2-propylpyridine
5-(4′-Pentyloxybiphenyl-4-yl)-2-ethylpyridine
5-(4′-Pentyloxybiphenyl-4-yl)-2-butylpyridine
5-(4′-Pentyloxybiphenyl-4-yl)-2-pentylpyridine
5-(4′-Pentyloxybiphenyl-4-yl)-2-hexylpyridine
5-(4′-Pentyloxybiphenyl-4-yl)-2-heptylpyridine
5-(4′-Pentyloxybiphenyl-4-yl)-2-octylpyridine
5-(4′-Butylbiphenyl-4-yl)-2-propylpyridine
5-(4′-Butylbiphenyl-4-yl)-2-ethylpyridine
5-(4′-Butylbiphenyl-4-yl)-2-butylpyridine
5-(4′-Butylbiphenyl-4-yl)-2-pentylpyridine
5-(4′-Butylbiphenyl-4-yl)-2-hexylpyridine
5-(4′-Butylbiphenyl-4-yl)-2-heptylpyridine
5-(4′-Butylbiphenyl-4-yl)-2-octylpyridine
5-(4′-Butyloxybiphenyl-4-yl)-2-propylpyridine
5-(4′-Butyloxybiphenyl-4-yl)-2-ethylpyridine
5-(4′-Butyloxybiphenyl-4-yl)-2-butylpyridine
5-(4′-Butyloxybiphenyl-4-yl)-2-pentylpyridine
5-(4′-Butyloxybiphenyl-4-yl)-2-hexylpyridine
5-(4′-Butyloxybiphenyl-4-yl)-2-heptylpyridine
5-(4′-Butyloxybiphenyl-4-yl)-2-octylpyridine
5-(4′-Propylbiphenyl-4-yl)-2-propylpyridine
5-(4′-Propylbiphenyl-4-yl)-2-ethylpyridine
5-(4′-Propylbiphenyl-4-yl)-2-butylpyridine
5-(4′-Propylbiphenyl-4-yl)-2-pentylpyridine
5-(4′-Propylbiphenyl-4-yl)-2-hexylpyridine
5-(4′-Propylbiphenyl-4-yl)-2-heptylpyridine
5-(4′-Propylbiphenyl-4-yl)-2-octylpyridine
5-(4′-Propyloxybiphenyl-4-yl)-2-propylpyridine
5-(4′-Propyloxybiphenyl-4-yl)-2-ethylpyridine
5-(4′-Propyloxybiphenyl-4-yl)-2-butylpyridine
5-(4′-Propyloxybiphenyl-4-yl)-2-pentylpyridine
5-(4′-Propyloxybiphenyl-4-yl)-2-hexylpyridine
5-(4′-Propyloxybiphenyl-4-yl)-2-heptylpyridine
5-(4′-Propyloxybiphenyl-4-yl)-2-octylpyridine
5-(4′-Ethylbiphenyl-4-yl)-2-propylpyridine
5-(4′-Ethylbiphenyl-4-yl)-2-ethylpyridine
5-(4′-Ethylbiphenyl-4-yl)-2-butylpyridine
5-(4′-Ethylbiphenyl-4-yl)-2-pentylpyridine
5-(4′-Ethylbiphenyl-4-yl)-2-hexylpyridine
5-(4′-Ethylbiphenyl-4-yl)-2-heptylpyridine
5-(4′-Ethylbiphenyl-4-yl)-2-octylpyridine
5-(4′-Ethyloxybiphenyl-4-yl)-2-propylpyridine
5-(4′-Ethyloxybiphenyl-4-yl)-2-ethylpyridine
5-(4′-Ethyloxybiphenyl-4-yl)-2-butylpyridine
5-(4′-Ethyloxybiphenyl-4-yl)-2-pentylpyridine
5-(4′-Ethyloxybiphenyl-4-yl)-2-hexylpyridine
5-(4′-Ethyloxybiphenyl-4-yl)-2-heptylpyridine
5-(4′-Ethyloxybiphenyl-4-yl)-2-octylpyridine
5-(4′-Hexylbiphenyl-4-yl)-2-propylpyridine
5-(4′-Hexylbiphenyl-4-yl)-2-ethylpyridine
5-(4′-Hexylbiphenyl-4-yl)-2-butylpyridine
5-(4′-Hexylbiphenyl-4-yl)-2-pentylpyridine
5-(4′-Hexylbiphenyl-4-yl)-2-hexylpyridine
5-(4′-Hexylbiphenyl-4-yl)-2-heptylpyridine
5-(4′-Hexylbiphenyl-4-yl)-2-octylpyridine
5-(4′-Heptylbiphenyl-4-yl)-2-propylpyridine
5-(4′-Heptylbiphenyl-4-yl)-2-ethylpyridine
5-(4′-Heptylbiphenyl-4-yl)-2-butylpyridine
5-(4′-Heptylbiphenyl-4-yl)-2-pentylpyridine
5-(4′-Heptylbiphenyl-4-yl)-2-hexylpyridine
5-(4′-Heptylbiphenyl-4-yl)-2-heptylpyridine
5-(4′-Heptylbiphenyl-4-yl)-2-octylpyridine
5-(2-Fluoro-4′-heptylbiphenyl-4-yl)-2-propylpyridine
5-(2-Fluoro-4′-heptylbiphenyl-4-yl)-2-ethylpyridine
5-(2-Fluoro-4′-heptylbiphenyl-4-yl)-2-butylpyridine
5-(2-Fluoro- 4′-heptylbiphenyl-4-yl)-2-pentylpyridine
5-(2-Fluoro-4′-heptylbiphenyl-4-yl)-2-hexylpyridine
5-(2-Fluoro-4′-heptylbiphenyl-4-yl)-2-heptylpyridine
5-(2-Fluoro-4′-heptylbiphenyl-4-yl)-2-octylpyridine
5-(2-Fluoro-4′-pentylbiphenyl-4-yl)-2-propylpyridine
5-(2-Fluoro 4′-pentylbiphenyl-4-yl)-2-ethylpyridine
5-(2-Fluoro-4′-pentylbiphenyl-4-yl)-2-butylpyridine
5-(2-Fluoro-4′-pentylbiphenyl-4-yl)-2-pentylpyridine
5-(2-Fluoro-4′-pentylbiphenyl-4-yl)-2-hexylpyridine
5-(2-Fluoro-4′-pentylbiphenyl-4-yl)-2-heptylpyridine
5-(2-Fluoro-4′-pentylbiphenyl-4-yl)-2-octylpyridine
5-(2-Fluoro-4′-hexylbiphenyl-4-yl)-2-propylpyridine
5-(2-Fluoro-4′-hexylbiphenyl-4-yl)-2-ethylpyridine
5-(2-Fluoro-4′-hexylbiphenyl-4-yl)-2-butylpyridine
5-(2-Fluoro-4′-hexylbiphenyl-4-yl)-2-pentylpyridine
5-(2-Fluoro-4′-hexylbiphenyl-4-yl)-2-hexylpyridine
5-(2-Fluoro-4′-hexylbiphenyl-4-yl)-2-heptylpyridine
5-(2-Fluoro-4′-hexylbiphenyl-4-yl)-2-octylpyridine
5-(2′-Fluoro-4′-butylbiphenyl-4-yl)-2-propylpyridine
5-(2′-Fluoro-4′-butylbiphenyl-4-yl)-2-ethylpyridine
5-(2′-Fluoro-4′-butylbiphenyl-4-yl)-2-butylpyridine
5-(2′-Fluoro-4′-butylbiphenyl-4-yl)-2-pentylpyridine
5-(2′-Fluoro-4′butylbiphenyl-4-yl)-2-hexylpyridine
5-(2′-Fluoro-4′-butylbiphenyl-4-yl)-2-heptylpyridine
5-(2′-Fluoro-4′-butylbiphenyl-4-yl)-2-octylpyridine
5-(2′-Fluoro-4′-propylbiphenyl-4-yl)-2-propylpyridine
5-(2′-Fluoro-4′-propylbiphenyl-4-yl)-2-ethylpyridine
5-(2′-Fluoro-4′-propylbiphenyl-4-yl)-2-butylpyridine
5-(2′-Fluoro-4′-propylbiphenyl-4-yl)-2-pentylpyridine
5-(2′-Fluoro-4′-propylbiphenyl-4-yl)-2-hexylpyridine
5-(2′-Fluoro-4′-propylbiphenyl-4-yl)-2-heptylpyridine
5-(2′-Fluoro-4′-propylbiphenyl-4-yl)-2-octylpyridine
5-(2′-Fluoro-4′-pentylbiphenyl-4-yl)-2-propylpyridine
5-(2′-Fluoro-4′-pentylbiphenyl-4-yl)-2-ethylpyridine
5-(2′-Fluoro-4′-pentylbiphenyl-4-yl)-2-butylpyridine
5-(2′-Fluoro-4′-pentylbiphenyl-4-yl)-2-pentylpyridine
5-(2′-Fluoro-4′-pentylbiphenyl-4-yl)-2-hexylpyridine
5-(2′-Fluoro-4′-pentylbiphenyl-4-yl)-2-heptylpyridine
5-(2′-Fluoro-4′-pentylbiphenyl-4-yl)-2-octylpyridine

EXAMPLE 14

Example 12 is repeated to obtain from 1-(2-fluoro-4-pentylphenyl)-3-chloropropan-1-one and 1-piperidino-2-((4-propylphenyl)-ethene (analogous preparation as in Example 11) 2-(2-fluoro-4-pentylphenyl)-5-(4-propylphenyl)pyridine.

Prepared analogously:
2-(2-Fluoro-4-pentylphenyl)-5-(4-ethylphenyl)pyridine
2-(2-Fluoro-4-pentylphenyl)-5-(4-butylphenyl)pyridine
2-(2-Fluoro-4-pentylphenyl)-5-(4-pentylphenyl)pyridine
2-(2-Fluoro-4-pentylphenyl)-5-(4-hexylphenyl)pyridine
2-(2-Fluoro-4-pentylphenyl)-5-(4-heptylphenyl)pyridine
2-(2-Fluoro-4-pentylphenyl)-5-(4-octylphenyl)pyridine
2-(2-Fluoro-4-pentylphenyl)-5-(4-nonylphenyl)pyridine
2-(2-Fluoro-4-pentylphenyl)-5-(4-ethoxyphenyl)pyridine 2-(2-Fluoro-4-pentylphenyl)-5-(4-propoxyphenyl)pyridine
2-(2-Fluoro-4-pentylphenyl)-5-(4-butoxyphenyl)pyridine
2-(2-Fluoro-4-pentylphenyl)-5-(4-pentoxyphenyl)pyridine
2-(2-Fluoro-4-pentylphenyl)-5-(4-hexoxyphenyl)pyridine
2-(2-Fluoro-4-pentylphenyl)-5-(4-heptoxyphenyl)pyridine
2-(2-Fluoro-4-pentylphenyl)-5-(4-octoxyphenyl)pyridine
2-(2-Fluoro-4-pentylphenyl)-5-(4-nonoxyphenyl)pyridine
2-(2-Fluoro-4-propylphenyl)-5-(4-propylphenyl)pyridine
2-(2-Fluoro-4-propylphenyl)-5-(4-ethylphenyl)pyridine
2-(2-Fluoro-4-propylphenyl)-5-(4-butylphenyl)pyridine
2-(2-Fluoro-4-propylphenyl)-5-(4-hexylphenyl)pyridine
2-(2-Fluoro-4-propylphenyl)-5-(4-heptylphenyl)pyridine
2-(2-Fluoro-4-propylphenyl)-5-(4-octylphenyl)pyridine
2-(2-Fluoro-4-propylphenyl)-5-(4-nonylphenyl)pyridine
2-(2-Fluoro 4-propylphenyl)-5-(4-ethoxyphenyl)pyridine
2-(2-Fluoro-4-propylphenyl)-5-(4-propoxyphenyl)pyridine
2-(2-Fluoro-4-propylphenyl)-5-(4-butoxyphenyl)pyridine
2-(2-Fluoro-4-propylphenyl)-5-(4-pentoxyphenyl)pyridine
2-(2-Fluoro-4-propylphenyl)-5-(4-hexoxyphenyl)pyridine
2-(2-Fluoro-4-propylphenyl)-5-(4-heptoxyphenyl)pyridine
2-(2-Fluoro-4-propylphenyl)-5-(4-octoxyphenyl)pyridine
2-(2-Fluoro-4-propylphenyl)-5-(4-nonoxyphenyl)pyridine
2-(2-Fluoro-4-ethylphenyl)-5-(4-propylphenyl)pyridine
2-(2-Fluoro-4-ethylphenyl)-5-(4-ethylphenyl)pyridine
2-(2-Fluoro-4-ethylphenyl)-5-(4-butylphenyl)pyridine
2-(2-Fluoro-4-ethylphenyl)-5-(4-pentylphenyl)pyridine
2-(2-Fluoro-4-ethylphenyl)-5-(4-hexylphenyl)pyridine
2-(2-Fluoro-4-ethylphenyl)-5-(4-heptylphenyl)pyridine
2-(2-Fluoro-4-ethylphenyl)-5-(4-octylphenyl)pyridine
2-(2-Fluoro-4-ethylphenyl)-5-(4-nonylphenyl)pyridine
2-(2-Fluoro-4-ethylphenyl)-5-(4-ethoxyphenyl)pyridine
2-(2-Fluoro-4-ethylphenyl)-5-(4-propoxyphenyl)pyridine
2-(2-Fluoro-4-ethylphenyl)-5-(4-butoxyphenyl)pyridine
2-(2-Fluoro-4-ethylphenyl)-5-(4-pentoxyphenyl)pyridine
2-(2-Fluoro-4-ethylphenyl)-5-(4-hexoxyphenyl)pyridine
2-(2-Fluoro-4-ethylphenyl)-5-(4-heptoxyphenyl)pyridine
2-(2-Fluoro-4-ethylphenyl)-5-(4-octoxyphenyl)pyridine
2-(2-Fluoro-4-ethylphenyl)-5-(4-nonoxyphenyl)pyridine
2-(2-Fluoro-4-butylphenyl)-5-(4-propylphenyl)pyridine
2-(2-Fluoro-4-butylphenyl)-5-(4-ethylphenyl)pyridine
2-(2-Fluoro-4-butylphenyl)-5-(4-butylphenyl)pyridine
2-(2-Fluoro-4-butylphenyl)-5-(4-pentylphenyl)pyridine
2-(2-Fluoro-4-butylphenyl)-5-(4-hexylphenyl)pyridine
2-(2-Fluoro-4-butylphenyl)-5-(4-heptylphenyl)pyridine
2-(2-Fluoro-4-butylphenyl)-5-(4-octylphenyl)pyridine
2-(2-Fluoro-4-butylphenyl)-5-(4-nonylphenyl)pyridine
2-(2-Fluoro-4-butylphenyl)-5-(4-ethoxyphenyl)pyridine
2-(2-Fluoro-4-butylphenyl)-5-(4-propoxyphenyl)pyridine
2-(2-Fluoro-4-butylphenyl)-5-(4-butoxyphenyl)pyridine
2-(2-Fluoro-4-butylphenyl)-5-(4-pentoxyphenyl)pyridine
2-(2-Fluoro-4-butylphenyl)-5-(4-hexoxyphenyl)pyridine
2-(2-Fluoro-4-butylphenyl)-5-(4-heptoxyphenyl)pyridine
2-(2-Fluoro-4-butylphenyl)-5-(4-octoxyphenyl)pyridine
2-(2-Fluoro-4-butylphenyl)-5-(4-nonoxyphenyl)pyridine
2-(2-Fluoro-4-hexylphenyl)-5-(4-propylphenyl)pyridine
2-(2-Fluoro-4-hexylphenyl)-5-(4-ethylphenyl)pyridine
2-(2-Fluoro-4-hexylphenyl)-5-(4-butylphenyl)pyridine
2-(2-Fluoro-4-hexylphenyl)-5-(4-hexylphenyl)pyridine
2-(2-Fluoro-4-hexylphenyl)-5-(4-pentylphenyl)pyridine
2-(2-Fluoro-4-hexylphenyl)-5-(4-heptylphenyl)pyridine
2-(2-Fluoro-4-hexylphenyl)-5-(4-octylphenyl)pyridine
2-(2-Fluoro-4-hexylphenyl)-5-(4-nonylphenyl)pyridine
2-(2-Fluoro-4-hexylphenyl)-5-(4-ethoxyphenyl)pyridine
2-(2-Fluoro-4-hexylphenyl)-5-(4-propoxyphenyl)pyridine
2-(2-Fluoro-4-hexylphenyl)-5-(4-butoxyphenyl)pyridine
2-(2-Fluoro-4-hexylphenyl)-5-(4-pentoxyphenyl)pyridine
2-(2-Fluoro-4-hexylphenyl)-5-(4-hexoxyphenyl)pyridine
2-(2-Fluoro-4-hexylphenyl)-5-(4-heptoxyphenyl)pyridine
2-(2-Fluoro-4-hexylphenyl)-5-(4-octoxyphenyl)pyridine
2-(2-Fluoro-4-hexylphenyl)-5-(4-nonoxyphenyl)pyridine
2-(2-Fluoro-4-heptylphenyl)-5-(4-propylphenyl)pyridine
2-(2-Fluoro-4-heptylphenyl)-5-(4-ethylphenyl)pyridine
2-(2-Fluoro-4-heptylphenyl)-5-(4-butylphenyl)pyridine
2-(2-Fluoro-4-heptylphenyl)-5-(4-pentylphenyl)pyridine
2-(2-Fluoro-4-heptylphenyl)-5-(4-hexylphenyl)pyridine
2-(2-Fluoro-4-heptylphenyl)-5-(4-heptylphenyl)pyridine
2-(2-Fluoro-4-heptylphenyl)-5-(4-octylphenyl)pyridine
2-(2-Fluoro-4-heptylphenyl)-5-(4-nonylphenyl)pyridine
2-(2-Fluoro-4-heptylphenyl)-5-(4-ethoxyphenyl)pyridine
2-(2-Fluoro-4-heptylphenyl)-5-(4-propoxyphenyl)pyridine
2-(2-Fluoro-4-heptylphenyl)-5-(4-butoxyphenyl)pyridine
2-(2-Fluoro-4-heptylphenyl)-5-(4-pentoxyphenyl)pyridine
2-(2-Fluoro-4-heptylphenyl)-5-(4-hexoxyphenyl)pyridine
2-(2-Fluoro-4-heptylphenyl)-5-(4-heptoxyphenyl)pyridine
2-(2-Fluoro-4-heptylphenyl)-5-(4-octoxyphenyl)pyridine
2-(2-Fluoro-4-heptylphenyl)-5-(4-nonoxyphenyl)pyridine
2-(2-Fluoro-4-octylphenyl)-5-(4-propylphenyl)pyridine
2-(2-Fluoro-4-octylphenyl)-5-(4-ethylphenyl)pyridine
2-(2-Fluoro-4-octylphenyl)-5-(4-butylphenyl)pyridine
2-(2-Fluoro-4-octylphenyl)-5-(4-pentylphenyl)pyridine
2-(2-Fluoro-4-octylphenyl)-5-(4-hexylphenyl)pyridine 2-(2-Fluoro-4-octylphenyl)-5-(4-heptylphenyl)pyridine
2-(2-Fluoro-4-octylphenyl)-5-(4-octylphenyl)pyridine
2-(2-Fluoro-4-octylphenyl)-5-(4-nonylphenyl)pyridine
2-(2-Fluoro-4-octylphenyl)-5-(4-ethoxyphenyl)pyridine
2-(2-Fluoro-4-octylphenyl)-5-(4-propoxyphenyl)pyridine
2-(2-Fluoro-4-octylphenyl)-5-(4-butoxyphenyl)pyridine
2-(2-Fluoro-4-octylphenyl)-5-(4-pentoxyphenyl)pyridine
2-(2-Fluoro-4-octylphenyl)-5-(4-hexoxyphenyl)pyridine
2-(2-Fluoro-4-octylphenyl)-5-(4-heptoxyphenyl)pyridine
2-(2-Fluoro-4-octylphenyl)-5-(4-octoxyphenyl)pyridine
2-(2-Fluoro-4-octylphenyl)-5-(4-nonoxyphenyl)pyridine

EXAMPLE 15

Example 11 is repeated to obtain from 1-(trans-4-hexylcylcohexyl) prop-2-en-1-one and 1-piperidino-2-(trans-4-pentylcyclohexyl) ethene (preparable in accordance with Synthesis, 1983, 785) 2-(trans-4-hexylcyclohexyl)-5-(trans-4-pentylcyclohexyl)pyridine. Prepared analogously:

2-(trans-4-Hexylcyclohexyl-5-(trans-4-ethylcyclohexyl)pyridine
2-(trans-4-Hexylcyclohexyl-5-(trans-4-propylcyclohexyl)pyridine
2-(trans-4-Hexylcyclohexyl-5-(trans-4-butylcyclohexyl)pyridine
2-(trans-4-Hexylcyclohexyl-5-(trans-4-hexylcyclohexyl)pyridine
2-(trans-4-Hexylcyclohexyl-5-(trans-4-heptylcyclohexyl)pyridine
2-(trans-4-Hexylcyclohexyl-5-(trans-4-octylcyclohexyl)pyridine
2-(trans-4-Pentylcyclohexyl-5-(trans-4-pentylcyclohexyl)pyridine
2-(trans-4-Pentylcyclohexyl-5-(trans-4-ethylcyclohexyl)pyridine
2-(trans-4-Pentylcyclohexyl-5-(trans-4-propylcyclohexyl)pyridine,C<−15° $S_B$ 157° I
2-(trans-4-Pentylcyclohexyl-5-(trans-4-butylcyclohexyl)pyridine
2-(trans-4-Pentylcyclohexyl-5-(trans-4-hexylcyclohexyl)pyridine
2-(trans-4-Pentylcyclohexyl-5-(trans-4-heptylcyclohexyl)pyridine
2-(trans-4-Pentylcyclohexyl-5-(trans-4-octylcyclohexyl)pyridine
2-(trans-4-Butylcyclohexyl-5-(trans-4-pentylcyclohexyl)pyridine
2-(trans-4-Butylcyclohexyl-5-(trans-4-ethylcyclohexyl)pyridine
2-(trans-4-Butylcyclohexyl-5-(trans-4-propylcyclohexyl)pyridine
2-(trans-4-Butylcyclohexyl-5-(trans-4-butylcyclohexyl)pyridine
2-(trans-4-Butylcyclohexyl-5-(trans-4-hexylcyclohexyl)pyridine
2-(trans-4-Butylcyclohexyl-5-(trans-4-heptylcyclohexyl)pyridine
2-(trans-4-Butylcyclohexyl-5-(trans-4-octylcyclohexyl)pyridine
2-(trans-4-Propylcyclohexyl-5-(trans-4-pentylcyclohexyl)pyridine
2-(trans-4-Propylcyclohexyl-5-(trans-4-ethylcyclohexyl)pyridine
2-(trans-4-Propylcyclohexyl-5-(trans-4-propylcyclohexyl)pyridine
2-(trans-4-Propylcyclohexyl-5-(trans-4-butylcyclohexyl)pyridine
2-(trans-4-Propylcyclohexyl-5-(trans-4-hexylcyclohexyl)pyridine
2-(trans-4-Propylcyclohexyl-5-(trans-4-heptylcyclohexyl)pyridine
2-(trans-4-Propylcyclohexyl-5-(trans-4-octylcyclohexyl)pyridine
2-(trans-4-Ethylcyclohexyl-5-(trans-4-pentylcyclohexyl)pyridine
2-(trans-4-Ethylcyclohexyl-5-(trans-4-ethylcyclohexyl)pyridine
2-(trans-4-Ethylcyclohexyl-5-(trans-4-propylcyclohexyl)pyridine
2-(trans-4-Ethylcyclohexyl-5-(trans-4-butylcyclohexyl)pyridine
2-(trans-4-Ethylcyclohexyl-5-(trans-4-hexylcyclohexyl)pyridine
2-(trans-4-Ethylcyclohexyl-5-(trans-4-heptylcyclohexyl)pyridine
2-(trans-4-Ethylcyclohexyl-5-(trans-4-octylcyclohexyl)pyridine

EXAMPLE 16

46 ml of a 2.2 molar solution of phenyllithium in cyclohexane/diethyl ether (7:3) are added with ice cooling to a solution of 14.9 g of 5-butyl-2-picoline in 50 ml of diethyl ether. After 1 hour of stirring, 15.9 g of 4-ethoxybenzyl chloride in 50 ml of diethyl ether are then added at room temperature, and the ether starts to boil. The reaction mixture is poured onto ice after 1 hour, and the organic phase is worked up. Separation by column chromatography (silica gel, toluene) and recrystallization gives 2-(p-ethoxyphenylethyl)-5-butylpyridine.

Prepared analogously:
2-(p-Propoxyphenylethyl)-5-butylpyridine
2-(p-Butoxyphenylethyl)-5-butylpyridine
2-(p-Pentoxyphenylethyl)-5-butylpyridine
2-(p-Hexoxyphenylethyl)-5-butylpyridine
2-(p-Heptoxyphenylethyl)-5-butylpyridine
2-(p-Octoxyphenylethyl)-5-butylpyridine
2-(p-Nonoxyphenylethyl)-5-butylpyridine
2-(p-Methoxyphenylethyl)-5-butylpyridine
2-(p-Ethoxyphenylethyl)-5-propylpyridine
2-(p-Propoxyphenylethyl)-5-propylpyridine
2-(p-Butoxyphenylethyl)-5-propylpyridine
2-(p-Pentoxyphenylethyl)-5-propylpyridine
2-(p-Hexoxyphenylethyl)-5-propylpyridine
2-(p-Heptoxyphenylethyl)-5-propylpyridine
2-(p-Octoxyphenylethyl)-5-propylpyridine
2-(p-Nonoxyphenylethyl)-5-propylpyridine
2-(p-Methoxyphenylethyl)-5-propylpyridine
2-(p-Ethoxyphenylethyl)-5-ethylpyridine
2-(p-Propoxyphenylethyl)-5-ethylpyridine
2-(p-Butoxyphenylethyl)-5-ethylpyridine
2-(p-Pentoxyphenylethyl)-5-ethylpyridine
2-(p-Hexoxyphenylethyl)-5-ethylpyridine
2-(p-Heptoxyphenylethyl)-5-ethylpyridine
2-(p-Octoxyphenylethyl)-5-ethylpyridine
2-(p-Nonoxyphenylethyl)-5-ethylpyridine
2-(p-Methoxyphenylethyl)-5-ethylpyridine
2-(p-Ethoxyphenylethyl)-5-pentylpyridine
2-(p-Propoxyphenylethyl)-5-pentylpyridine
2-(p-Butoxyphenylethyl)-5-pentylpyridine
2-(p-Pentoxyphenylethyl)-5-pentylpyridine 2-(p-Hexoxyphenylethyl)-5-pentylpyridine
2-(p-Heptoxyphenylethyl)-5-pentylpyridine
2-(p-Octoxyphenylethyl)-5-pentylpyridine
2-(p-Nonoxyphenylethyl)-5-pentylpyridine
2-(p-Methoxyphenylethyl)-5-pentylpyridine
2-(p-Ethoxyphenylethyl)-5-hexylpyridine
2-(p-Propoxyphenylethyl)-5-hexylpyridine
2-(p-Butoxyphenylethyl)-5-hexylpyridine
2-(p-Pentoxyphenylethyl)-5-hexylpyridine
2-(p-Hexoxyphenylethyl)-5-hexylpyridine
2-(p-Heptoxyphenylethyl)-5-hexylpyridine
2-(p-Octoxyphenylethyl)-5-hexylpyridine
2-(p-Nonoxyphenylethyl)-5-hexylpyridine
2-(p-Methoxyphenylethyl)-5-hexylpyridine
2-(p-Ethoxyphenylethyl)-5-heptylpyridine
2-(p-Propoxyphenylethyl)-5-heptylpyridine
2-(p-Butoxyphenylethyl)-5-heptylpyridine
2-(p-Pentoxyphenylethyl)-5-heptylpyridine
2-(p-Hexoxyphenylethyl)-5-heptylpyridine
2-(p-Heptoxyphenylethyl)-5-heptylpyridine
2-(p-Octoxyphenylethyl)-5-heptylpyridine
2-(p-Nonoxyphenylethyl)-5-heptylpyridine
2-(p-Methoxyphenylethyl)-5-heptylpyridine
2-(p-Ethoxyphenylethyl)-5-octylpyridine
2-(p-Propoxyphenylethyl)-5-octylpyridine
2-(p-Butoxyphenylethyl)-5-octylpyridine
2-(p-Pentoxyphenylethyl)-5-octylpyridine
2-(p-Hexoxyphenylethyl)-5-octylpyridine
2-(p-Heptoxyphenylethyl)-5-octylpyridine
2-(p-Octoxyphenylethyl)-5-octylpyridine
2-(p-Nonoxyphenylethyl)-5-octylpyridine
2-(p-Methoxyphenylethyl)-5-octylpyridine
2-(p-Ethoxyphenylethyl)-5-nonylpyridine
2-(p-Propoxyphenylethyl)-5-nonylpyridine
2-(p-Butoxyphenylethyl)-5-nonylpyridine
2-(p-Pentoxyphenylethyl)-5-nonylpyridine
2-(p-Hexoxyphenylethyl)-5-nonylpyridine
2-(p-Heptoxyphenylethyl)-5-nonylpyridine
2-(p-Octoxyphenylethyl)-5-nonylpyridine
2-(p-Nonoxyphenylethyl)-5-nonylpyridine
2-(p-Methoxyphenylethyl)-5-nonylpyridine
2-(p-Ethoxyphenylethyl)-5-decylpyridine
2-(p-Propoxyphenylethyl)-5-decylpyridine
2-(p-Butoxyphenylethyl)-5-decylpyridine
2-(p-Pentoxyphenylethyl)-5-decylpyridine
2-(p-Hexoxyphenylethyl)-5-decylpyridine
2-(p-Heptoxyphenylethyl)-5-decylpyridine
2-(p-Octoxyphenylethyl)-5-decylpyridine
2-(p-Nonoxyphenylethyl)-5-decylpyridine
2-(p-Methoxyphenylethyl)-5-decylpyridine
2-(4'-Ethoxybiphenyl-4-ylethyl)-5-butylpyridine
2-(4'-Propoxybiphenyl-4-ylethyl)-5-butylpyridine
2-(4'-Butoxybiphenyl-4-ylethyl)-5-butylpyridine
2-(4'-Pentoxybiphenyl-4-ylethyl)-5-butylpyridine
2-(4'-Hexoxybiphenyl-4-ylethyl)-5-butylpyridine
2-(4'-Heptoxybiphenyl-4-ylethyl)-5-butylpyridine
2-(4'-Octoxybiphenyl-4-ylethyl)-5-butylpyridine
2(4'-Nonoxybiphenyl-4ylethyl)-5-butylpyridine
2-(4'-Methoxybiphenyl-4-ylethyl)-5-butylpyridine
2-(4'-Ethoxybiphenyl-4-ylethyl)-5-propylpyridine
2-(4'-Propoxybiphenyl-4-ylethyl)-5-propylpyridine
2-(4'-Butoxybiphenyl-4-ylethyl)-5-propylpyridine
2-(4'-Pentoxybiphenyl-4-ylethyl)-5-propylpyridine
2-(4'-Hexoxybiphenyl-4-ylethyl)-5-propylpyridine
2-(4'-Heptoxybiphenyl-4-ylethyl)-5-propylpyridine
2-(4'-Octoxybiphenyl-4-ylethyl)-5-propylpyridine
2-(4'-Nonoxybiphenyl-4-ylethyl)-5-propylpyridine
2-(4'-Methoxybiphenyl-4-ylethyl)-5-propylpyridine
2-(4'-Ethoxybiphenyl-4-ylethyl)-5-pentylpyridine
2-(4'-Propoxybiphenyl-4-ylethyl)-5-pentylpyridine
2-(4'-Butoxybiphenyl-4-ylethyl)-5-pentylpyridine
2-(4'-Pentoxybiphenyl-4-ylethyl)-5-pentylpyridine
2-(4'-Hexoxybiphenyl-4-ylethyl)-5-pentylpyridine
2-(4'-Heptoxybiphenyl-4-ylethyl)-5-pentylpyridine
2-(4'-Octoxybiphenyl-4-ylethyl)-5-pentylpyridine
2-(4'-Nonoxybiphenyl-4-ylethyl)-5-pentylpyridine
2-(4'-Methoxybiphenyl-4-ylethyl)-5-pentylpyridine
2-(4'-Ethoxybiphenyl-4-ylethyl)-5-hexylpyridine
2-(4'-Propoxybiphenyl-4-ylethyl)-5-hexylpyridine
2-(4'-Butoxybiphenyl-4-ylethyl)-5-hexylpyridine
2-(4'-Pentoxybiphenyl-4-ylethyl)-5-hexylpyridine
2-(4'-Hexoxybiphenyl-4-ylethyl)-5-hexylpyridine
2-(4'-Heptoxybiphenyl-4-ylethyl)-5-hexylpyridine
2-(4'-Octoxybiphenyl-4-ylethyl)-5-hexylpyridine
2-(4'-Nonoxybiphenyl-4-ylethyl)-5-hexylpyridine
2-(4'-Methoxybiphenyl-4-ylethyl)-5-hexylpyridine
2-(4'-Ethoxybiphenyl-4-ylethyl)-5-heptylpyridine
2-(4'-Propoxybiphenyl-4-ylethyl)-5-heptylpyridine
2-(4'-Butoxybiphenyl-4-ylethyl)-5-heptylpyridine
2-(4'-Pentoxybiphenyl-4-ylethyl)-5-heptylpyridine
2-(4'-Hexoxybiphenyl-4-ylethyl)-5-heptylpyridine
2-(4'-Heptoxybiphenyl-4-ylethyl)-5-heptylpyridine
2-(4'-Octoxybiphenyl-4-ylethyl)-5-heptylpyridine
2-(4'-Nonoxybiphenyl-4-ylethyl)-5-heptylpyridine
2-(4'-Methoxybiphenyl-4-ylethyl)-5-heptylpyridine
2-(4'-Ethoxybiphenyl-4-ylethyl)-5-ethylpyridine
2-(4'-Propoxybiphenyl-4-ylethyl)-5-ethylpyridine
2-(4'-Butoxybiphenyl-4-ylethyl)-5-ethylpyridine
2-(4'-Pentoxybiphenyl-4-ylethyl)-5-ethylpyridine
2-(4'-Hexoxybiphenyl-4-ylethyl)-5-ethylpyridine
2-(4'-Heptoxybiphenyl-4-ylethyl)-5-ethylpyridine
2-(4'-Octoxybiphenyl-4-ylethyl)-5-ethylpyridine
2-(4'-Nonoxybiphenyl-4-ylethyl)-5-ethylpyridine
2-(4'-Methoxybiphenyl-4-ylethyl)-5-ethylpyridine Starting from 2-substituted 5-picolines and 1-alkyl-4-trans-chloromethylcyclohexenes, the same method produces the following compounds:

2-p-Ethylphenyl-5-(trans-4-ethylcyclohexylethyl)pyridine
2-p-Propylphenyl-5-(trans-4-ethylcyclohexylethyl)pyridine
2-p-Butylphenyl-5-(trans-4-ethylcyclohexylethyl)pyridine
2-p-Pentylphenyl-5-(trans-4-ethylcyclohexylethyl)pyridine
2-p-Hexylphenyl-5-(trans-4-ethylcyclohexylethyl)pyridine
2-p-Heptylphenyl-5-(trans-4-ethylcyclohexylethyl)pyridine
2-p-Octylphenyl-5-(trans-4-ethylcyclohexylethyl)pyridine
2-p-Ethoxyphenyl-5-(trans-4-ethylcyclohexylethyl)pyridine
2-p-Propoxyphenyl-5-(trans-4-ethylcyclohexylethyl)pyridine
2-p-Butoxyphenyl-5-(trans-4-ethylcyclohexylethyl)pyridine
2-p-Pentoxyphenyl-5-(trans-4-ethylcyclohexylethyl)pyridine
2-p-Hexoxyphenyl-5-(trans-4-ethylcyclohexylethyl)pyridine
2-p-Heptoxyphenyl-5-(trans-4-ethylcyclohexylethyl)pyridine
2-p-Octoxyphenyl-5-(trans-4-ethylcyclohexylethyl)pyridine 2-p-Ethylphenyl-5-(trans-4-propylcyclohexylethyl)-pyridine
2-p-Propylphenyl-5-(trans-4-propylcyclohexylethyl)-pyridine
2-p-Butylphenyl-5-(trans-4-propylcyclohexylethyl)-pyridine
2-p-Pentylphenyl-5-(trans-4-propylcyclohexylethyl)-pyridine
2-p-Hexylphenyl-5-(trans-4-propylcyclohexylethyl)-pyridine
2-p-Heptylphenyl-5-(trans-4-propylcyclohexylethyl)-pyridine
2-p-Octylphenyl-5-(trans-4-propylcyclohexylethyl)-pyridine
2-p-Ethoxyphenyl-5-(trans-4-propylcyclohexylethyl)-pyridine
2-p-Propoxyphenyl-5-(trans-4-propylcyclohexylethyl)-pyridine
2-p-Butoxyphenyl-5-(trans-4-propylcyclohexylethyl)-pyridine
2-p-Pentoxyphenyl-5-(trans-4-propylcyclohexylethyl)-pyridine
2-p-Hexoxyphenyl-5-(trans-4-propylcyclohexylethyl)-pyridine
2-p-Heptoxyphenyl-5-(trans-4-propylcyclohexylethyl)-pyridine
2-p-Octoxyphenyl-5-(trans-4-propylcyclohexylethyl)-pyridine
2-p-Ethylphenyl-5-(trans-4-butylcyclohexylethyl)pyridine
2-p-Propylphenyl-5-(trans-4-butylcyclohexylethyl)-pyridine
2-p-Butylphenyl-5-(trans-4-butylcyclohexylethyl)pyridine
2-p-Pentylphenyl-5-(trans-4-butylcyclohexylethyl)pyridine
2-p-Hexylphenyl-5-(trans-4-butylcyclohexylethyl)pyridine
2-p-Heptylphenyl-5-(trans-4-butylcyclohexylethyl)-pyridine
2-p-Octylphenyl-5-(trans-4-butylcyclohexylethyl)pyridine
2-p-Ethoxyphenyl-5-(trans-4-butylcyclohexylethyl)-pyridine
2-p-Propoxyphenyl-5-(trans-4-butylcyclohexylethyl)-pyridine
2-p-Butoxyphenyl-5-(trans-4-butylcyclohexylethyl)-pyridine
2-p-Pentoxyphenyl-5-(trans-4-butylcyclohexylethyl)-pyridine
2-p-Hexoxyphenyl-5-(trans-4-butylcyclohexylethyl)-pyridine
2-p-Heptoxyphenyl-5-(trans-4-butylcyclohexylethyl)-pyridine
2-p-Octoxyphenyl-5-(trans-4-butylcyclohexylethyl)-pyridine
2-p-Ethylphenyl-5-(trans-4-pentylcyclohexylethyl)-pyridine
2-p-Propylphenyl-5-(trans-4-pentylcyclohexylethyl)-pyridine,C 52° $S_B$ 133° $S_A$ 150° I
2-p-Butylphenyl-5-(trans-4-pentylcyclohexylethyl)pyridine
2-p-Pentylphenyl-5-(trans-4-pentylcyclohexylethyl)-pyridine
2-p-Hexylphenyl-5-(trans-4-pentylcyclohexylethyl)-pyridine
2-p-Heptylphenyl-5-(trans-4-pentylcyclohexylethyl)-pyridine
2-p-Octylphenyl-5-(trans-4-pentylcyclohexylethyl)-pyridine
2-p-Ethoxyphenyl-5-(trans-4-pentylcyclohexylethyl)-pyridine
2-p-Propoxyphenyl-5-(trans-4-pentylcyclohexylethyl)-pyridine
2-p-Butoxyphenyl-5-(trans-4-pentylcyclohexylethyl)-pyridine
2-p-Pentoxyphenyl-5-(trans-4-pentylcyclohexylethyl)-pyridine
2-p-Hexoxyphenyl-5-(trans-4-pentylcyclohexylethyl)-pyridine
2-p-Heptoxyphenyl-5-(trans-4-pentylcyclohexylethyl)-pyridine
2-p-Octoxyphenyl-5-(trans-4-pentylcyclohexylethyl)-pyridine
2-p-Ethylphenyl-5-(trans-4-hexylcyclohexylethyl)pyridine
2-p-Propylphenyl-5-(trans-4-hexylcyclohexylethyl)-pyridine
2-p-Butylphenyl-5-(trans-4-hexylcyclohexylethyl)pyridine
2-p-Pentylphenyl-5-(trans-4-hexylcyclohexylethyl)-pyridine
2-p-Hexylphenyl-5-(trans-4-hexylcyclohexylethyl)pyridine
2-p-Heptylphenyl-5-(trans-4-hexylcyclohexylethyl)-pyridine
2-p-Octylphenyl-5-(trans-4-hexylcyclohexylethyl)pyridine
2-p-Ethoxyphenyl-5-(trans-4-hexylcyclohexylethyl)-pyridine
2-p-Propoxyphenyl-5-(trans-4-hexylcyclohexylethyl)-pyridine
2-p-Butoxyphenyl-5-(trans-4-hexylcyclohexylethyl)-pyridine
2-p-Pentoxyphenyl-5-(trans-4-hexylcyclohexylethyl)-pyridine
2-p-Hexoxyphenyl-5-(trans-4-hexylcyclohexylethyl)-pyridine
2-p-Heptoxyphenyl-5-(trans-4-hexylcyclohexylethyl)-pyridine
2-p-Octoxyphenyl-5-(trans-4-hexylcyclohexylethyl)-pyridine
2-p-Ethylphenyl-5-(trans-4-heptylcyclohexylethyl)-pyridine
2-p-Propylphenyl-5-(trans-4-heptylcyclohexylethyl)-pyridine
2-p-Butylphenyl-5-(trans-4-heptylcyclohexylethyl)pyridine
2-p-Pentylphenyl-5-(trans-4-heptylcyclohexylethyl)-pyridine
2-p-Hexylphenyl-5-(trans-4-heptylcyclohexylethyl)-pyridine
2-p-Heptylphenyl-5-(trans-4-heptylcyclohexylethyl)-pyridine
2-p-Octylphenyl-5-(trans-4-heptylcyclohexylethyl)-pyridine
2-p-Ethoxyphenyl-5-(trans-4-heptylcyclohexylethyl)-pyridine
2-p-Propoxyphenyl-5-(trans-4-heptylcyclohexylethyl)-pyridine
2-p-Butoxyphenyl-5-(trans-4-heptylcyclohexylethyl)-pyridine
2-p-Pentoxyphenyl-5-(trans-4-heptylcyclohexylethyl)-pyridine
2-p-Hexoxyphenyl-5-(trans-4-heptylcyclohexylethyl)-pyridine 2-p-Heptoxyphenyl-5-(trans-4-heptylcyclohexylethyl)-pyridine
2-p-Octoxyphenyl-5-(trans-4-heptylcyclohexylethyl)-pyridine
2-p-Ethylphenyl-5-(trans-4-octylcyclohexylethyl)pyridine
2-p-Propylphenyl-5-(trans-4-octylcyclohexylethyl)-pyridine
2-p-Butylphenyl-5-(trans-4-octylcyclohexylethyl)pyridine
2-p-Pentylphenyl-5-(trans-4-octylcyclohexylethyl)pyridine
2-p-Hexylphenyl-5-(trans-4-octylcyclohexylethyl)pyridine
2-p-Heptylphenyl-5-(trans-4-octylcyclohexylethyl)-pyridine
2-p-Octylphenyl-5-(trans-4-octylcyclohexylethyl)pyridine
2-p-Ethoxyphenyl-5-(trans-4-octylcyclohexylethyl)-pyridine
2-p-Propoxyphenyl-5-(trans-4-octylcyclohexylethyl)-pyridine
2-p-Butoxyphenyl-5-(trans-4-octylcyclohexylethyl)-pyridine
2-p-Pentoxyphenyl-5-(trans-4-octylcyclohexylethyl)-pyridine
2-p-Hexoxyphenyl-5-(trans-4-octylcyclohexylethyl)-pyridine .
2-p-Heptoxyphenyl-5-(trans-4-octylcyclohexylethyl)-pyridine
2-p-Octoxyphenyl-5-(trans-4-octylcyclohexylethyl)-pyridine

EXAMPLE 17

A mixture of 21.5 g of 2-bromo-1-(4-methoxyphenyl)ethane and 100 ml of toluene has added to it, under argon, 13.2 g of ZnBr$_2$ and 1.4 g of lithium and is treated for 1 hour with ultrasound. A mixture of 21.4 g of 2-butyl-5-bromopyridine and 50 ml of toluene is then added, followed by a solution of 0.2 g of nickel(II) acetonylacetonate in 20 ml of THF. After a further hour 100 ml of dilute hydrochloric acid are added a little at a time, and the organic phase is worked up. Separation by column chromatography (silica gel, toluene) and recrystallization gives 5-(p-methoxyphenylethyl)-2-butyl-pyridine.

Prepared analogously:
5-(p-Ethoxyphenylethyl)-2-butylpyridine
5-(p-Propoxyphenylethyl)-2-butylpyridine
5-(p-Butoxyphenylethyl)-2-butylpyridine
5-(p-Pentoxyphenylethyl)-2-butylpyridine
5-(p-Hexoxyphenylethyl)-2-butylpyridine
5-(p-Heptoxyphenylethyl)-2-butylpyridine
5-(p-Octoxyphenylethyl)-2-butylpyridine
5-(p-Ethoxyphenylethyl)-2-ethylpyridine
5-(p-Propoxyphenylethyl)-2-ethylpyridine
5-(p-Butoxyphenylethyl)-2-ethylpyridine
5-(p-Pentoxyphenylethyl)-2-ethylpyridine
5-(p-Hexoxyphenylethyl)-2-ethylpyridine
5-(p-Heptoxyphenylethyl)-2-ethylpyridine
5-(p-Octoxyphenylethyl)-2-ethylpyridine
5-(p-Methoxyphenylethyl)-2-propylpyridine
5-(p-Ethoxyphenylethyl)-2-propylpyridine
5-(p-Propoxyphenylethyl)-2-propylpyridine
5-(p-Butoxyphenylethyl)-2-propylpyridine
5-(p-Pentoxyphenylethyl)-2-propylpyridine
5-(p-Hexoxyphenylethyl)-2-propylpyridine
5-(p-Heptoxyphenylethyl)-2-propylpyridine
5-(p-Octoxyphenylethyl)-2-propylpyridine
5-(p-Methoxyphenylethyl)-2-pentylpyridine
5-(p-Ethoxyphenylethyl)-2-pentylpyridine
5-(p-Propoxyphenylethyl)-2-pentylpyridine
5-(p-Butoxyphenylethyl)-2-pentylpyridine
5-(p-Pentoxyphenylethyl)-2-pentylpyridine
5-(p-Hexoxyphenylethyl)-2-pentylpyridine
5-(p-Heptoxyphenylethyl)-2-pentylpyridine
5-(p-Octoxyphenylethyl)-2-pentylpyridine
5-(p-Methoxyphenylethyl)-2-hexylpyridine
5-(p-Ethoxyphenylethyl)-2-hexylpyridine
5-(p-Propoxyphenylethyl)-2-hexylpyridine
5-(p-Butoxyphenylethyl)-2-hexylpyridine
5-(p-Pentoxyphenylethyl)-2-hexylpyridine
5-(p-Hexoxyphenylethyl)-2-hexylpyridine
5-(p-Heptoxyphenylethyl)-2-hexylpyridine
5-(p-Octoxyphenylethyl)-2-hexylpyridine
5-(p-Methoxyphenylethyl)-2-heptylpyridine
5-(p-Ethoxyphenylethyl)-2-heptylpyridine
5-(p-Propoxyphenylethyl)-2-heptylpyridine
5-(p-Butoxyphenylethyl)-2-heptylpyridine
5-(p-Pentoxyphenylethyl)-2-heptylpyridine
5-(p-Hexoxyphenylethyl)-2-heptylpyridine
5-(p-Heptoxyphenylethyl)-2-heptylpyridine
5-(p-Octoxyphenylethyl)-2-heptylpyridine
5-(4'-Methoxybiphenyl-4-ylethyl)-2-butylpyridine
5-(4'-Ethoxybiphenyl-4-ylethyl)-2-butylpyridine
5-(4'-Propoxybiphenyl-4-ylethyl)-2-butylpyridine
5-(4'-Butoxybiphenyl-4-ylethyl)-2-butylpyridine
5-(4'-Pentoxybiphenyl-4-ylethyl)-2-butylpyridine
5-(4'-Hexoxybiphenyl-4-ylethyl)-2-butylpyridine
5-(4'-Heptoxybiphenyl-4-ylethyl)-2-butylpyridine
5-(4'-Octoxybiphenyl-4-ylethyl)-2-butylpyridine
5-(4'-Methoxybiphenyl-4-ylethyl)-2-propylpyridine
5-(4'-Ethoxybiphenyl-4-ylethyl)-2-propylpyridine
5-(4'-Propoxybiphenyl-4-ylethyl)-2-propylpyridine
5-(4'-Butoxybiphenyl-4-ylethyl)-2-propylpyridine
5-(4'-Pentoxybiphenyl-4-ylethyl)-2-propylpyridine
5-(4'-Hexoxybiphenyl-4-ylethyl)-2-propylpyridine
5-(4'-Heptoxybiphenyl-4-ylethyl)-2-propylpyridine
5-(4'-Octoxybiphenyl-4-ylethyl)-2-propylpyridine
5-(4'-Methoxybiphenyl-4-ylethyl)-2-pentylpyridine
5-(4'-Ethoxybiphenyl-4-ylethyl)-2-pentylpyridine
5-(4'-Propoxybiphenyl-4-ylethyl)-2-pentylpyridine
5-(4'-Butoxybiphenyl-4-ylethyl)-2-pentylpyridine
5-(4'-Pentoxybiphenyl-4-ylethyl)-2-pentylpyridine
5-(4'-Hexoxybiphenyl-4-ylethyl)-2-pentylpyridine
5-(4'-Heptoxybiphenyl-4-ylethyl)-2-pentylpyridine
5-(4'-Octoxybiphenyl-4-ylethyl)-2-pentylpyridine
5-(4'-Methoxybiphenyl-4-ylethyl)-2-hexylpyridine
5-(4'-Ethoxybiphenyl-4-ylethyl)-2-hexylpyridine
5-(4'-Propoxybiphenyl-4-ylethyl)-2-hexylpyridine
5-(4'-Butoxybiphenyl-4-ylethyl)-2-hexylpyridine
5-(4'-Pentoxybiphenyl-4-ylethyl)-2-hexylpyridine
5-(4'-Hexoxybiphenyl-4-ylethyl)-2-hexylpyridine
5-(4'-Heptoxybiphenyl-4-ylethyl)-2-hexylpyridine
5-(4'-Octoxybiphenyl-4-ylethyl)-2-hexylpyridine
5-(4'-Methoxybiphenyl-4-ylethyl)-2-heptylpyridine
5-(4'-Ethoxybiphenyl-4-ylethyl)-2-heptylpyridine
5-(4'-Propoxybiphenyl-4-ylethyl)-2-heptylpyridine
5-(4'-Butoxybiphenyl-4-ylethyl)-2-heptylpyridine
5-(4'-Pentoxybiphenyl-4-ylethyl)-2-heptylpyridine
5-(4'-Hexoxybiphenyl-4-ylethyl)-2-heptylpyridine
5-(4'-Heptoxybiphenyl-4-ylethyl)-2-heptylpyridine
5-(4'-Octoxybiphenyl-4-ylethyl)-2-heptylpyridine

EXAMPLE 18

Example 11 is repeated by reacting 1-(4'-pentylbiphenyl-4-yl)-prop-2-en-1-one and 1-piperidinopentene to give the corresponding 2-(4'-pentylbiphenyl-4-yl)-5-propylpyridine having C 171° N 198° I.

Prepared analogously:
2-(4'-Propylbiphenyl-4-yl)-5-propylpyridine
2-(4'-Butylbiphenyl-4-yl)-5-propylpyridine
2-(4'-Hexylbiphenyl-4-yl)-5-propylpyridine
2-(4'-Heptylbiphenyl-4-yl)-5-propylpyridine
2-(4'-Propoxybiphenyl-4-yl)-5-propylpyridine
2-(4'-Butoxybiphenyl-4-yl)-5-propylpyridine
2-(4'-Pentoxybiphenyl-4-yl)-5-propylpyridine
2-(4'-Hexoxybiphenyl-4-yl)-5-propylpyridine
2-(4'-Heptoxybiphenyl-4-yl)-5-propylpyridine
2-(4'-Propylbiphenyl4-yl)-5-butylpyridine
2-(4'-Butylbiphenyl-4-yl)-5-butylpyridine
2-(4'-Hexylbiphenyl-4-yl)-5-butylpyridine
2-(4'-Heptylbiphenyl-4-yl)-5-butylpyridine
2-(4'-Propoxybiphenyl-4-yl)-5-butylpyridine
2-(4'-Butoxybiphenyl-4-yl)-5-butylpyridine
2-(4'-Pentoxybiphenyl-4-yl)-5-butylpyridine
2-(4'-Hexoxybiphenyl-4-yl)-5-butylpyridine
2-(4'-Heptoxybiphenyl-4-yl)-5-butylpyridine
2-(4'-Propylbiphenyl-4-yl)-5-pentylpyridine
2-(4'-Butylbiphenyl-4-yl)-5-pentylpyridine
2-(4'-Hexylbiphenyl-4-yl)-5-pentylpyridine
2-(4'-Heptylbiphenyl-4-yl)-5-pentylpyridine
2-(4'-Propoxybiphenyl-4-yl)-5-pentylpyridine
2-(4'-Butoxybiphenyl-4-yl)-5-pentylpyridine
2-(4'-Pentoxybiphenyl-4-yl)-5-pentylpyridine
2-(4'-Hexoxybiphenyl-4-yl)-5-pentylpyridine
2-(4'-Heptoxybiphenyl-4-yl)-5-pentylpyridine
2-(4'-Propylbiphenyl-4-yl)-5-hexylpyridine
2-(4'-Butylbiphenyl-4-yl)-5-hexylpyridine
2-(4'-Hexylbiphenyl-4-yl)-5-hexylpyridine
2-(4'-Heptylbiphenyl-4-yl)-5-hexylpyridine
2-(4'-Propoxybiphenyl-4-yl)-5-hexylpyridine
2-(4'-Butoxybiphenyl-4-yl)-5-hexylpyridine
2-(4'-Pentoxybiphenyl-4-yl)-5-hexylpyridine
2-(4'-Hexoxybiphenyl-4-yl)-5-hexylpyridine
2-(4'-Heptoxybiphenyl-4-yl)-5-hexylpyridine
2-(4'-Propylbiphenyl-4-yl)-5-heptylpyridine
2-(4'-Butylbiphenyl-4-yl)-5-heptylpyridine
2-(4'-Hexylbiphenyl-4-yl)-5-heptylpyridine
2-(4'-Heptylbiphenyl-4-yl)-5-heptylpyridine
2-(4'-Propoxybiphenyl-4-yl)-5-heptylpyridine
2-(4'-Butoxybiphenyl-4-yl)-5-heptylpyridine
2-(4'-Pentoxybiphenyl-4-yl)-5-heptylpyridine
2-(4'-Hexoxybiphenyl-4-yl)-5-heptylpyridine
2-(4'-Heptoxybiphenyl-4-yl)-5-heptylpyridine
2-(2'-Fluoro-4'-pentylbiphenyl-4-yl)-5-propylpyridine, C 50° N 138° I
2-(2'-Fluoro-4'-propylbiphenyl-4-yl)-5-propylpyridine
2-(2'-Fluoro-4'-butylbiphenyl-4-yl)-5-propylpyridine
2-(2'-Fluoro-4'-hexylbiphenyl-4-yl)-5-propylpyridine
2-(2'-Fluoro-4'-heptylbiphenyl-4-yl)-5-propylpyridine
2-(2'-Fluoro-4'-propoxybiphenyl-4-yl)-5-propylpyridine
2-(2'-Fluoro-4'-butoxybiphenyl-4-yl)-5-propylpyridine
2-(2'-Fluoro-4'-pentoxybiphenyl-4-yl)-5-propylpyridine
2-(2'-Fluoro-4'-hexoxybiphenyl-4-yl)-5-propylpyridine
2-(2'-Fluoro-4'-heptoxybiphenyl-4-yl)-5-propylpyridine
2-(2'-Fluoro-4'-pentylbiphenyl-4-yl)-5-butylpyridine
2-(2'-Fluoro-4'-propylbiphenyl-4-yl)-5-butylpyridine
2-(2'-Fluoro-4'-butylbiphenyl-4-yl)-5-butylpyridine
2-(2'-Fluoro-4'-hexylbiphenyl-4-yl)-5-butylpyridine
2-(2'-Fluoro-4'-heptylbiphenyl-4-yl)-5-butylpyridine
2-(2'-Fluoro-4'-propoxybiphenyl-4-yl)-5-butylpyridine
2-(2'-Fluoro-4'-butoxybiphenyl-4-yl)-5-butylpyridine
2-(2'-Fluoro-4'-pentoxybiphenyl-4-yl)-5-butylpyridine
2-(2'-Fluoro-4'-hexoxybiphenyl-4-yl)-5-butylpyridine
2-(2'-Fluoro-4'-heptoxybiphenyl-4-yl)-5-butylpyridine
2-(2'-Fluoro-4'-pentylbiphenyl-4-yl)-5-pentylpyridine
2-(2'-Fluoro-4'-propylbiphenyl-4-yl)-5-pentylpyridine
2-(2'-Fluoro-4'-butylbiphenyl-4-yl)-5-pentylpyridine
2-(2'-Fluoro-4'-hexylbiphenyl-4-yl)-5-pentylpyridine
2-(2'-Fluoro-4'-heptylbiphenyl-4-yl)-5-pentylpyridine
2-(2'-Fluoro-4'-propoxybiphenyl-4-yl)-5-pentylpyridine
2-(2'-Fluoro-4'-butoxybiphenyl-4-yl)-5-pentylpyridine
2-(2'-Fluoro-4'-pentoxybiphenyl-4-yl)-5-pentylpyridine
2-(2'-Fluoro-4'-hexoxybiphenyl-4-yl)-5-pentylpyridine
2-(2'-Fluoro-4'-heptoxybiphenyl-4-yl)-5-pentylpyridine
2-(2'-Fluoro-4'-pentylbiphenyl-4-yl)-5-hexylpyridine
2-(2'-Fluoro-4'-propylbiphenyl-4-yl)-5-hexylpyridine
2-(2'-Fluoro-4'-butylbiphenyl-4-yl)-5-hexylpyridine
2-(2'-Fluoro-4'-hexylbiphenyl-4-yl)-5-hexylpyridine
2-(2'-Fluoro-4'-heptylbiphenyl-4-yl)-5-hexylpyridine
2-(2'-Fluoro-4'-propoxybiphenyl-4-yl)-5-hexylpyridine
2-(2'-Fluoro-4'-butoxybiphenyl-4-yl)-5-hexylpyridine
2-(2'-Fluoro-4'-pentoxybiphenyl-4-yl)-5-hexylpyridine
2-(2'-Fluoro-4'-hexoxybiphenyl-4-yl)-5-hexylpyridine
2-(2'-Fluoro-4'-heptoxybiphenyl-4-yl)-5-hexylpyridine
2-(2'-Fluoro-4'-pentylbiphenyl-4-yl)-5-heptylpyridine
2-(2'-Fluoro-4'-propylbiphenyl-4-yl)-5-heptylpyridine
2-(2'-Fluoro-4'-butylbiphenyl-4-yl)-5-heptylpyridine
2-(2'-Fluoro-4'-hexylbiphenyl-4-yl)-5-heptylpyridine
2-(2'-Fluoro-4'-heptylbiphenyl-4-yl)-5-heptylpyridine
2-(2'-Fluoro-4'-propoxybiphenyl-4-yl)-5-heptylpyridine
2-(2'-Fluoro-4'-butoxybiphenyl-4-yl)-5-heptylpyridine
2-(2'-Fluoro-4'-pentoxybiphenyl-4-yl)-5-heptylpyridine
2-(2'-Fluoro-4'-hexoxybiphenyl-4-yl)-5-heptylpyridine
2-(2'-Fluoro-4'-heptoxybiphenyl-4-yl)-5-heptylpyridine
2-(trans-4-(trans-p-Ethylcyclohexyl)cyclohexyl)-5-propylpyridine
2-(trans-4-(trans-p-Propylcyclohexyl)cyclohexyl)-5-propylpyridine
2-(trans-4-(trans-p-Butylcyclohexyl)cyclohexyl)-5-propylpyridine
2-(trans-4-(trans-p-Pentylcyclohexyl)cyclohexyl)-5-propylpyridine
2-(trans-4-(trans-p-Hexylcyclohexyl)cyclohexyl)-5-propylpyridine
2-(trans-4-(trans-p-Heptylcyclohexyl)cyclohexyl)-5-propylpyridine
2-(trans-4-(trans-p-Ethylcyclohexyl)cyclohexyl)-5-butylpyridine
2-(trans-4-(trans-p-Propylcyclohexyl)cyclohexyl)-5-butylpyridine
2-(trans-4-(trans-p-Butylcyclohexyl)cyclohexyl)-5-butylpyridine
2-(trans-4-(trans-p-Pentylcyclohexyl)cyclohexyl)-5-butylpyridine
2-(trans-4-(trans-p-Hexylcyclohexyl)cyclohexyl)-5-butylpyridine
2-(trans-4-(trans-p-Heptylcyclohexyl)cyclohexyl)-5-butylpyridine
2-(trans-4-(trans-p-Ethylcyclohexyl)cyclohexyl)-5-pentylpyridine
2-(trans-4-(trans-p-Propylcyclohexyl)cyclohexyl)-5-pentylpyridine
2-(trans-4-(trans-p-Butylcyclohexyl)cyclohexyl)-5-pentylpyridine C<20° $S_B$ 164° I
2-(trans-4-(trans-p-Pentylcyclohexyl)cyclohexyl)-5-pentylpyridine 2-(trans-4-(trans-p-Hexylcyclohexyl)cyclohexyl)-5-pentylpyridine
2-(trans-4-(trans-p-Heptylcyclohexyl)cyclohexyl)-5-pentylpyridine
2-(trans-4-(trans-p-Ethylcyclohexyl)cyclohexyl)-5-hexylpyridine
2-(trans-4-(trans-p-Propylcyclohexyl)cyclohexyl)-5-hexylpyridine
2-(trans-4-(trans-p-Butylcyclohexyl)cyclohexyl)-5-hexylpyridine
2-(trans-4-(trans-p-Pentylcyclohexyl)cyclohexyl)-5-hexylpyridine
2-(trans-4-(trans-p-Hexylcyclohexyl)cyclohexyl)-5-hexylpyridine
2-(trans-4-(trans-p-Heptylcyclohexyl)cyclohexyl)-5-hexylpyridine
2-(trans-4-(trans-p-Ethylcyclohexyl)cyclohexyl)-5-heptylpyridine
2-(trans-4-(trans-p-Propylcyclohexyl)cyclohexyl)-5-heptylpyridine
2-(trans-4-(trans-p-Butylcyclohexyl)cyclohexyl)-5-heptylpyridine
2-(trans-4-(trans-p-Pentylcyclohexyl)cyclohexyl)-5-heptylpyridine
2-(trans-4-(trans-p-Hexylcyclohexyl)cyclohexyl)-5-heptylpyridine
2-(trans-4-(trans-p-Heptylcyclohexyl)cyclohexyl)-5-heptylpyridine

EXAMPLE 19

A mixture of 2-(3-nitro-4-cyanophenyl)-5-heptylpyridine (preparable from the known 2-(4-bromophenyl)-5-heptylpyridine by nitration and subsequent substitution of Br by CN by means of CuCN) and caesium fluoride in 1,3-dimethyltetrahydro-2(1H)-pyrimidinone is heated at 110° C. for 4 hours.

Cooling down is followed by pouring onto ice/water and extraction with dichloromethane. Customary working up by chromatography and crystallization gives
2-(3-fluoro-4-cyanophenyl)-5-heptylpyridine.
Prepared analogously:
2-(3-Fluoro-4-cyanophenyl)-5-methylpyridine
2-(3-Fluoro-4-cyanophenyl)-5-ethylpyridine
2-(3-Fluoro-4-cyanophenyl)-5-propylpyridine
2-(3-Fluoro-4-cyanophenyl)-5-butylpyridine
2-(3-Fluoro-4-cyanophenyl)-5-pentylpyridine
2-(3-Fluoro-4-cyanophenyl)-5-hexylpyridine
2-(3-Fluoro-4-cyanophenyl)-5-octylpyridine
2-(3-Fluoro-4-cyanophenyl)-5-nonylpyridine
2-(3-Fluoro-4-cyanophenyl)-5-decylpyridine The examples which follow relate to liquid-crystalline phases according to the invention:

EXAMPLE A

A liquid-crystalline phase consisting of
12% of p-trans-4-propylcyclohexylbenzonitrile,
8% of 2-p-cyanophenyl-5-propyl-1,3-dioxane,
7% of 4-propyl-4'-cyanobiphenyl,
4% of 4-cyanophenyl p-propylbenzoate
4% of 2-fluoro-4-cyanophenyl p-propylbenzoate
16% of trans-1-p-methoxyphenyl-4-propylcyclohexane,
20% of trans-1-p-propylphenyl-4-pentylcyclohexane,
15% of 5-(p-propylphenyl)pyrazin-2-yl 3-fluoro-4-propylbenzoate,
4% of 4,4'-bis-(trans-4-propylcyclohexyl)-biphenyl,
6% of 4-(trans-4-pentylcyclohexyl)-4'-(trans-4-propylcyclohexyl)-biphenyl and
4% of 4,4'-bis-(trans-4-pentylcyclohexyl)-biphenyl has a melting point of −14° and a clear point of +74° C.

EXAMPLE B

A liquid-crystalline phase consisting of 5% of 2-fluoro-4-cyanophenyl p-ethylbenzoate,
5% of 2-fluoro-4-cyanophenyl p-propylbenzoate,
9% of 2-fluoro-4-cyanophenyl p-pentylbenzoate,
10% of 2-fluoro-4-cyanophenyl p-heptylbenzoate
17% of trans-1-p-methoxyphenyl-4-propylcyclohexane,
15% of trans-1-p-ethoxyphenyl-4-propylcyclohexane,
14% of trans-1-p-butoxyphenyl-4-propylcyclohexane,
15% of p-(5-pentylpyridin-2-yl)phenyl 2-fluoro-4-pentylbenzoate,
4% of 4,4'-bis-(trans-4-propylcyclohexyl)biphenyl and
6% of 4-(trans-4-pentylcyclohexyl)-4'-(trans-4-propylcyclohexyl)biphenyl
has a melting point of −11° and a clear point of +68°.

EXAMPLE C

A liquid-crystalline phase consisting of
15% of p-trans-4-propylcyclohexylbenzonitrile,
8% of 4-ethyl-4'-cyanobiphenyl,
7% of 4-propyl-4'-cyanobiphenyl,
15% of trans-1-p-methoxyphenyl-4-propylcyclohexane,
28% of trans-1-p-ethoxyphenyl-4-propylcyclohexane,
15% of 5-pentyl-2-[trans-p-(trans-4-butylcyclohexyl)cyclohexyl]pyridine and
12% of 4-ethyl-4'-(trans-4-propylcyclohexyl)-biphenyl
has a melting point of −22° and a clear point of +64°.

EXAMPLE D

A liquid-crystalline phase consisting of
10% of p-trans-4-ethylcyclohexylbenzonitrile,
15% of p-trans-4-propylcyclohexylbenzonitrile,
15% of p-trans-4-butylcyclohexylbenzonitrile,
20% of p-trans-4-pentylcyclohexylbenzonitrile,
12% of p-trans-4-hexylcyclohexylbenzonitrile,
11% of p-trans-4-heptylcyclohexylbenzonitrile and
17% of 2-p-[2'-(trans-4-pentylcyclohexyl)ethyl]-phenyl-5-propylpyridine
has a melting point of −11° and a clear point of +62° C.

EXAMPLE E

A liquid-crystalline phase consisting of
3% of 2-p-hexyloxyphenyl-5-octylpyrimidine,
3% of 2-p-heptyloxyphenyl-5-octylpyrimidine,
3% of 2-p-octyloxyphenyl-5-octylpyrimidine,
3% of 2-p-nonyloxyphenyl-5-octylpyrimidine,
5% of 2-p-hexyloxyphenyl-5-nonylpyrimidine,
20% of 2-p-nonyloxyphenyl-5-nonylpyrimidine,
5% of 1-(5-nonylpyridin-2-yl)-2-(p-nonyloxyphenyl)ethane,
8% of 1-(5-nonylpyridin-2-yl)-2-(4'-nonyloxybiphenyl-4-yl)ethane,
10% of r-1-cyano-1-octyl-cis-4-(4'-nonyloxybiphenyl-4-yl)cyclohexane,
20% of r-1-cyano-1-octyl-cis-4-(4'-octyloxybiphenyl-4-yl)cyclohexane,
10% of r-1-cyano-1-hexyl-cis-4-(4'-heptylbiphenyl-4-yl)cyclohexane, and
10% of 4-(5-hexylpyridin-2-yl)phenyl 2-chloroisovalerate
has the phase transitions Sc* 58° $S_A$ 61° Ch 78° I and a spontaneous polarization of 11 nC/cm$^2$.

We claim:

1. In a liquid crystalline phase comprising at least two liquid crystal components, the improvement wherein at least one liquid crystal component is a pyridine compound of formula Ien $$R^1\text{-Py-Phe-Z}^2\text{-Cy-R}^2 \qquad \text{Ien}$$

wherein
$R^1$ and $R^2$ are each independently of each other alkyl of 1-15 C atoms, wherein one or two non-adjacent CH$_2$ groups can also be replaced by O atoms and/or —CO— groups and/or —O—CO— groups and/or —CO—O— groups and/or —CHCN— and/or —CH—halogen groups, and one of the radicals $R^1$ and $R^2$ can also be F, Cl, Br, or CN; is pyridine-2,5-diyl;
Phe is a 1,4-phenylene group which is unsubstituted or monosubstituted by F;
$Z^2$ is —CO—O— or —O—CO—; and
Cy is a 1,4-cyclohexylene group.

2. A phase of claim 1, wherein $Z^2$ in formula Ien is —O-CO—.

3. A phase of claim 1, wherein $R^1$ and $R^2$ are each alkyl of 1-15 C atoms, alkyloxy, or oxaalkyl having 1-14 C atoms in the alkyl part.

4. A phase of claim 1, wherein Phe is 1,4-phenylene.

5. A phase of claim 1, wherein the pyridine compound of formula Ien has the following structure

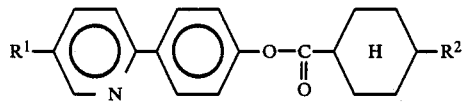

wherein $R^1$ and $R^2$ are each an alkyl group of 1-15 C atoms.

6. A phase of claim 5, wherein said pyridine compound is
4-(5-Nonylpyridin-2-yl)-phenyl trans-4-propylcyclohexanecarboxylate
4-(5-Nonylpyridin-2-yl)-phenyl trans-4-butylcyclohexanecarboxylate
4-(5-Nonylpyridin-2-yl)-phenyl trans-4-pentylcyclohexanecarboxylate
4-(5-Nonylpyridin-2-yl)-phenyl trans-4-hexylcyclohexanecarboxylate
4-(5-Nonylpyridin-2-yl)-phenyl trans-4-heptylcyclohexanecarboxylate
4-(5-Nonylpyridin-2-yl)-phenyl trans-4-octylcyclohexanecarboxylate
4-(5-Octylpyridin-2-yl)-phenyl trans-4-propylcyclohexanecarboxylate
4-(5-Octylpyridin-2-yl)-phenyl trans-4-butylcyclohexanecarboxylate
4-(5-Octylpyridin-2-yl)-phenyl trans-4-pentylcyclohexanecarboxylate
4-(5-Octylpyridin-2-yl)-phenyl trans-4-hexylcyclohexanecarboxylate
4-(5-Octylpyridin-2-yl)-phenyl trans-4-heptylcyclohexanecarboxylate
4-(5-Octylpyridin-2-yl)-phenyl trans-4-octylcyclohexanecarboxylate.

7. A phase of claim 5, wherein said pyridine compound is
4-(5-Heptylpyridin-2-yl)-phenyl trans-4-propylcyclohexanecarboxylate
4-(5-Heptylpyridin-2-yl)-phenyl trans-4-butylcyclohexanecarboxylate
4-(5-Heptylpyridin-2-yl)-phenyl trans-4-pentylcyclohexanecarboxylate
4-(5-Heptylpyridin-2-yl)-phenyl trans-4-hexylcyclohexanecarboxylate
4-(5-Heptylpyridin-2-yl)-phenyl trans-4-heptylcyclohexanecarboxylate
4-(5-Heptylpyridin-2-yl)-phenyl trans-4-octylcyclohexanecarboxylate
4-(5-Hexylpyridin-2-yl)-phenyl trans-4-propylcyclohexanecarboxylate
4-(5-Hexylpyridin-2-yl)-phenyl trans-4-butylcyclohexanecarboxylate
4-(5-Hexylpyridin-2-yl)-phenyl trans-4-pentylcyclohexanecarboxylate
4-(5-Hexylpyridin-2-yl)-phenyl trans-4-hexylcyclohexanecarboxylate
4-(5-Hexylpyridin-2-yl)-phenyl trans-4-heptylcyclohexanecarboxylate
4-(5-Hexylpyridin-2-yl)-phenyl trans-4-octylcyclohexanecarboxylate.

8. A phase of claim 5, wherein said pyridine compound is
4-(5-Pentylpyridin-2-yl)-phenyl trans-4-propylcyclohexanecarboxylate
4-(5-Pentylpyridin-2-yl)-phenyl trans-4-butylcyclohexanecarboxylate
4-(5-Pentylpyridin-2-yl)-phenyl trans-4-pentylcyclohexanecarboxylate
4-(5-Pentylpyridin-2-yl)-phenyl trans-4-hexylcyclohexanecarboxylate
4-(5-Pentylpyridin-2-yl)-phenyl trans-4-heptylcyclohexanecarboxylate
4-(5-Pentylpyridin-2-yl)-phenyl trans-4-octylcyclohexanecarboxylate
4-(5-Butylpyridin-2-yl)-phenyl trans-4-propylcyclohexanecarboxylate
4-(5-Butylpyridin-2-yl)-phenyl trans-4-butylcyclohexanecarboxylate
4-(5-Butylpyridin-2-yl)-phenyl trans-4-pentylcyclohexanecarboxylate
4-(5-Butylpyridin-2-yl)-phenyl trans-4-hexylcyclohexanecarboxylate
4-(5-Butylpyridin-2-yl)-phenyl trans-4-heptylcyclohexanecarboxylate
4-(5-Butylpyridin-2-yl)-phenyl trans-4-octylcyclohexanecarboxylate 9. A phase of claim 5, wherein said pyridine compound is
4-(5-Propylpyridin-2-yl)-phenyl trans-4-propylcyclohexanecarboxylate
4-(5-Propylpyridin-2-yl)-phenyl trans-4-butylcyclohexanecarboxylate
4-(5-Propylpyridin-2-yl)-phenyl trans-4-pentylcyclohexanecarboxylate
4-(5-Propylpyridin-2-yl)-phenyl trans-4-hexylcyclohexanecarboxylate
4-(5-Propylpyridin-2-yl)-phenyl trans-4-heptylcyclohexanecarboxylate
4-(5-Propylpyridin-2-yl)-phenyl trans-4-octylcyclohexanecarboxylate
4-(5-Ethylpyridin-2-yl)-phenyl trans-4-propylcyclohexanecarboxylate
4-(5-Ethylpyridin-2-yl)-phenyl trans-4-butylcyclohexanecarboxylate
4-(5-Ethylpyridin-2-yl)-phenyl trans-4-pentylcyclohexanecarboxylate
4-(5-Ethylpyridin-2-yl)-phenyl trans-4-hexylcyclohexanecarboxylate
4-(5-Ethylpyridin-2-yl)-phenyl trans-4-heptylcyclohexanecarboxylate
4-(5-Ethylpyridin-2-yl)-phenyl trans-4-octylcyclohexanecarboxylate.

10. In an electro-optical display element comprising a liquid crystalline phase, the improvement wherein the phase is one of claim 1.

* * * * *